(12) United States Patent
Washington et al.

(10) Patent No.: US 11,529,318 B2
(45) Date of Patent: Dec. 20, 2022

(54) DEVICES AND METHODS FOR LOCAL DELIVERY OF TACROLIMUS

(71) Applicants: UNIVERSITY OF PITTSBURGH—OF THE COMMONWEALTH SYSTEM OF HIGHER EDUCATION, Pittsburgh, PA (US); DEPARTMENT OF VETERANS AFFAIRS, Washington, DC (US)

(72) Inventors: Kia M. Washington, Pittsburgh, PA (US); William R. Wagner, Gibsonia, PA (US); Michael Brandt Steketee, Wexford, PA (US); Yolandi Van der Merwe, Pittsburgh, PA (US); Xinzhu Gu, Jefferson Hills, PA (US)

(73) Assignees: UNIVERSITY OF PITTSBURGH—OF THE COMMONWEALTH SYSTEM OF HIGHER EDUCATION, Pittsburgh, PA (US); DEPARTMENT OF VETERANS AFFAIRS, Washington, DC (US)

(*) Notice: Subject to any disclaimer, the term of this patent is extended or adjusted under 35 U.S.C. 154(b) by 65 days.

(21) Appl. No.: 16/011,281

(22) Filed: Jun. 18, 2018

(65) Prior Publication Data

US 2018/0369160 A1    Dec. 27, 2018

Related U.S. Application Data

(60) Provisional application No. 62/524,149, filed on Jun. 23, 2017.

(51) Int. Cl.
*A61K 9/70* (2006.01)
*A61P 25/00* (2006.01)
(Continued)

(52) U.S. Cl.
CPC .......... *A61K 9/7007* (2013.01); *A61K 9/0024* (2013.01); *A61K 31/436* (2013.01); *A61K 47/34* (2013.01); *A61P 25/00* (2018.01)

(58) Field of Classification Search
None
See application file for complete search history.

(56) References Cited

U.S. PATENT DOCUMENTS

| 2004/0117008 | A1* | 6/2004 | Wnendt | A61L 31/16 |
| | | | | 623/1.46 |
| 2008/0208323 | A1* | 8/2008 | El-Kurdi | D01D 5/0076 |
| | | | | 623/1.36 |

(Continued)

FOREIGN PATENT DOCUMENTS

WO    WO-2012083594 A1 *  6/2012  ............... A61F 2/82

OTHER PUBLICATIONS

Mutsuga et al. "A new strategy for prevention of anastomotic stricture using tacrolimus-eluting biodegradable nanofiber", The journal of Thoracic and Cardiovascular Surgery. vol. 137, No. 3, pp. 703-709. (Year: 2009).*

(Continued)

*Primary Examiner* — Isis A Ghali
(74) *Attorney, Agent, or Firm* — Baker Botts L.L.P.

(57) ABSTRACT

Devices for local delivery of tacrolimus or a derivative thereof are provided, wherein the devices comprise a polymeric matrix containing tacrolimus or a derivative thereof that provides for delayed and extended release of tacrolimus or a derivative thereof. The devices can locally deliver tacrolimus or a derivative thereof to injured nervous system tissue upon implantation in a subject. Thus, techniques for local delivery of tacrolimus or a derivative thereof and methods of treatment using such devices are also provided.

30 Claims, 28 Drawing Sheets

(51) Int. Cl.
  A61K 47/34    (2017.01)
  A61K 31/436   (2006.01)
  A61K 9/00     (2006.01)

(56) References Cited

U.S. PATENT DOCUMENTS

2008/0299169 A1* 12/2008 Hoffman-Kim ..... A61K 38/185
                                              424/423
2011/0229551 A1*  9/2011 Doshi ............... D01D 5/0007
                                              514/180
2014/0377213 A1* 12/2014 Hong ................ A61L 27/58
                                              424/78.38

OTHER PUBLICATIONS

Sarhane et al. "enhanced nerve regeneration by minimizing intraneural scarring using semi-permeable nanofiber wrap", Plastic and Reconstructive Surgery, Oct. 2014, vol. 134—Issue 4S-1—p. 54-55. (Year: 2014).*
Kehoe et al. "FDA approved guidance conduit and wraps for peripheral nerve injury: A review of material and efficacy", Injury, Int. J. Care Injured 43, 553-572 (Year: 2012).*
Ahearn et al., "FKBP12 Binds to Acylated H-Ras and Promotes Depalmitoylation," Mol. Cell 41(2):173-185 (2011).
Barres et al., "Immunological, Morphological, and Electrophysiological Variation among Retinal Ganglion Cells Purified by Panning," Neuron 1:791-803 (1988).
Bei et al., "Restoration of Visual Function by Enhancing Conduction in Regenerated Axons," Cell 164(1-2):219-232 (2016).
Bottiger et al., "Tacrolimus whole blood concentrations correlate closely to side-effects in renal transplant recipients," Br J Clin Pharmacol 48:445-448 (1999).
Cai et al., "Evaluation of cellular organization and axonal regeneration through linear PLA foam implants in acute and chronic spinal cord injury," J Biomed Mater Res 83A:512-520 (2007).
Cottrell et al., "Neuroregeneration in Composite Tissue Allografts: Effect of low-dose FK506 and Mycophenolate Mofetil Immunotherapy," Plast Reconstr Surg 118:615-623 (2006).
Davaus Gasparetto et al., "Pulmonary toxicity associated with sirolimus following kidney transplantation: computed tomography findings," Nefrologia 30(2):259-260 (2010).
Dehghani et al., "Tacrolimus Related Hypertrophic Cardiomyopathy in Liver Transplant Recipients," Arch Iran Med, 13(2):116-119 (2010).
De Lima et al., "Combinatorial Therapy Stimulates Long-Distance Regeneration, Target Reinnervation, and Partial Recovery of Vision After Optic Nerve Injury in Mice," Int. Rev Neurobiol 106:153-172 (2012).
Den Dunnen et al., "Peripheral nerve regeneration through P(DLLA-ε-CL) nerve guides," J Mater Sci Mater Med 9:811-814 (1998).
Deuse et al., "Mechanisms behind Local Immunosuppression using Inhaled Tacrolimus in Preclinical Models of Lung Transplantation," Am J Respir Cell Mol. Biol. 43:403-412 (2010).
Fischer et al., "Counteracting the Nogo Receptor Enhances Optic Nerve Regeneration if Retinal Ganglion Cells Are in an Active Growth State," J Neurosci 24(7):1646-1651 (2004).
Freeman et al., "The Effects of FK506 on Retinal Ganglion Cells after Optic Nerve Crush," Invest Ophthalmol Vis Sci 41:1111-1115 (2000).
Fukuta et al., "Treatment of stroke with liposomal neuroprotective agents under cerebral ischemia conditions," Eur J Pharm Biopharm 97:1-7 (2015).
Fu et al., "Contributing Factors to Poor Functional Recovery after Delayed Nerve Repair: Prolonged Axotomy," J Neurosci 15(5):3876-3885 (1995).
Gabriel et al., "Improved topical delivery of tacrolimus: A novel composite hydrogel formulation for the treatment of psoriasis," J. Control Release 242:16-24 (2016).

Gnatta et al., "Use of Tacrolimus and the Development of Posttransplant Diabetes Mellitus: A Brazilian Single-Center, Observational Study," Transplant Proc 42:475-478 (2010).
Gold et al., "Non-FK506-Binding Protein-12 Neuroimmunophilin Ligands increase Neurite Elongation and Accelerate Nerve Regeneration," J Neurosci Res 80:56-65 (2005).
Gold et al., "Immunophilin FK506-Binding Protein 52 (Not FK506-Binding Protein 12) Mediates the Neurotrophic Action of FK506," J Pharmacol Exp Ther 289(3):1202-1210 (1999).
Gold et al., "Efficacy of delayed or discontinuous FK506 administrations on nerve regeneration in the rat sciatic nerve crush model: lack of evidence for a conditioning lesion-like effect," Neurosci Lett 267:33-36 (1999).
Goldberg et al., "Amacrine-Signaled Loss of Intrinsic Axon Growth Ability by Retinal Ganglion Cells," Science 296:1860-1864 (2002).
Gottschaldt et al., "Merkel cell receptors: structure and transducer function," Science 214(4517):183-186(1981).
Guan et al., "Synthesis, characterization, and cytocompatibility of elastomeric, biodegradable poly(ester-urethane) ureas based on poly(caprolactone) and putrescine," J Biomed Mater Res 61:493-503 (2002).
Hadlock et al., "A Novel, Biodegradable Polymer Conduit Delivers Neurotrophins and Promotes Nerve Regeneration," Laryngoscope 109:1412-1416 (1999).
Hong et al., "Tailoring the degradation kinetics of poly(ester carbonate urethane)urea thermoplastic elastomers for tissue engineering scaffolds," Biomaterials 31(15):4249-4258 (2010).
Hong et al., "Mechanical properties and in vivo behavior of a biodegradable synthetic polymer microfiber-extracellular matrix hydrogel biohybrid scaffold," Biomaterials 32(13):3387-3394 (2011).
Horn et al., "Another barrier to regeneration in the CNS: Activated macrophages induce extensive retraction of dystrophic axons through direct physical interactions," J Neurosci 28(38):9330-9341 (2008).
Houdek et al., "Management and Complications of Traumatic Peripheral Nerve Injuries," Hand Clin, 31:151-163 (2015).
Howrie et al., "Anaphylactoid Reactions Associated with Parenteral Cyclosporine Use: Possible Role of Cremophor EL," Drug Intell Clin Pharm 19:425-427 (1985).
Jean et al., "Reperfusion Injury after Focal Cerebral Ischemia: The Role of Inflammation and the Therapeutic Horizon," Neurosurgery 43:1382-1397 (1998).
Kim et al., "Effects of FK-506 and CTLA4-Ig on nerve allografts in mice," J Plast Reconstr Aesthet Surg, 67:e49-e53 (2014).
Klettner et al., "The immunophilin-ligands FK506 and V-10,367 mediate neuroprotection by the heat shock response," Br J Pharmacol 138:1004-1012 (2003).
Konofaos et al., "FK506 and Nerve Regeneration: Past, Present, and Future," J Reconstr Microsurg 29:141-148 (2013).
Labroo et al., "Controlled Delivery of FK506 to Improve Nerve Regeneration." Shock 46(Suppl. 1):154-159 (2016).
Labroo et al., "Effect of Combining FK506 and Neurotrophins on Neurite Branching and Elongation," Muscle Nerve 55(4):570-581 (2017).
Lamprecht et al., "Design of pH-sensitive microspheres for the colonic delivery of the immunosuppressive drug tacrolimus," Eur J Pharm Biopharm 58:37-43 (2004).
Lapteva et al., "Polymeric Micelle Nanocarriers for the Cutaneous Delivery of Tacrolimus: a Targeted Approach for the Treatment of Psoriasis," Mol. Pharm 11:2989-3001 (2014).
Lee et al., "Angular Tuning and Velocity Sensitivity in Different Neuron Classes Within Layer 4 of Rat Barrel Cortex," J Neurophysiol 91:223-229 (2004).
Leroy et al., "Tacrolimus nephrotoxicity: beware of the association of diarrhea, drug interaction and pharmacogenetics," Pediatr Nephrol 25:965-969 (2010).
Li et al., "Effect of FK506 nanospheres on regeneration of allogeneic nerve after transplant," Asian Pac J Trop Med 7(6):478-482 (2014).
Lichtenstein et al., "Responses of Rat Trigeminal Ganglion Neurons to Movements of Vibrissae in Different Directions," Somatosensory Mot Res. 7(1):47-65 (1990).
Liu et al., "Calcineurin is a Common Target of Cyclophilin-Cyclosporin A and FKBP-FK506 Complexes," Cell 66:807-815 (1991).

(56) References Cited

OTHER PUBLICATIONS

Liu et al., "Cross talk between activation of microglia and astrocytes in pathological conditions in the central nervous system," Life Sci 89:141-146 (2011).
Lyons et al., "Immunosuppressant FK506 promotes neurite outgrowth in cultures of PC12 cells and sensory ganglia," PNAS USA 91:3191-3195 (1994).
Madduri et al., "Growth factor delivery systems and repair strategies for damaged peripheral nerves," J Control Release 161:274-282 (2012).
Madsen et al., "Tacrolimus (FK506) Increases Neuronal Expression of GAP-43 and Improves Functional Recovery after Spinal Cord Injury in Rats," Exp Neurol 154:673-683 (1998).
Mayer et al., "Multicenter Randomized Trial Comparing Tacrolimus (FK506) and Cyclosporine in the Prevention of Renal Allograft Rejection1: A Report of the European Tacrolimus Multicenter Renal Study Group," Transplantation 64(3):436-443 (1997).
Noble et al., "Analysis of Upper and Lower Extremity Peripheral Nerve Injuries in a Population of Patients with Multiple Injuries," J. Trauma 45:116-122 (1998).
Oto et al., "Calcineurin Inhibitor-Related Cholestasis Complicating Lung Transplantation," Ann Thorac Surg, 89:1664-1665 (2010).
Pabari et al., "Nerve Conduits for Peripheral Nerve Surgery," Plast Reconstr Surg 133(6):1420-1430 (2014).
Pernet et al., "Lost in the jungle: new hurdles for optic nerve axon regeneration," Trends Neurosci 37(7):381-387 (2014).
Peruzzotti-Jametti et al., "The role of the immune system in central nervous system plasticity after acute injury," Neuroscience 283:210-221 (2014).
Randhawa et al., "Tacrolimus (FK506)-Associated Renal Pathology," Adv Anat Pathol 4(4):265-276 (1997).
Resnikoff et al., "Global data on visual impairment in the year 2002," Bulletin World Health Organization 82:844-851 (2004).
Rice, "Gradual Changes in the Structure of the Barrels During Maturation of the Primary Somatosensory Cortex in the Rat," J Comp Neurol. 236:496-503 (1985).
Rosenstiel et al., "Differential Effects of Immunophilin-Ligands (FK506 and V-10,367) on Survival and Regeneration of Rat Retinal Ganglion Cells In Vitro and after Optic Nerve Crush In Vivo," J Neurotrauma 20(3):297-307 (2003).
Russo et al., "Retinal ganglion cell death in glaucoma: exploring the role of neuroinflammation," Eur J Pharmacol. 787:134-142 (2016).
Sarikcioglu et al., "A standardized method to create optic nerve crush: Yasargil aneurysm clip," Exp Eye Res 84:373-377 (2007).
Schmidt et al., "Neural Tissue Engineering: Strategies for Repair and Regeneration," Annu Rev Biomed Eng. 5:293-347 (2003).
Shahraki et al., "Influence of Tacrolimus (FK506) on Nerve Regeneration Using Allografts: A Rat Sciatic Nerve Model," J Oral Maxillofac Surg, 73:1438.e1-1438.e9 (2015).
Sharifi et al., "Effects of FK506 on Hippocampal CA1 Cells Following Transient Global Ischemia/Reperfusion in Wistar Rat," Stroke Res Treat, Article ID 809417, 8 pages (2012).
Silver et al., "Regeneration beyond the glial scar," Nat Rev Neurosci 5:146-156 (2004).
Simons, "Multi-whisker stimulation and its effects on vibrissa units in rat SmI barrel cortex," Brain Research 276:178-182 (1983).
Stankus et al., "Fabrication of biodegradable elastomeric scaffolds with sub-micron morphologies," J Biomed Mater Res A. 70(4):603-614 (2004).
Starzl et al., "FK 506 for Liver, Kidney, and Pancreas Transplantation," Lancet 2(8670):1000-1004 (1989).
Steketee et al., "Regulation of Intrinsic Axon Growth Ability at Retinal Ganglion Cell Growth Cones," Invest Ophthalmol Vis Sci 55(7):4369-4377 (2014).
Szydlowska et al., "Neuroprotectant FK506 inhibits glutamate-induced apoptosis of astrocytes in vitro and in vivo" J Neurochem 99:965-975 (2006).
Tajdaran et al. "A Novel Polymeric Drug Delivery System for Localized and Sustained Release of Tacrolimus (FK506)," Biotechnol Bioeng 112:1948-1953 (2015).
Tang et al., "Soluble Myelin-Associated Glycoprotein Released from Damaged White Matter Inhibits Axonal Regeneration," Mol. Cell Neurosci 18:259-269 (2001).
Tricot et al., "Tacrolimus-Induced Alopecia in Female Kidney-Pancreas Transplant Recipients," Transplantation 80:1546-1549 (2005).
Tocci et al., "The immunosuppressant FK506 selectively inhibits expression of early T cell activation genes," J Immunol 143:718-726 (1989).
Varghese et al., "Tacrolimus-related adverse effects in liver transplant recipients: Its association with trough concentrations," Indian J Gastroenterol 33(3):219-225 (2014).
Voda et al., "Neuroimmunophilin Ligands Improve Functional Recovery and Increase Axonal Growth after Spinal Cord Hemisection in Rats," J. Neurotrauma 22(10):1150-1161 (2005).
Wang et al., "FK506 Increases the Regeneration of Spinal Cord Axons in a Predegenerated Peripheral Nerve Autograft," J Spinal Cord Med 22(4):287-296 (1999).
Xu et al., "FKBP12 is the only FK506 Binding Protein Mediating T-cell Inhibition by the Immunosuppressant FK506," Transplantation 73(11):1835-1848 (2002).
Yamazoe et al., "Efficacy and Safety of Systemic Tacrolimus in High-Risk Penetrating Keratoplasty after Graft Failure with Systemic Cyclosporine," Cornea 33:1157-1163 (2014).
Yang et al., "Experimental research on end-to-side anastomosis of peripheral nerves and effect of FK506 on end-to-side anastomosis," Bratisl Lek Listy 115(10):625-631 (2014).
Young, "Stem cells in the mammalian eye: a tool for retinal repair," APMIS 113:845-857 (2005).
Zhang et al., "Experimental study of FK506 sustained release membrane applied to allogeneic nerve transplantation," Chin J Hand Surg 23(1):8-10 (2007).
Zawadzka et al., "Early steps of microglial activation are directly affected by neuroprotectant FK506 in both in vitro inflammation and in rat model of stroke," J Mol. Med 90:1459-1471 (2012).
Zawadzka et al., "A Novel Mechanism of FK506-Mediated Neuroprotection: Downregulation of Cytokine Expression in Glial Cells," Glia 49:36-51 (2004).

* cited by examiner

PEUU-Tac release

PEUU-Tac remaining weight

Tacrolimus sheet 24 hours post ischemia, fenestrated

Tacrolimus sheet 24 hours post ischemia

Tacrolimus sheet 14 days post ischemia

Tacrolimus sheet 14 days, uninjured

Tacrolimus subcutaneous sheet
14 days post ischemia

Tacrolimus systemic administration
14 days post ischemia

FIG. 7A
| Group | 24 hours | 14 days |
|---|---|---|
| Ischemia, ON sheet | Undetected | Undetected |
| No ischemia, ON sheet | Undetected | 0.30 (± 0.10) ng/ml |
| Ischemia, sub-q sheet | Undetected | 0.26 (± 0.12) ng/ml |
| Ischemia, systemic | 7.05 (± 1.09) ng/ml | 27.86 (± 3.53) ng/ml |
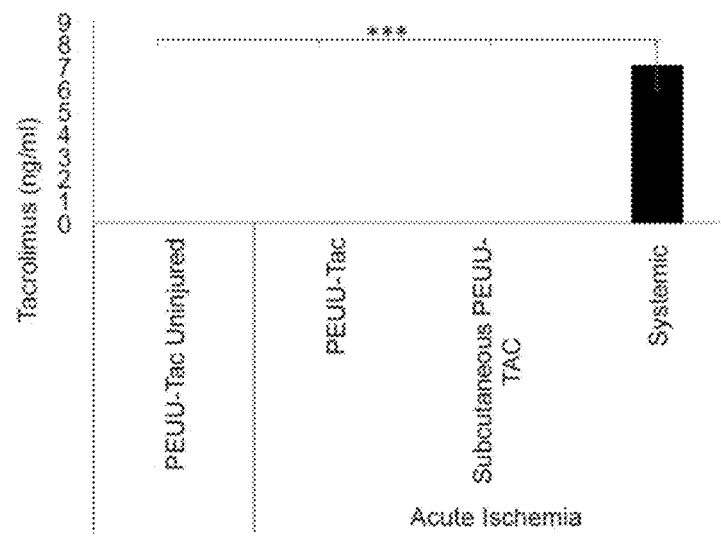
FIG. 7B
Blood concentration after 24 hours
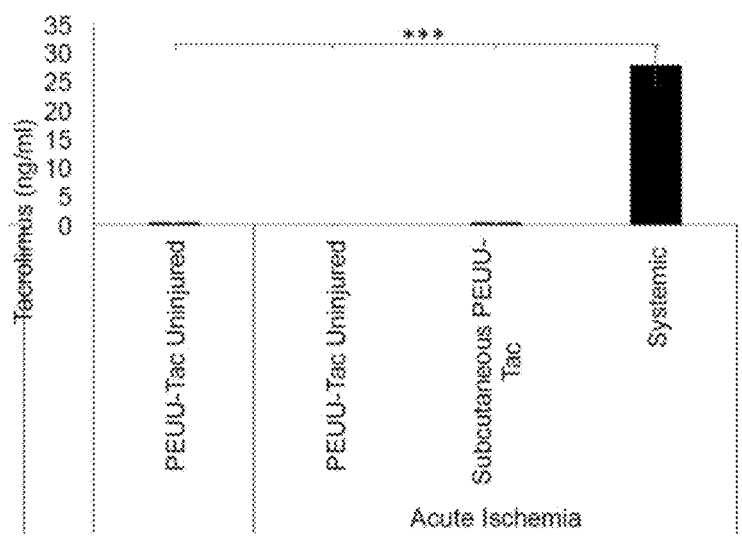
FIG. 7C
Blood concentration after 14 days

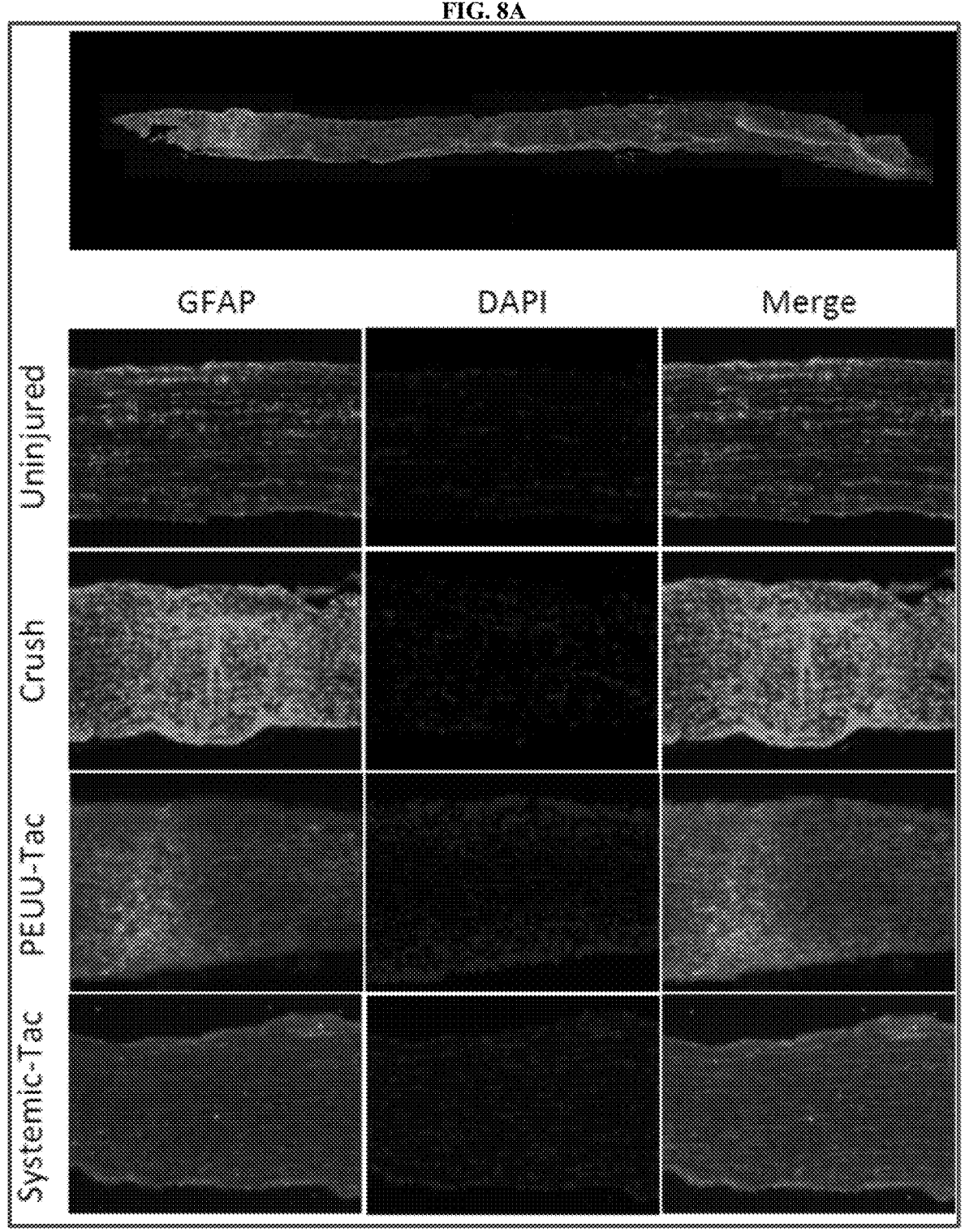

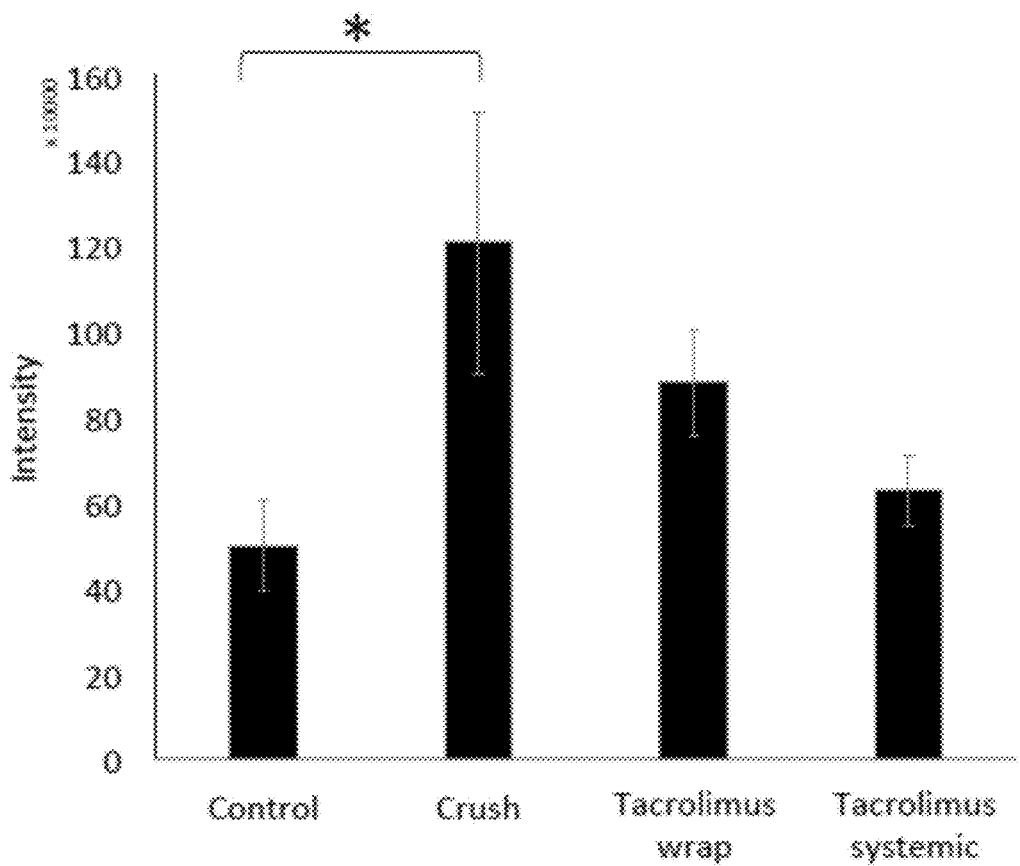

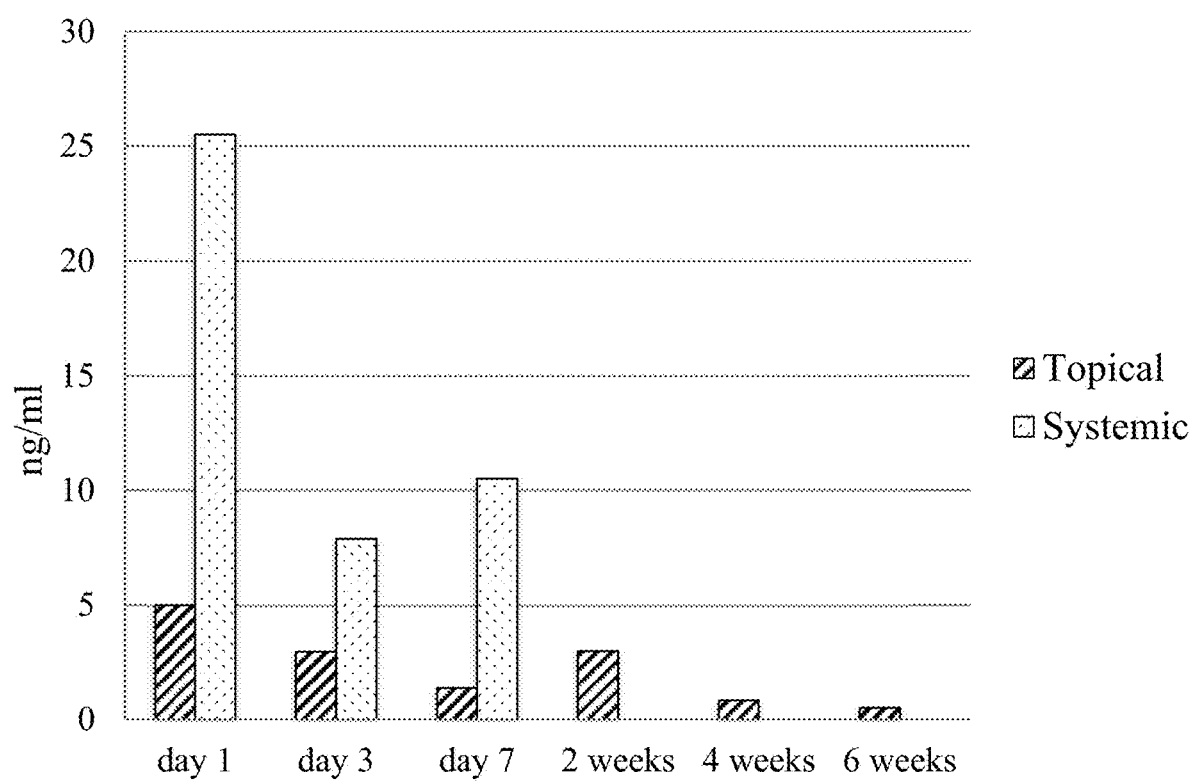

DEVICES AND METHODS FOR LOCAL DELIVERY OF TACROLIMUS

CROSS-REFERENCE TO RELATED APPLICATIONS

This application claims priority to U.S. Provisional Application Ser. No. 62/524,149, filed on Jun. 23, 2017, which is incorporated by reference herein in its entirety.

GRANT INFORMATION

This invention was made with government support under grant number W81XWH-15-1-0026 awarded by the U.S. Army Medical Research and Materiel Command. The government has certain rights in the invention.

1. FIELD

The presently disclosed subject matter relates to techniques for the local delivery of tacrolimus or tacrolimus derivatives to nervous system tissue that are based on devices including tacrolimus or derivatives thereof in a polymeric matrix.

2. BACKGROUND OF THE INVENTION

Injuries and conditions of the nervous system can be difficult to treat, in part due to the healing response in nerves. For instance, in adult mammals, central nervous system (CNS) neurons generally fail to regenerate injured axons after injury due to several factors including lost axon growth potential and a pro-inflammatory innate immune response that can lead to secondary trauma and injury site expansion. Additionally, extracellular matrix (ECM) remodeling can support scar tissue formation that inhibits axon degeneration, possibly leading to CNS neuron death. Unlike nerves of the CNS, the nerves of the peripheral nerve system (PNS) have the capability to regenerate their axons if an injury is relatively small. However, larger injuries will necessitate surgical intervention (Schmidt, C. E et al. 2003). Even with surgical intervention, such as end to end repairs and nerve grafts, the ability of axons to regenerate and the growth support of shwann cells decreases over time (Fu & Gordon et al. 1995), and countless patients exhibit incomplete recovery resulting in substantial disability (Noble J. et al. 1998, Houdek M. T et al. 2015). Combinatorial approaches targeting intrinsic and/or extrinsic factors can increase axon growth to re-innervate target nuclei and restore function. However, several challenges remain and the number of axons that successfully regenerate can be low, remyelination can be incomplete or absent, many axons can misroute, and the methods used can present translational challenges.

Tacrolimus, also called FK506, is an FDA-approved immunosuppressive drug used to treat autoimmune diseases and to reduce the risk of organ transplant rejection. Tacrolimus suppresses T-cell activation primarily by binding to an FK506 binding protein (FKBP) immunophilin receptor, FKBP12, that in turn inhibits calcineurin phosphatase activity and reduces and the expression of early T-cell activation genes. Tacrolimus can also modulate the immune response in the nervous system, including microglial activation, neutrophil infiltration, and astrocyte activation. Because astrocytes and many neurons also express FKBPs, tacrolimus can regulate tissue remodeling through an FKBP-dependent mechanism. Tacrolimus also has neuroprotective and neuroregenerative properties. Tacrolimus can regulate the cell cycle (Ahearn, Tsai et al. 2011) and other cellular functions through FKBP independent mechanisms. In cultured astrocytes, tacrolimus can decrease pro-inflammatory, TNF-α and IL-β, but not anti-inflammatory, TGF-β1 and IL-6, gene expression (Zawadzka and Kaminska 2005), and inhibit astrocyte glutamate toxicity (Szydlowska, Zawadzka et al. 2006). In vivo, systemic tacrolimus can suppress microglial activation (Zawadzka, Dabrowski et al. 2012) and microglial mediated astrocyte activation (Liu, Tang et al. 2011). Tacrolimus can reduce the expression of apoptosis-related genes in astrocytes (Zawadzka, Dabrowski et al. 2012) and down-regulate the expression of pro-inflammatory cytokines in both microglia and astrocytes (Zawadzka and Kaminska 2005), which in turn suppresses oxidative cellular stress (Fukuta, Ishii et al. 2015) and secondary cellular damage and injury site expansion.

Tacrolimus has been shown to have neuroprotective and neuroregenerative activities on neurons in pre-clinical models. Tacrolimus administered orally can promote retinal ganglion cell (RGC) survival after optic nerve crush in rats by suppressing apoptotic signaling (Freeman and Grosskreutz 2000). After spinal cord injury in rats, tacrolimus can increase spinal cord axon growth (Wang and Gold 1999), increase growth associated protein-43 (GAP-43) expression (a neural regeneration marker), and improve functional recovery (Voda, Yamaji et al. 2005; Madsen, MacDonald et al. 1998). In experimental stroke models, tacrolimus can reduce reperfusion injury to CNS neurons (Fukuta, Ishii et al. 2015) and decrease apoptosis in hippocampal neurons (Sharifi, Abolhassani et al. 2012). Furthermore, certain studies have shown that systemic tacrolimus administration can expedite nerve recovery and improve outcomes after nerve injury and repair (Cottrell, B. L et al. 2006, Konofaos, P. et al. 2013, Kim, J. S et al 2014, Yang, L. M et al. 2014, Shahraki, M. et al. 2015). Studies in neurons also suggest that tacrolimus can act on neurons bi-modally, through FKBP dependent and independent mechanisms (Gold, Armistead et al. 2005).

Tacrolimus is typically administered systemically, either orally or by injection. However, high systemic tacrolimus levels can cause life-threatening side effects, including diabetogenicity, nephrotoxicity, and neurotoxicity. Several studies have shown that systemic immunosuppression can be complicated by numerous poorly tolerated, global side effects that can lead to organ failure (Tricot, L., et al. 2005, Oto, T. et al., 2010, Leroy, S. et al., 2010, Gnatta, D. et al 2010, Dehgani. S. M. et al., 2010, Davaus Gasparetto, T. et al., 2010). In order to minimize these side effects, methods to deliver tacrolimus locally have been explored, including topical hydrogels, inhalation-based administration, and micelle or polymer encapsulation. For example, certain studies have focused on various carriers (e.g., nerve wrap) for delivery of tacrolimus (Li et al., 2014, Taidaran et al., 2015). Nerve wraps have been shown to decrease neuroma formation and improve nerve healing when bridging small gaps for nerve repair (Mackinnon 1990, Weber 2000, Meek 2013). However, these approaches can have poor delivery to nervous system tissues or can be unable to match the mechanical properties of nervous system tissues during movement and thus cannot remain in place over the injury site.

Therefore, there remains a need in the art for improved techniques for the local delivery of tacrolimus and derivatives thereof to the nervous system.

3. SUMMARY OF THE INVENTION

The presently disclosed subject matter relates to devices and methods relating to the local delivery of an active agent, e.g., tacrolimus or a tacrolimus derivative, to nervous system tissue.

In certain aspects, a device for local delivery of tacrolimus or a tacrolimus derivative includes a polymeric matrix comprising a biodegradable polymer and tacrolimus or a tacrolimus derivative. In certain non-limiting embodiments, the biodegradable polymer comprises poly(ester urethane) urea (PEUU). The PEUU can have a number average molecular weight ($M_n$) ranging from about 40,000 Da to about 200,000 Da, or from about 50,000 Da to about 100,000 Da.

In certain non-limiting embodiments, the device is configured as a sheet. The device can further include an attachment mechanism for securing the device to nervous system tissue. For example, the attachment mechanism can attach the device to itself and/or directly to the tissue to secure it in place. In certain embodiments, the device can have a Young's modulus of from about 15 MPa to about 30 MPa. The device can have an ultimate stress of at least about 5 MPa. The device can have a strain at break of from about 150% to about 300%. In some embodiments, the geometry of the sheet can be modified based on the geometry of an implantation site.

As embodied herein, the tacrolimus or a tacrolimus derivative can be present in the device in an amount of from about 1 mg to about 100 mg. The biodegradable polymer and the tacrolimus or a tacrolimus derivative can be present in the device in a weight ratio of from about 1:50 to about 1:20.

In certain other aspects, the presently disclosed subject matter relates to methods for local delivery of tacrolimus or a tacrolimus derivative. For example, a method for local delivery of tacrolimus or a tacrolimus derivative to a nervous system tissue in a subject can include applying a polymeric matrix comprising poly(ester urethane) urea and tacrolimus or a tacrolimus derivative to an implantation site in the subject.

In certain non-limiting embodiments, the method can further include securing the polymeric matrix to the implantation site. The tacrolimus or a tacrolimus derivative can be released from the polymeric matrix over a period of from about 10 days to about 15 days. In certain embodiments, the implantation site can be local to the nervous system tissue. In certain embodiments, the nervous system tissue can include a nerve, e.g., an optic nerve and an infra orbital nerve. During local delivery of tacrolimus, the concentration of tacrolimus in blood of the subject can be maintained at less than about 20 ng/mL.

In further aspects, the presently disclosed subject matter provides methods of treating an injury to nervous system tissue. For example, a method of treating an injury to nervous system tissue in a subject can include applying a polymeric matrix comprising poly(ester urethane) urea and tacrolimus or a tacrolimus derivative to the nervous system tissue; and releasing an effective amount of tacrolimus or the tacrolimus derivative to the vicinity of the nervous system tissue.

In certain non-limiting embodiments, the nervous system tissue can include a nerve, e.g., an optic nerve and/or an infra orbital nerve. During treatment, the concentration of tacrolimus in blood of the subject can be maintained at less than about 20 ng/mL.

In certain other aspects, the presently disclosed subject matter provides methods of making a device for local delivery of tacrolimus or a tacrolimus derivative. In certain embodiments, a method of making a device for local delivery of tacrolimus or a tacrolimus derivative can include providing a first solution comprising tacrolimus and a first solvent; providing a second solution comprising a biodegradable polymer and a second solvent; combining the first solution and the second solution to form a mixture; and electrospinning a polymeric matrix comprising a biodegradable polymer and tacrolimus or the tacrolimus derivative from the mixture.

In certain non-limiting embodiments, the method further includes forming the biodegradable polymer in the second solution. For example, the biodegradable polymer can include poly(ester urethane) urea. Poly(ester urethane) urea can be formed in the first solution by reacting polycaprolactone diol, 1,4-diisocyanatobutane, and putrescine.

In certain non-limiting embodiments, the first solvent comprises dimethyl sulfoxide and/or the second solvent comprises hexafluoroisopropanol. In certain non-limiting embodiments, the method further includes sterilizing the device. The device can be sterilized by exposing the device to radiation and/or by contacting the device with ethylene oxide.

4. BRIEF DESCRIPTION OF THE FIGURES

FIG. 1A compares retinal ganglion cells (RGCs) cultured in cell medium with and without tacrolimus (at a concentration of 5 µM) as described in Example 1.

FIGS. 1B-1C shows RGC viability at various concentrations of tacrolimus, ranging from 0 µM to 100 µM, where FIG. 1B is a bar chart of viability and FIG. 1C is the log-transformed data. * indicates significant difference compared to media, p<0.05. Error bars represent SEM, n≥150 randomly analyzed neurons cultured in triplicated from at least 3 experimental repeats.

FIG. 2A provides representative images of RGC neurite growth with media, EtOH (0.025%), and tacrolimus (5 nM).

FIG. 2B shows a bar chart of neurite length in cell media, EtOH, and tacrolimus at various concentrations. The table of FIG. 2B provides the corresponding numerical data. # indicates significant difference compared to media, p<0.05. Error bars represent SEM, ≥30 cells were analyzed for each of 3 experimental repeats, totaling ≥90 neurons per condition.

FIG. 3A shows the surface morphologies of unloaded and 10 mg and 20 mg tacrolimus loaded sheets before (top row) and after (bottom row) degradation in PBS for 8 weeks. The scale bars represent 5 µm.

FIGS. 3B-3C show the release mechanics of 10 mg and 20 mg tacrolimus loaded PEUU sheets. FIG. 3B shows the release of tacrolimus over 14 days and FIG. 3C shows the change in weight of the sheets over 8 weeks. Data represent three experimental repeats, n=3 per group per experiment. Student's t-test between 10 mg and 20 mg sheets at each time point, *p<0.01.

FIGS. 4A-4D show the mechanical properties of an unloaded PEUU sheet and 10 mg and 20 mg tacrolimus loaded PEUU sheets. FIG. 4A provides the stress-strain response; FIG. 4B provides the Young's Modulus; FIG. 4C provides the strain at break of the sheets; and FIG. 4D provides the ultimate stress. One-way ANOVA with Posthoc Tukey's test was performed between groups, *p<0.05. Data represent three experimental repeats, n=3 per group per experiment.

FIGS. 5A-5B illustrate the procedure for acute ischemia. FIG. 5A shows a schematic of acute ischemia via clamping with a tacrolimus sheet sutured around a nerve. FIG. 5B is a photograph taken after the clamping procedure, showing placement of the tacrolimus-PEUU sheet sutured around the optic nerve.

FIGS. 6A-6E illustrate tacrolimus concentration in the left and right optic nerves and retinas 24 hours or 14 days after treatment. FIG. 6A provides tacrolimus concentration 24 hours after suturing a tacrolimus-PEUU sheet to a fenestrated optic nerve (N=4 per tissue). FIG. 6B provides tacrolimus concentration 24 hours after acute ischemia and tacrolimus-PEUU sheet application around the right optic nerve, without fenestration (N=4 per tissue). FIG. 6C provides tacrolimus concentration 14 days after acute ischemia and tacrolimus-PEUU sheet application around the right optic nerve (N=8 per tissue). FIG. 6D provides tacrolimus concentration 14 days after tacrolimus-PEUU sheet application around an uninjured right optic nerve (N=6 per tissue). FIG. 6E provides tacrolimus concentration 14 days after subcutaneous implantation of a tacrolimus-PEUU sheet in the lower right quadrant of the abdomen and acute ischemia to the right optic nerve (N=8 per tissue). FIG. 6F provides tacrolimus concentration 14 days after acute ischemia to the right optic nerve with systemic tacrolimus injections every 48 hours (N=8 per tissue). One-way ANOVA with Posthoc Tukey's test between groups, *p<0.05, p<0.01, *p<0.001.

FIGS. 7A-7C show tacrolimus concentration in the blood after acute ischemia. FIG. 7A provides a chart of tacrolimus concentration after 24 hours and 14 days after (1) acute ischemia and tacrolimus-PEUU sheet application; (2) tacrolimus-PEUU sheet application without ischemia; (3) acute ischemia and with subcutaneous tacrolimus-PEUU sheet application; and (4) acute ischemia with system tacrolimus administration. FIG. 7B illustrates these blood concentrations after 24 hours and FIG. 7C illustrates these blood concentrations after 14 days. One-way ANOVA with Posthoc Tukey's test between groups, ***p<0.001.

FIG. 8A provides images of a representative full nerve, and magnified crush sites showing GFAP staining.

FIG. 8B provides quantification of GFAP intensity showing significant GFAP expression after optic crush. Statistical differences were analyzed by one-way ANOVA with a Tukey post hoc method, and a significance level of p<0.05. Data represent the average± the SEM with the following number of samples: control: n=4; crush: n=2; tacrolimus wrap: n=2; and tacrolimus systemic: n=2.

FIG. 9A provides images of a representative full nerve, and magnified crush sites showing GAP-43 staining.

FIG. 9B provides quantification of GAP-43 intensity showing no significant GAP-43 expression in uninjured, crush only, and tacrolimus systemic treatment, although treatment with tacrolimus wrap caused a significant increase in GAP-43 expression. Statistical differences were analyzed by one-way ANOVA with a Tukey post hoc method, and a significance level of p<0.05. Data represent the average± the SEM with the following number of samples: control: n=3; crush: n=2; tacrolimus wrap: n=3; and tacrolimus systemic: n=2.

FIG. 10 provides an SEM image of a 10 mg wrap in accordance with Example 2, taken at 3000× magnification.

FIG. 12A shows response magnitudes for all samples whereas FIG. 12B provides the average, as compared to a control.

FIG. 13 provides the blood concentrations of tacrolimus when applied as a wrap as compared to systemic administration over 6 weeks.

Figure 14:
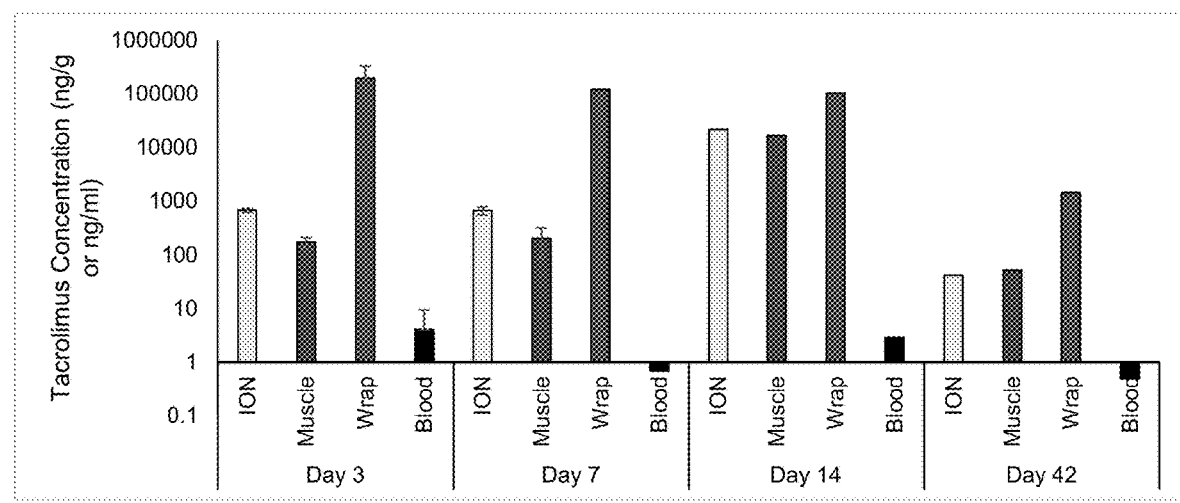

FIG. 14 provides tacrolimus concentrations in the infraorbital nerves (ION, intact), muscles, wrap, and the blood at 3 days, 1 week, 2 weeks, and 6 weeks post PEUU-Tac implantation around IONs.

Figure 15:
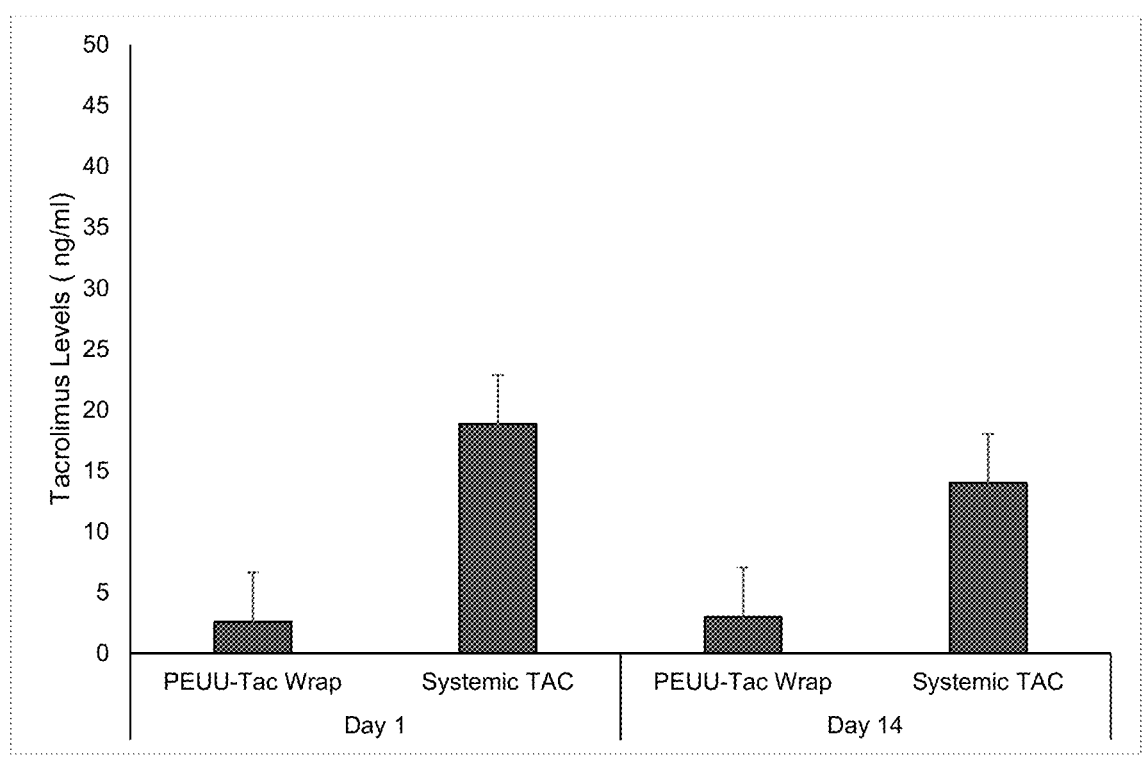

FIG. 15 shows tacrolimus concentrations in the blood at days 1 and 14 post PEUU-Tac wrap implantation around IONs or following systemic tacrolimus administration.

Figure 16A:
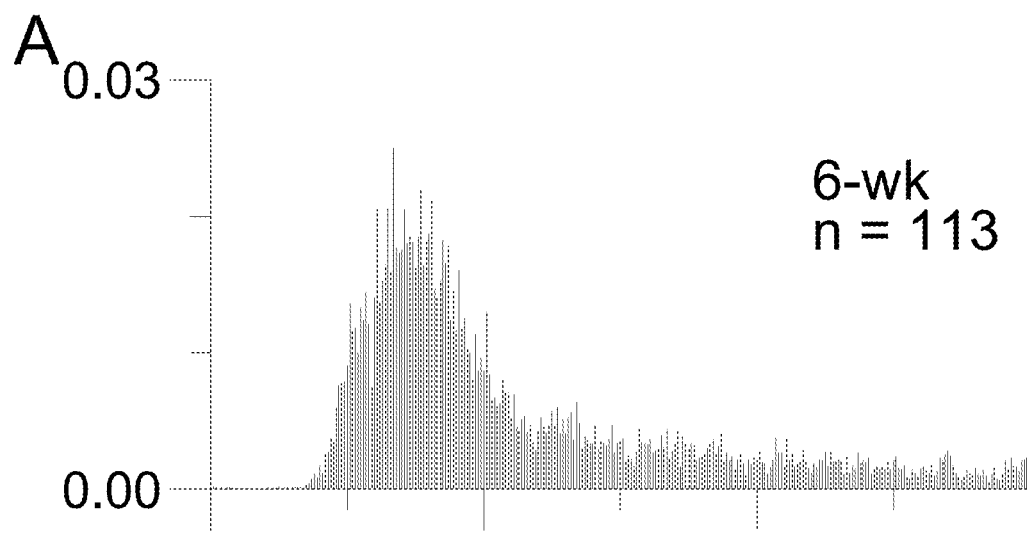
Figure 16B:
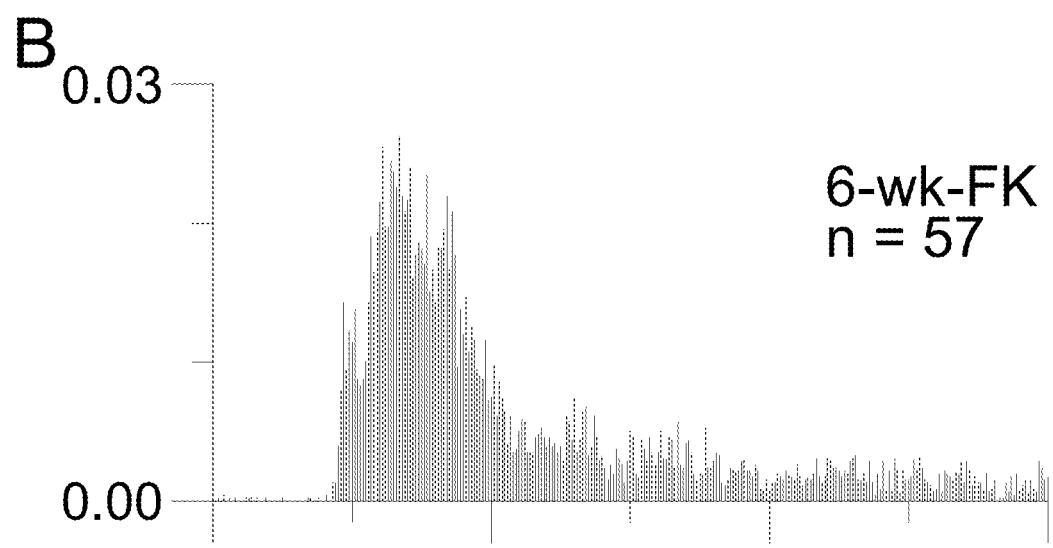
Figure 16C:
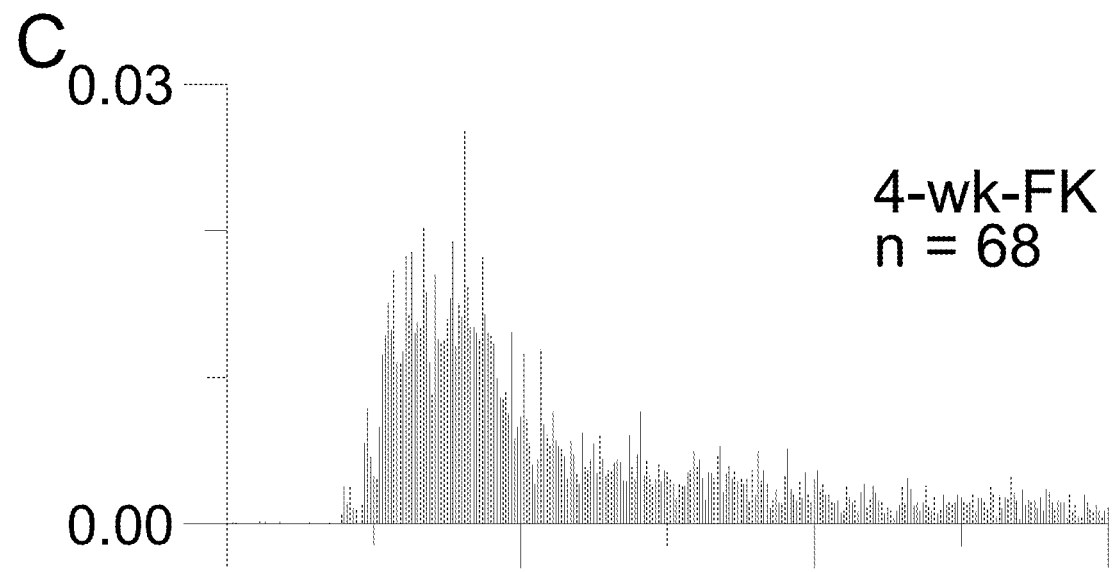
Figure 16D:
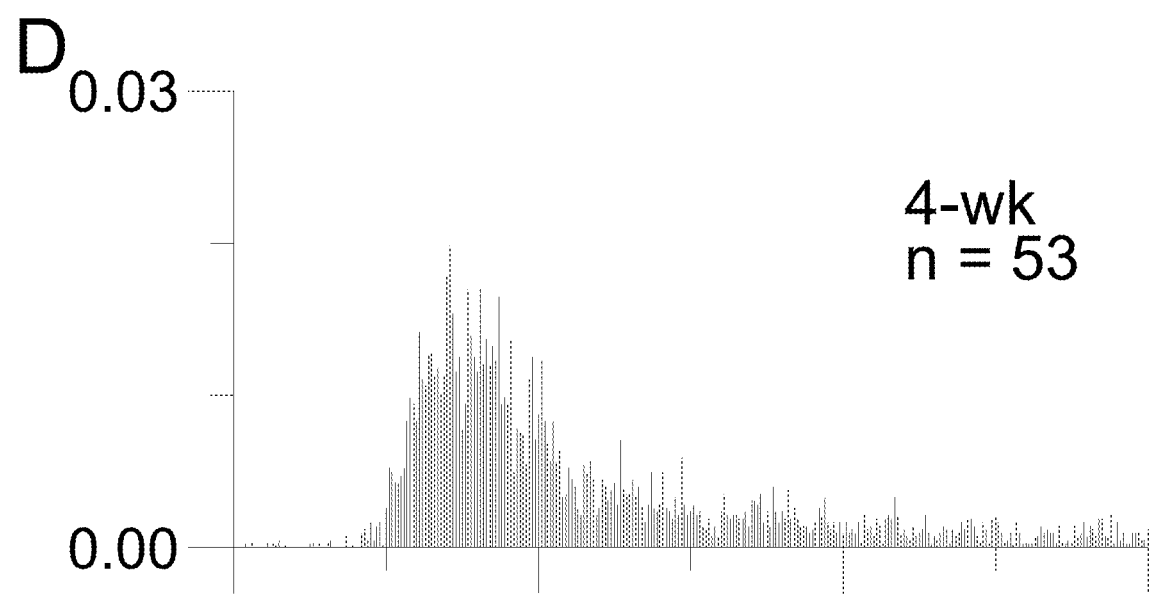
Figure 16E:
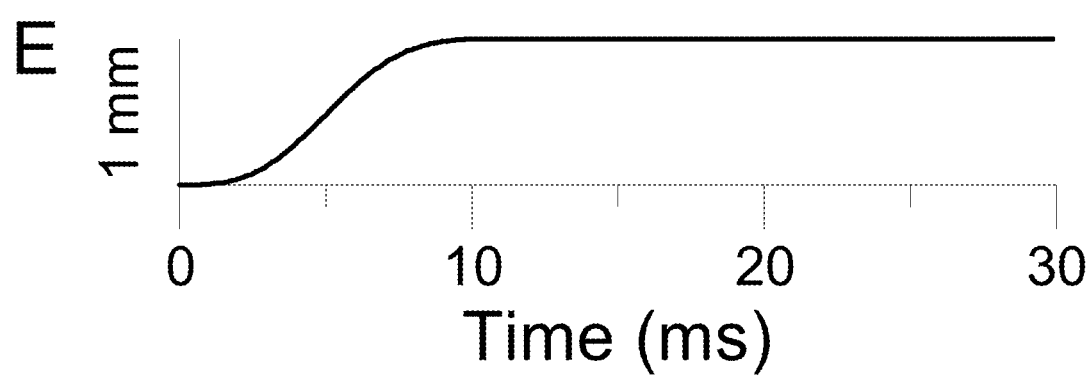

FIGS. 16A-16E show peristimulus time histograms (PSTHs). FIG. 16A provides populations of PSTHs in control animal subjects at six weeks post-transection without FK (n=113). FIG. 16B provides populations of PSTHs in FK-treated animal subjects at six weeks post-transection (n=57). FIG. 16C provides populations of PSTHs in FK-treated animal subjects at four weeks post-transection (n=68). FIG. 16D provides populations of PSTHs in control animal subjects at four weeks post-transection without FK. FIG. 16E provides a stimulus wave form for movement onsets (n=53). FIG. 16A provides populations of PSTHs.

Figure 17A:
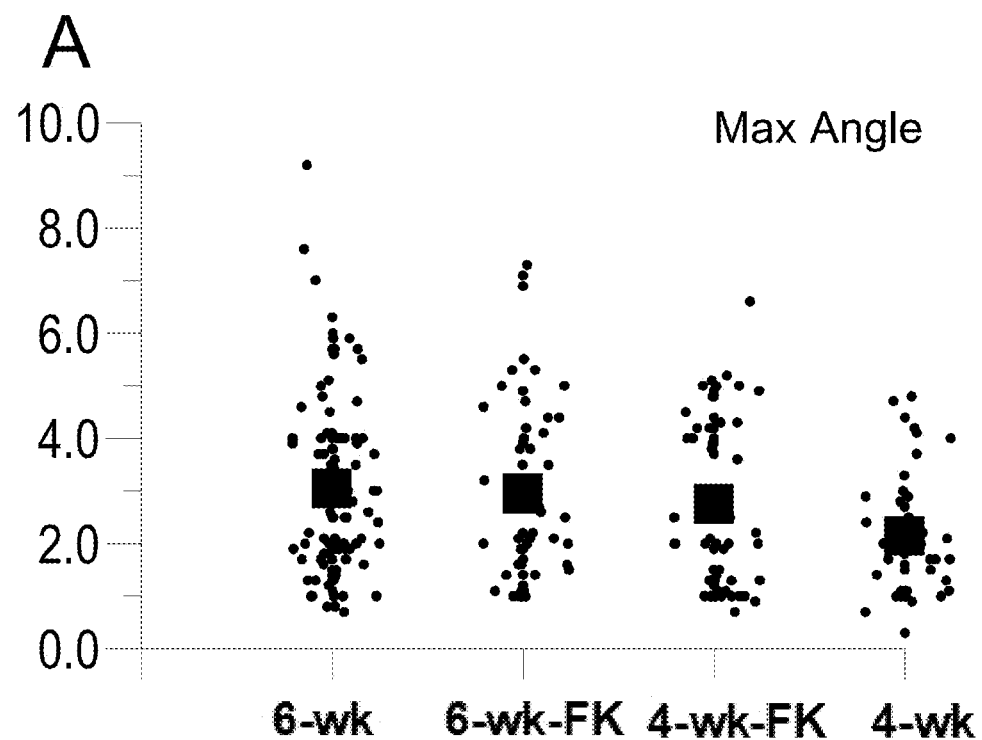
Figure 17B:
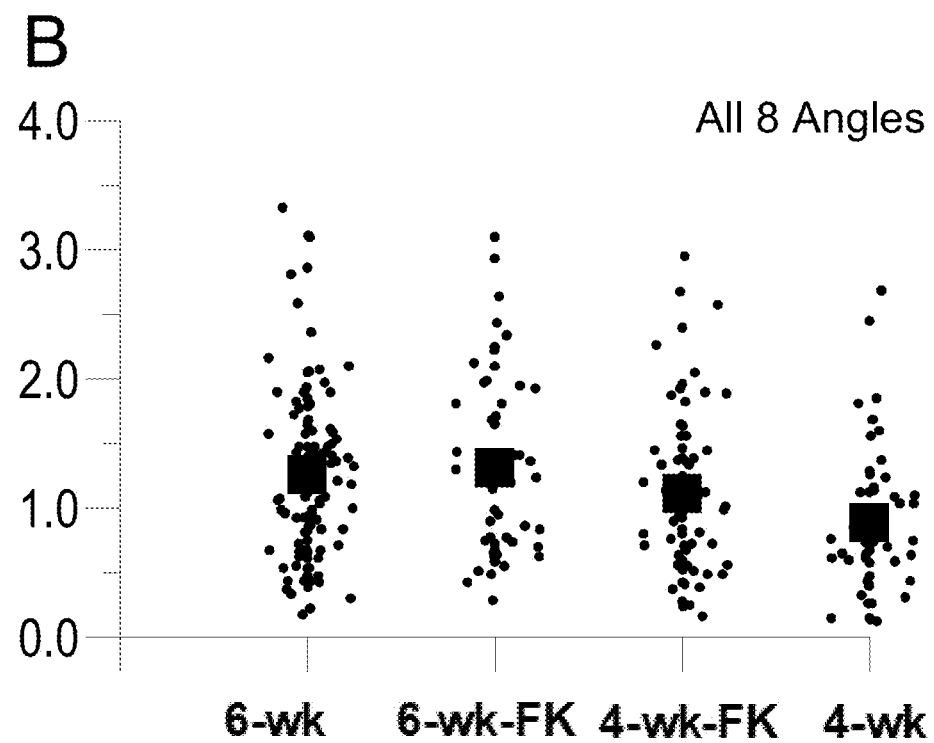
Figure 17C:
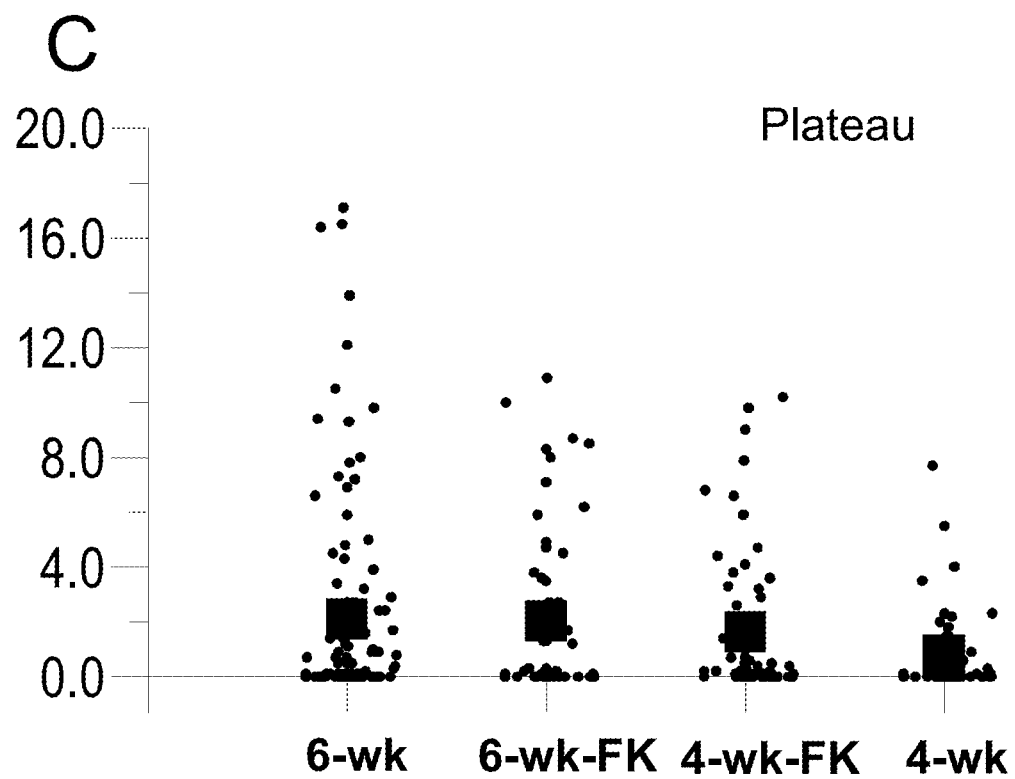

FIGS. 17A-17C show responses to stimulus onsets (ON). ON responses are calculated as the average number of spikes evoked during the first 20 ms of the response following deflection onset. FIG. 17A provides ON responses at each cell's maximally effective direction (Max Angle). FIG. 17B provides ON responses in 8 directions in 45° increments. FIG. 17C provides ON responses during 100 ms of the plateau.

5. DETAILED DESCRIPTION OF THE INVENTION

The presently disclosed subject matter relates to techniques for the local delivery of an active agent, e.g., tacrolimus or a tacrolimus derivative. These techniques can be used to deliver the active agent to nervous system tissue, for example a damaged nerve, and can thereby be used to promote nerve growth and/or neuroregeneration.

The presently disclosed techniques generally relate to a device comprising a polymeric matrix with an active agent disposed therein. The polymeric matrix can be biodegradable such that it degrades and releases the active agent under the conditions of implantation. As such, the disclosed devices can provide for delayed and extended release of the active agent to the nervous system tissue.

To date, many of the materials and methods used to promote regeneration in nervous system tissue are cost prohibitive and not readily translatable to the clinic, due to the nature of their molecular and genetic manipulations. The presently disclosed device is a cost-effective alternative that uses readily-available materials that are already used in FDA approved products. These materials do not produce adverse immune responses and are highly translatable clinically and can be tailored to the appropriate shape and size for implantation while providing an effective amount of active agent.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of", and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "tacrolimus" refers to an immunosuppressive drug, which is also called FK-506 and fujimycin, having the following structure:

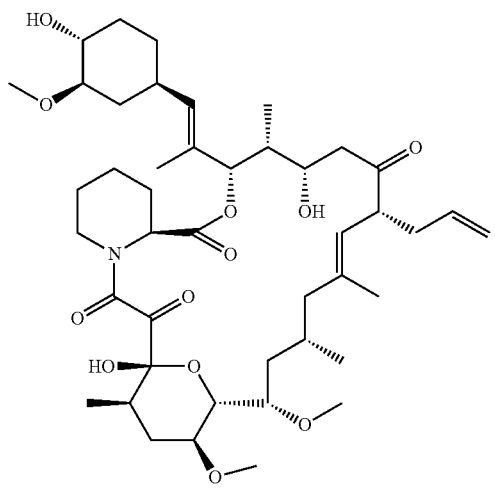 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

As used herein, an "effective amount" refers to an amount of the active agent, e.g., tacrolimus or a derivative thereof, that is able to facilitate regeneration of neurons. An "effective amount" can depend upon the context in which it is being applied, and can be based on several factors, including the condition and/or degree of injury of the neurons, the area being treated, and the duration of the treatment.

A "subject" can be a human or a non-human animal, for example, but not by limitation, a non-human primate, a dog, a cat, a horse, a rodent, a cow, a goat, a rabbit, etc.

For clarity of description, and not by way of limitation, the detailed description of the presently disclosed subject matter is divided into the following subsections:

(1) devices for local delivery of an active agent;
(2) methods of making such devices;
(3) methods for local delivery of an active agent; and
(4) methods of treatment.

5.1. Devices for Local Delivery of Active Agent

In certain aspects, the presently disclosed subject matter relates to devices for the local delivery of an active agent. For example, such devices can comprise a polymeric matrix that contains tacrolimus or a tacrolimus derivative as an active agent. The device can be configured to be applied to an area of nervous system tissue for treatment, e.g., to a nerve of the central nervous system (CNS) and/or peripheral nervous system (PNS).

In certain non-limiting embodiments, the geometry of the device can be modified based on the geometry of an implantation site. For example, and not limitation, the device can be configured as a sheet, wrap, ribbon, tube, or another form configured for therapeutic use. As embodied herein, the device can have any suitable size, shape, and dimensions for application to the target area for implantation. Alternatively, the device can be provided as a larger unit that is cut to the appropriate dimensions and shape prior to application. For example, a sheet or ribbon can be provided having a thickness ranging from about 1 μm to about 4 mm. In some embodiments, the sheet or ribbon can have a wide range of lengths and/or widths. The term "lateral dimension," as used herein, refers to the length and/or width. In accordance with certain embodiments, at least one lateral dimension of the sheet or ribbon structure can be between about 0.1 mm and about 5 cm, between about 0.1 mm and about 1 cm. between about 0.1 mm and about 10 mm, between about 0.1 mm and about 5 mm, or between about 0.1 mm and about 1 mm. When implanted in a subject, the device can be placed in a cylindrical arrangement (e.g., as a wrap or tube around a nerve). For example, such a cylindrical arrangement can have a diameter of from about 1 mm to about 10 mm.

The device can be suitable for implantation into a subject. For example, the device can be applied to a target area in the subject by covering or wrapping the target area with the device by suturing, stapling, adhering with adhesive, tying, or otherwise attaching the device to itself and/or to tissue in the target area. For example, in particular embodiments, the device can be configured as a sheet that is wrapped around a target nerve and sutured in place. In certain embodiments, the size, shape, and dimensions of the device can be modified based on a condition of a target area. For example, prior to implantation, the device can be cut into multiple segments with appropriate size to cover target nerves, muscles, or other tissues. As embodied herein, the target area for implantation can be local to the target area for treatment or can be remote from the target area for treatment, as described in further detail below.

5.1.1. Polymeric Matrices

The presently disclosed devices can be based on a polymeric matrix. As embodied herein, the polymeric matrices can be based on a variety of different polymers. For example, and not limitation, the polymer can be a biodegradable polymer. A biodegradable polymer can break down under the conditions of implantation, i.e., in the nervous system tissue environment. The biodegradable polymer and its degradation products can be biocompatible and non-toxic.

For example, and not limitation, suitable biodegradable polymers include poly(ester urethane) urea (PEUU), polycarbonate urethane urea (PCUU), poly (ether ester urethane) urea, and other degradable polyurethanes, as well as polylactic acid, poly(lactic-co-glycolic) acid, poly(caprolactone), acrylic resins, polyglycolide, polylactide, polyhydroxybutyrate, poly(2-hydroxyethyl-methacrylate), poly(ethylene glycol), polydioxanone, chitosan, hyaluronic acid, hydrogels, and combinations thereof. In other non-limiting embodiments, the device can be based on a non-degradable polymer. For example and not limitation, such non-degradable polymers include silicone rubber, polyethylene, polypropylene, poly(methyl methacrylate) (PMMA), poly(tetrafluoroethylene) (PTFE), polystyrene, polyethylcyanoacrylate, poly(vinyl chloride) (PVC), polyether ether ketone (PEEK), polyether sulfone (PES), and combinations thereof. In certain embodiments, the polymeric matrix can comprise a single type of polymer or a combination of different polymers, e.g., as a polymer blend and/or copolymer. In certain embodiments, the polymeric matrix can comprise a combination of one or more biodegradable polymer and one or more non-degradable polymer. In certain embodiments, the combination of a biodegradable polymer and a non-degradable polymer can itself be biodegradable. In particular embodiments, the polymeric matrix can contain poly(ester urethane) urea (PEUU).

Additionally, the polymer can have a particular molecular weight, which can affect the morphology of the resulting polymeric matrix. For example, in embodiments where the polymeric matrix comprises PEUU, the PEUU can have a number average molecular weight ($M_n$) ranging from about 40,000 Da to about 200,000 Da, or from about 50,000 Da to about 100,000 Da.

The release kinetics of the selected polymer can influence the release rate of an active agent disposed within the polymeric matrix. As such, the polymer can be selected to have a particular degradation profile under the conditions of implantation. For example, and as described in greater detail below, it can be desirable to select a polymer such that there is a constant release of active agent over time in order to maintain a stable local concentration of the active agent at the site of implantation and/or at the target area of treatment. In this manner, the presently disclosed devices can provide for the delayed and extended release of an active agent.

Additionally, the mechanical properties of the polymeric matrix (when combined into a device with the active agent) can be suitable for implantation into a tissue environment. For example, the amount of active agent added can be modulated such that it does not impair the mechanical properties of the polymeric matrix in the device. Desirably, the device can be pliable and strong, but not brittle, such that it can be manipulated prior to implantation and is able to mimic the mechanical movement of the implantation site. As embodied herein, the device can be kink resistance, such that kinks or folds are not formed in the device when it is flexed, e.g., during the implantation procedure or during movement of the subject post-implantation.

In certain non-limiting embodiments, the device can have a Young's modulus of from about 5 MPa to about 50 MPa, or from about 10 MPa to about 40 MPa, or from about 15 MPa to about 30 MPa. Similarly, in certain non-limiting embodiments, the device can have an ultimate stress of at least about 5 MPa. The strain at break of the device can range from about 5% to about 500%, or from about 5% to about 400%, or from about 5% to about 300%, or from about 10% to about 300%, or from about 50% to about 300%. Additionally, in certain non-limiting embodiments, the presently disclosed device can have improved suture retention strength. Suture retention strength refers to the ability of a material to retain sutures when a mechanical force is applied, and can be measured as the peak strength before breakage when force is applied to sutures. Thus, suture retention strength will depend on the testing parameters, including but not limited to the diameter of the suture, the thickness of the tested device, the porosity of the tested device, the distance between the suture and the edge of the tested device, and the angle of the applied force. For example, the suture retention strength of the device can be at least one-fifth that of expanded polytetrafluoroethylene (ePTFE) when the same testing parameters are applied, e.g., at least about 100 gram-force, at least about 200 gram-force, at least about 250 gram-force, or at least about 300 gram-force.

5.1.2. Active Agents

The presently disclosed devices can further include an active agent that is disposed within the polymeric matrix. In particular embodiments, the active agent can be tacrolimus or a derivative thereof, which has neuroprotective and neuroregenerative properties. Although the presently disclosure specifically describes the use of tacrolimus as the active agent, a person of skill in the art will understand that the presently disclosed techniques can be used for the delivery of other active agents, including tacrolimus derivatives and other immunosuppressant agents.

Tacrolimus is approved by the FDA to treat autoimmune diseases and to reduce the risk of organ transplant rejection. Due to its effects on nervous system tissue remodeling and neuroprotective and neuroregenerative properties, it can be desirable to deliver tacrolimus to injured areas of the nervous system to regenerate neurons. Although tacrolimus can be administered systemically (e.g., orally or parenterally), the local levels of tacrolimus that are desirable to benefit the nervous system can have serious and life-threatening side effects. Thus, the presently disclosed subject matter provides devices and methods for local delivery of tacrolimus.

In further non-limiting embodiments, the active agent can be a different agent, other than tacrolimus or a derivative thereof. For example, and not limitation, suitable active agents include prednisone, cyclosporine, sirolimus, everolimus, methotrexate, and mycophenolate mofetil, and combinations thereof. In certain embodiments, the active agent can comprise two or more active agents, e.g., two or more of the particular active agents described herein or one or more of the particular active agents described here and one or more other active agents.

In certain non-limiting embodiments, the active agent, e.g., tacrolimus or a derivative thereof, can be present in the polymeric device in a particular amount to provide an effective amount of the active agent to an injured site within nervous system tissue, as described in further detail below. In certain embodiments, for example where the active agent is tacrolimus, the device can contain from about 1 mg to about 100 mg, or from about 2 mg to about 80 mg, or from about 5 mg to about 50 mg, or from about 10 mg to about 20 mg of the active agent. The amount of active agent can vary depending on the weight and release kinetics of the polymeric matrix, as well as the properties of the particular active agent selected. In certain embodiments, the weight ratio between the active agent and the polymeric matrix can range from about 1:10,000 to about 1:10, from about 1:10,000 to about 1:20, from about 1:10,000 to about 1:50, or from about 1:10,000 to about 1:100, or from about 1:1,000 to about 1:100. In certain non-limiting embodiments, the concentration of the active agent can be constant throughout the polymeric matrix of the device. In alternative embodiments, the concentration of the active agent can vary throughout the polymeric matrix of the device.

5.2. Methods of Making Devices for Local Delivery of Active Agent

The presently disclosed subject matter also relates to methods of making devices for the local delivery of an active agent, e.g., tacrolimus or a derivative thereof. The devices can be made according to any suitable method for manufacturing porous polymeric scaffolds, as is known in the art. For example, the devices can be made by salt leaching, thermally induced phase separation, electrospinning, and other spinning methods. Alternatively, a preformed polymeric nerve guide can be steeped with an active agent, optionally with a solvent or other agent, such that the nerve guide becomes coated and/or impregnated with the active agent.

As embodied herein, devices can be formed by electrospinning polymeric matrices containing an active agent. In certain non-limiting embodiments, methods of making the devices can include dissolving an active agent in a suitable solvent to form a first solution. For example and not limitation, when tacrolimus is used as the active agent, a suitable solvent can be dimethyl sulfoxide (DMSO). Similarly, the methods can further include providing a second solution comprising the polymer of the polymeric matrix. The polymer can be formed in the solution, e.g., by combining two or more reagents to form the polymer in solution. For example, in embodiments where the polymer comprises poly(ester urethane) urea (PEUU), the reagents polycaprolactone diol, 1,4-diisocyanatobutane, and putrescine can be combined in solution to form PEUU. Alternatively, the polymer can be directly added to and dissolved in a solvent to form the second solution. The solvent of the second solution should be suitable for dissolving the selected polymer. For example and not limitation, when the polymer comprises PEUU, the solvent can be hexafluoroisopropanol (HFIP).

The methods can further include combining the first solution and the second solution to provide a mixture of the active agent, e.g., tacrolimus or a derivative thereof, and the polymer, e.g., PEUU, in solution. Thus, the solvents of the first and second solutions should be compatible with each other and with both of the active agent and the polymer. In alternative embodiments, the polymer and active agent can be dissolved together in a single solution.

The device can be formed by electrospinning a polymeric matrix that contains the active agent from the solution containing both of the polymer and the active agent. Electrospinning uses high voltage current to transform the liquid polymer into thin polymer threads, which can form the matrix of the device. The electrospinning can be modulated to control the pore size of the matrix, which can further affect the release of active agent from the device, e.g., by altering the surface area and morphology of the polymeric matrix. For example, the pore size of the matrix can be affected by a number of factors, including the molecular weight and molecular weight distribution of the polymer, the concentration of the polymer in solution, the viscosity, surface tension, and conductivity of the solution, and the process parameters of the electrospinning, such as electric potential, polymer flow rate, the shape of the mandrel, and the distance between the capillary and the mandrel.

In certain non-limiting embodiments, the methods can further include sterilizing the device prior to implantation using any suitable technique, as known in the art. For example, the device can be sterilized by exposure to electromagnetic radiation, such as heat, light, and/or gamma radiation, and/or by electron beam irradiation. Alternatively or additionally, the device can be treated with a sterilizing fluid, such as ethylene oxide (EtO) gas. In certain embodiments, the device can be sterilized upon fabrication and/or immediately prior to implantation.

5.3. Methods of Local Delivery of Active Agent

The presently disclosed subject matter also relates to methods for the local delivery of an active agent, e.g., tacrolimus or a derivative thereof. As embodied herein, the active agent, e.g., tacrolimus a derivative thereof, can be delivered to an area for treatment by applying a delivery device with a polymeric matrix comprising tacrolimus or a derivative thereof.

As described above, tacrolimus binds to FK506 binding protein (FKBP), which is expressed on neurons in the CNS and PNS. Thus, it is desirable to deliver tacrolimus or a derivative thereof locally to nervous system tissue. In certain non-limiting embodiments, the delivery device can be implanted locally to a targeted area for treatment. For example, to treat injuries to a nerve, the device can be applied to the nerve, e.g., by wrapping it around the nerve. As such, tacrolimus or a derivative thereof will be released in the vicinity of the injury.

However, when the device is implanted remotely, released tacrolimus can still accumulate in nervous system tissue (see Example 1). Therefore, in other non-limiting embodiments, the device can be implanted subcutaneously or in another region that is remote from the target area of treatment and released tacrolimus can travel from the device to the target area.

In certain non-limiting embodiments, the device can have a particular degradation profile, which can affect the release rate and profile of active agent (e.g., tacrolimus or a derivative thereof). As such, the devices can be engineered to increase or decrease delivery of tacrolimus or tacrolimus derivatives by tuning the degradation profile of the polymeric matrix. The degradation profile of the device can depend on a number of factors, including but not limited to, the thickness of the device, the type of polymer in the polymeric matrix, and the location of implantation. In certain embodiments, the weight of the device can decrease by at least about 50%, at least about 60%, at least about 70%, or at least about 80% by 8 weeks after implantation. In certain embodiments, the device can completely degrade by up to about 3 months after implantation. In alternative embodiments, the device can comprise a non-degradable polymer such that it does not degrade upon implantation. In such devices, the active agent can be released over time by diffusing through pores of the device.

As embodied herein, the local delivery of active agent, e.g., tacrolimus or a derivative thereof can be estimated by the local concentrations of active agent in nervous system tissue over time. The device can be tuned such that active agent is quickly released, e.g., within the first 24 hours after implantation, followed by a delayed and extended period of release. In certain non-limiting embodiments, the release rate of the active agent can be highest in the first 24 hours after implantation. However, in such embodiments, the overall amount of active agent released in the first 24 hours can be low, to reserve active agent for an extended release period. As such, in certain embodiments, less than 5% or less than 2% of the active agent is released from the device in the first 24 hours. In this manner, the local concentration of active agent can be quickly raised to therapeutic levels and then maintained at those levels over time. For example and as embodied herein, tacrolimus concentrations in nervous system tissue can be maintained at less than about 200,000 ng/mL. For example, the extended period of release can be from about 2 days to about 100 days, or from about 5 days to about 90 days, or from about 10 days to about 90 days, or from about 20 days to about 90 days, or from about 50 days to about 90 days.

Moreover, and as embodied herein, tacrolimus or a derivative thereof can be locally delivered to target tissue while maintaining low blood concentrations of drug. For example, and not limitation, the blood concentration of tacrolimus can be maintained at less than about 20 ng/mL, less than about 15 ng/mL, less than about 10 ng/mL, less than about 5 ng/mL, or less than about 1 ng/mL throughout treatment.

As embodied herein, local delivery of tacrolimus can be validated by studying protein expression in the neurons of the target area for treatment. For example, and not limitation, local delivery of tacrolimus can decrease glial fibrillary acidic protein (GFAP) expression and increase GAP-43 expression as compared to injured, untreated neurons (see Example 1).

5.4. Methods of Treatment

The presently disclosed subject matter also relates to methods of treating injuries to nervous system tissue. For example and not limitation, methods can include applying a polymeric matrix comprising poly(ester urethane) urea and active agent, e.g., tacrolimus or a derivative thereof, to the nervous system tissue and releasing an effective amount of active agent to the vicinity of the nervous system tissue. As embodied herein, the injury can be any physical injury, condition, or disease of the nervous system tissue.

The methods can include treating any type of nervous system tissue. In certain non-limiting embodiments, the targeted nervous system tissue can be areas formed of neurons, e.g., areas of the CNS such as the brain, cerebral cortex, retina, spinal cord, and sensory organs. In certain non-limiting embodiments, the target nervous system tissue can be a nerve, including nerves of the CNS such as cranial nerves and spinal nerves, as well as nerves of the PNS including the somatic nervous system and autonomic nervous system. Non-limiting examples of nerves include the abdominal aortic plexus, abducens nerve, accessory nerve, accessory obturator nerve, Alderman's nerve, anococcygeal nerve, ansa cervicalis, anterior interosseous nerve, anterior superior alveolar nerve, Auerbach's plexus, auriculotemporal nerve, axillary nerve, brachial plexus, buccal nerve, cardiac plexus, cavernous plexus, celiac ganglion, cervical plexus, cervical spinal nerves, chorda tympani, ciliary ganglion, coccygeal nerve, cochlear nerve, common fibular nerve, common palmar digital nerve, cutaneous nerve, deep fibular nerve, deep petrosal nerve, deep temporal nerves, dorsal scapular nerve, esophageal plexus, ethmoidal nerve, external laryngeal nerve, external nasal nerve, facial nerve, femoral nerve, frontal nerve, gastric plexuses, geniculate ganglion, genitofemoral nerve, glossopharyngeal nerve, greater auricular nerve, greater occipital nerve, greater petrosal nerve, hepatic plexus, hypoglossal nerve, iliohypogastric nerve, ilioinguinal nerve, inferior alveolar nerve, inferior anal nerve, inferior cardiac nerve, inferior cervical ganglion, inferior gluteal nerve, inferior hypogastric plexus, inferior mesenteric plexus, inferior palpebral nerve, infraorbital nerve, infraorbital plexus, infratrochlear nerve, intercostal nerves, intercostobrachial nerve, intermediate cutaneous nerve, internal carotid plexus, internal laryngeal nerve, interneuron, jugular ganglion, lacrimal nerve, lateral cord, lateral pectoral nerve, lateral plantar nerve, lateral pterygoid nerve, lesser occipital nerve, lingual nerve, long ciliary nerve, long thoracic nerve, lower subscapular nerve, lumbar nerve, lumbar plexus, lumbar splanchnic nerve, lumboinguinal nerve, lumbosacral plexus, lumbosacral trunk, mandibular nerve, masseteric nerve, maxillary nerve, medial cord, medial cutaneous nerve, medial pectoral nerve, medial plantar nerve, medial pterygoid nerve, median nerve, Meissner's plexus, mental nerve, middle meningeal nerve, motor nerve, musculocutaneous nerve, mylohyoid nerve, nasociliary nerve, nasopalatine nerve, nerve of pterygoid canal, nerve to obturator internus, nerve to quadratus femoris, nerve to the piriformis, nerve to the stapedius, nerve to the subclavius, nervus intermedius, nervus spinosus, nodose ganglion, obturator nerve, occipital nerve, oculomotor nerve, olfactory nerve, ophthalmic nerve, optic nerve, otic ganglion, ovarian plexus, palatine nerve, pancreatic plexus, parasympathetic nerves, patellar plexus, pelvic splanchnic nerves, perforating cutaneous nerve, perineal nerve, petrous ganglion, pharyngeal nerve, pharyngeal plexus, phrenic nerve, phrenic plexus, posterior auricular nerve, posterior cord, posterior scrotal nerve, posterior superior alveolar nerve, prostatic plexus (nervous), pterygopalatine ganglion, pudendal nerve, pudendal plexus, radial nerve, recurrent laryngeal nerve, renal plexus, sacral plexus, sacral splanchnic nerves, saphenous nerve, sciatic nerve, semilunar ganglion, sensory nerve, short ciliary nerve, sphenopalatine nerve, splenic plexus, subcostal nerve, submandibular ganglion, suboccipital nerve, superficial fibular nerve, superior cardiac nerve, superior cervical ganglion, superior gluteal nerve, superior hypogastric plexus, superior labial nerve, superior laryngeal nerve, superior mesenteric plexus, superior rectal plexus, supraclavicular nerve, supraorbital nerve, suprarenal plexus, suprascapular nerve, supratrochlear nerve, sural nerve, sympathetic trunk, thoracic aortic plexus, thoracic splanchnic nerve, thoraco-abdominal nerve, thoracodorsal nerve, tibial nerve, transverse cervical nerve, trigeminal nerve, trochlear nerve, tympanic nerve, ulnar nerve, upper subscapular nerve, uterovaginal plexus, vagus nerve, ventral ramus, vesical nervous plexus, vestibular nerve, vestibulocochlear nerve, zygomatic nerve, zygomaticofacial nerve, and zygomaticotemporal nerve. In particular embodiments, the nervous system tissue is the optic nerve.

EXAMPLES

The following Examples are offered to more fully illustrate the disclosure but are not to be construed as limiting the scope thereof.

Example 1: In Vitro and In Vivo Effects of Device for Local Delivery of Tacrolimus on Optic Nerve and Retinal Tissue This Example illustrates the dose-dependent effects of tacrolimus on retinal ganglion cell (RGC) viability and neurite growth to develop a biodegradable matrix for local tacrolimus delivery to the optic nerve, which is a CNS tissue.

Materials and Methods

Animals. Sprague-Dawley rats from Charles River Laboratories (Wilmington, Mass.) received care in compliance with the University of Pittsburgh Institutional Animal Care and Use Committee and followed guidelines from the Guide for the Care and Use of Laboratory Animals published by the National Institutes of Health.

Retinal ganglion cell isolation. RGCs were isolated from female and male postnatal day three (P3) Sprague-Dawley rat pups, purified by immunopanning, and cultured in NB-SATO media as previously described (Barres, Silverstein et al. 1988). The RGCs were seeded ($5 \times 10^3/cm^2$) on cell culture plates coated with poly-D-lysine (70 kDa, 10 μg/mL; Sigma-Aldrich Corp., St. Louis, Mo., USA) and laminin (2 μg/mL, Sigma-Aldrich Corp.), and maintained at 37° C. in 10% CO2 for 3 days.

RGC viability analysis. To analyze RGC viability a calcein and propidium iodide based live/dead kit was used after 3 DIV per the manufacturer's instructions (Life Technologies, R37601). Briefly, RGC cultures were incubated in the live/dead reagent for 15 minutes at room temperature and five random fields per well were imaged at 20× using standard epi-fluorescence fluorescein and rhodamine filter sets (Zeiss, Axio Observer). Live and dead cells were analyzed using ImageJ (National Institutes of Health, Bethesda, Md., USA). All graphical data represents three independent experimental repeats.

RGC neurite growth analysis. Neurite growth was analyzed as previously described (Steketee, Oboudiyat et al. 2014). Briefly, RGCs were fixed after 3 DIV with 4% paraformaldehyde (Alfa Aesar; 30525-89-4) in PBS, washed with PBS (2×), and permeabilized with 0.2% triton X-100 in PBS for 15 minutes. After blocking for 1 hour (1% BSA, Fisher Scientific), the RGCs were incubated in anti-β III tubulin (1:300, TUJ-1, Millipore) at 4° C. overnight, washed in PBS (3×), incubated with a FITC-rabbit anti-chicken IgY H+L (1:150, #31501, Thermo Scientific) for 3 hours, washed with PBS (3×), counterstained with the nuclear marker DAPI (1:3000, Invitrogen) for 20 minutes at room temperature, and washed in PBS (2×, 5 min. each). The RGCs were observed as above using epifluorescent microscopy and analyzed using the ImageJ plugin, NeuronJ (National Institutes of Health, Bethesda, Md., USA). Neurites were defined as any projection longer than twice the cell body, and branches were quantified as the number of secondary neurites extending from a primary neurite that originated at the cell body. At least 30 neurons were analyzed blindly as previously described for three independent experimental repeats, totaling at least 90 neurons per condition.

PEUU-Tac matrix fabrication. Poly(ester urethane) urea (PEUU) was synthesized from polycaprolactone diol (Mn=2000), 1,4-diisocyanatobutane and putrescine, as described (Guan, Sacks et al. 2002). PEUU-Tac matrices with tacrolimus were fabricated by electrospinning as described (Hong, Huber et al. 2011). Briefly, 10 mg or 20 mg of tacrolimus was dissolved in 500 µl 1,1,1,3,3,3-hexafluoroisopropanol (HFIP). Then, the tacrolimus solution was mixed with 0.45 g PEUU (12% w/v in HFIP) and electrospun onto a rotating stainless steel mandrel (19 mm diameter) by feeding through a charged capillary at a rate of 3 mL/h. The mandrel was located 17 cm from the tip of the capillary. The voltage between the capillary and mandrel was 19 kV. The matrix was sterilized under UV light overnight and then with ETO before animal implantation.

PEUU-Tac release profile. To determine the tacrolimus release rate, PEUU-Tac matrices were cut into three equal weight sections and each section was placed in 25 mL of 0.5% Cremephor EL in PBS (CrEL-PBS; (Howrie, Ptachcinski et al. 1985) in Sigmacoated (Sigma, St. Louis, Mo.) 50 mL glass beakers with gentle agitation. At each time point, 1, 2, 4, 8, and 12 hours, and 3, 7, and 14 days, 300 µl was removed for analysis and then replaced with 300 µl of fresh CrEL-PBS. To analyze tacrolimus levels in CrEL-PBS, 50 µl was removed from each 300 µl CrEL-PBS sample, mixed with 450 µl of blood and then analyzed using HPLC-tandem mass spectrometry as described below.

PEUU-Tac degradation rate. Degradation analysis was done at 37° C. in PBS as described (Hong, Guan et al. 2010). Briefly, equal size samples (10×5×0.1 mm) were cut from an unloaded PEUU matrix or a 10 or 20 mg tacrolimus loaded PEUU matrix and put in 15 mL of PBS in a 20 mL vial. At each time point, the samples were removed from the buffer, washed with deionized water, and dried under vacuum at room temperature for 3 to 4 days before weighing to determine mass lost, using the equation:

$$\text{Mass Remaining (\%)} = \left(\frac{m_d}{m_{orig}}\right) \cdot 100$$

where $m_d$ is the sample after drying and $m_{orig}$ is the original mass. After weighing, each sample was placed in fresh PBS. The time in PBS indicates the total time in PBS, independent of the drying time. The average mass is reported with the error bars indicating one standard deviation. For visualization, the PEUU matrices were sputter-coated with gold/palladium and imaged using standard scanning electron microscopy methods (SEM; JSM-6330F, JEOL USA).

Mechanical properties. To test mechanical properties of PEUU matrices, PEUU or PEUU-Tac matrices were cut into a dumbbell geometry (ASTM D1708) using a custom made dog-bone cutting die with a 2.5 mm width, a 10 mm gauge length, and a total length of 20 mm. PEUU tensile properties were analyzed by uniaxial tensile testing using an MTS Insight (MTS Systems Corporation, Minn., USA) with a 10 N (0.01 N resolution) load cell at room temperature. The samples were extensionally deformed at 10 mm/min, according to ASTM D638M. Young's modulus was calculated by finding the initial slope of the stress versus strain curve (0<ε<10%) using linear regression. The ultimate stress was determined as the maximum stress and the strain-at-break recorded as the strain at the point where the force became zero. This experiment was replicated three times for each sample and the averages reported with the error bars indicating one standard deviation.

Optic nerve ischemia and PEUU-Tac matrix application. Animals were anesthetized by intraperitoneal injection of 45:10 mg/kg ketamine/xylazine cocktail. Once anaesthetized, the optic nerve was exposed by making a small incision and then creating a nearly bloodless plane through the conjunctiva by blunt dissection with #5 forceps. The surrounding muscle and connective tissue around the optic nerve were then gently separated until the optic nerve was exposed. Using a Yasagril aneurysm clip, the right optic nerve was clamped ~2 mm behind the globe for 10 seconds (Sarikcioglu, Demir et al. 2007). After removing the clip, ophthalmic artery integrity was confirmed by visualization. For some animals, the optic nerve sheath was fenestrated at the injury site by making an 1-2 mm incision. For animals receiving PEUU-Tac, a 1×5 mm section cut from a 10 mg PEUU-Tac matrix was sutured around the injury site and then secured by suturing to the outer sheath. After each optic nerve procedure, the conjunctiva was sutured and antibiotic ointment (Gentamicin, Bausch & Lomb, Tampa, Fla.) was applied to the eye. In total, twenty-eight animals received acute optic nerve ischemia to the right optic nerve with or without a PEUU-Tac wrap. The experimental groups were as follows:

(1) Five animals received a 1 mm×5 mm section of a 10 mg PEUU-Tac sheet sutured around the nerve.
(2) Five animals received a 1 mm×5 mm section of a 10 mg PEUU-Tac matrix implanted subcutaneously in the lower right quadrant of the abdomen.
(3) Five animals received daily intraperitoneal injections of tacrolimus (2.2 mg/kg/day) for 14 days with the first injection administered immediately after ischemic injury.
(4) Five animals were used as a sham control.

Blood and tissue collection. Twenty-four hours after injury, blood samples were drawn from all four groups via the tail vein. Four of the eight animals treated with PEUU- Tac were sacrificed at 24 hours and sixteen animals were sacrificed at 14 days. Blood, both retinas and both optic nerves were collected from all animals.

Tacrolimus tissue extraction and reconstitution in blood. Tissue (retina and optic nerve) samples were weighted and homogenized with organic solvent (methanol, 100%) using Mini-BeadBeater-1 sonicator for cell disruption and left over night to assure complete tacrolimus extraction. The homogenate was centrifuged at 2100±100 rpm for 10 min. The methanol was transferred to a microcentrifuge tube and evaporated using a sample concentrator. The drug residue was reconstituted with 1 mL of blood. Tacrolimus in the blood was analyzed as described below and tissue drug concentration was expressed in ng/g of tissue weight.

Quantification of tacrolimus in blood by HPLC-tandem mass spectrometry. Standard curves and quality control blood samples were prepared using tacrolimus powder. Fifty microliters of blood were added to a conical centrifugation tube, followed by 200 µl of zinc sulfate heptahydrate ($ZnSO_4.7H_2O$) to precipitate blood proteins and 500 µl of an acetonitrile-based solution containing an internal standard (ascomycin) at a concentration of 20 ng/l. The mixture was vortexed at 3000 rpm for 2 minutes to ensure optimal precipitation. Samples were centrifuged at 13,000 rpm for 3 minutes with the supernatant poured off and collected into individual glass LCMS vials for analysis. Analysis was performed using a fully validated, reverse phase high performance liquid chromatographic method for the detection of tacrolimus in blood on a Waters micromass Quattro micro API mass spectrometer operated in a positive electrospray ionization mode, utilizing multiple reaction monitoring, and an injection volume of 20 µl. The Waters 2795 Alliance Separations Module was equipped with a nova-pack® C18 column, 2.1×10 mm cartridge (Waters #186003523) and heated to 55° C. Analytes were effectively separated using a gradient elution consisting of an aqueous mobile phase (95% $H_2O$/5% MeOH) and an organic mobile phase (100% MeOH), at a flow rate of 0.6 mL per minute. In order to optimize ionization and enhance the quality of chromatographic output, both mobile phases contained 0.1% formic acid ($CH_2O_2$) and 2 mM ammonium acetate. Monitored parent to product mass transitions for tacrolimus and ascomycin were 821.63→768.33 and 809→756 m/z, respectively. Under these conditions, tacrolimus had a retention time of 1.2 minutes. The method showed an acceptable linearity in the range of 2-40 ng/mL with a correlation coefficient ($R^2$) of 0.9996. Both intra- and inter-day precision were shown to be acceptable (C.V.<10%, n=3) at concentrations of 4.3, 15.7, and 24.6 ng/mL.

Immunohistochemistry. Animals were euthanized 14 days after injury and the retinas and the optic nerves removed, fixed in 4% paraformaldehyde for 4 h, cryoprotected in 30% sucrose for 4 h, embedded in optical cutting temperature (OCT) medium (Tissue-Tek; Miles Inc, Elkhart, Ind.) and placed at 4° C. overnight before freezing in liquid nitrogen. Embedded tissues were stored at −80° C. prior to sectioning (15 µm thickness) on a cryostat. Optic nerve sections were labeled with anti-glial fibrillary acidic protein antibody (anti-GFAP, 1:500, Abcam) or anti-growth associated protein 43 (anti-GAP 43, 1:500, Thermo Scientific), and DAPI. Retinal sections were labeled with anti-GFAP, anti-GAP-43, DAPI, anti-doublecortin (DCX, Abcam), and anti-SOX2 (SOX2, Abcam). Retinal sections were stained with a TUNEL assay kit according to manufacturer's instructions (Click-iT Plus TUNEL Assay, Alexa Fluor 488 Dye, Thermo Scientific).

Statistical analysis. All measurements were performed by blinded individuals. To determine significance between groups (p<0.05), one-way analysis of variance (ANOVA) was used in conjunction with a Turkey's post-hoc test using SPSS Statistical Analysis Software (IBM, Chicago, Ill., USA). All error bars represent standard error of the mean (SEM) unless noted otherwise.

Results

Tacrolimus and RGC viability and neurite growth in vitro. Previous studies indicate that tacrolimus has both neuroprotective and neuroregenerative properties. However, the therapeutic concentration ranges have not been previously reported for RGCs. Therefore, prior to in vivo studies, the dose-response effects of tacrolimus on RGC viability and neurite growth were analyzed using primary RGCs purified from P3 rat retinas.

Figure 1A:
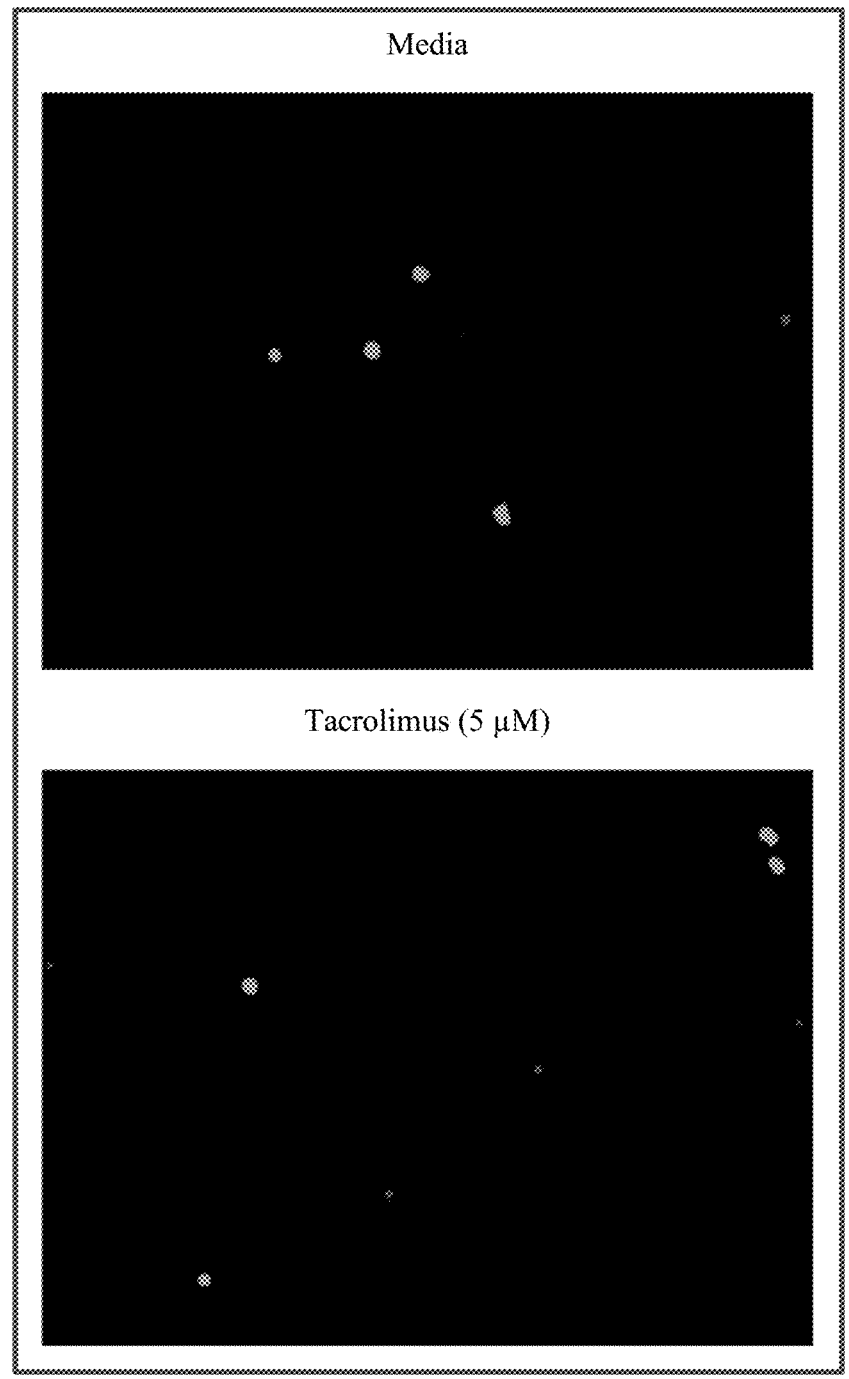
Figure 1B:
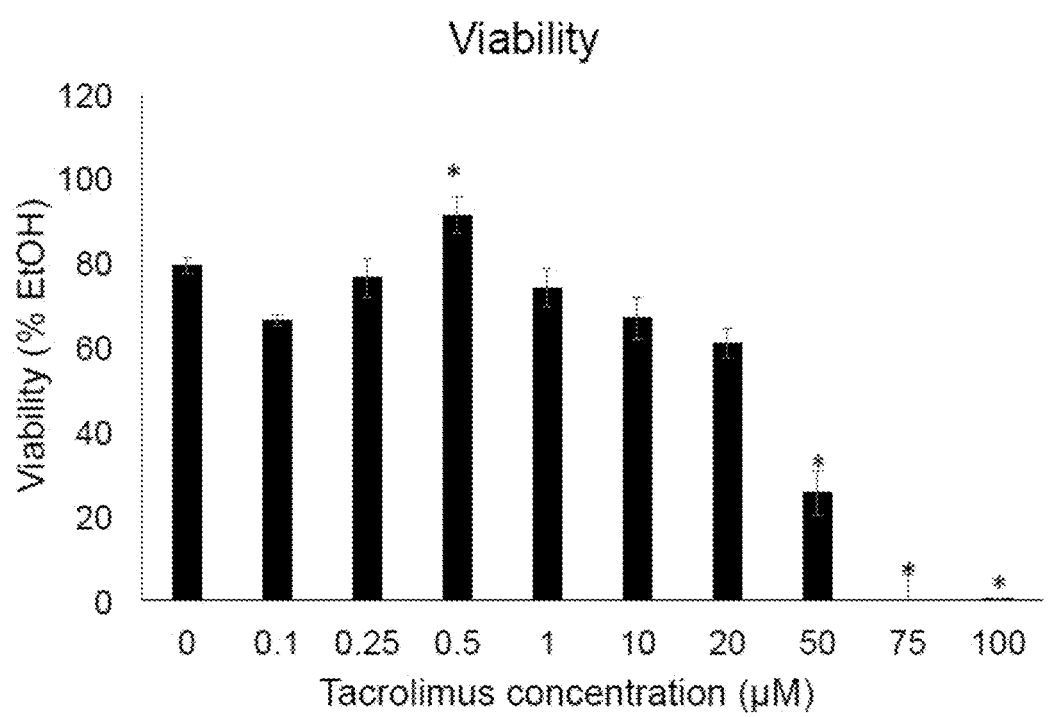
Figure 1C:
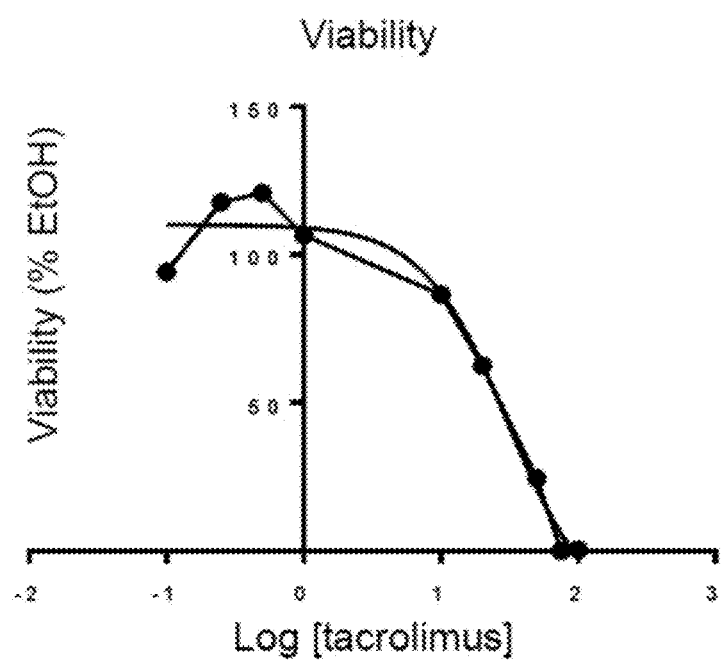

To determine the effects of tacrolimus on RGC viability, RGCs were cultured in tacrolimus concentrations, ranging from 0.1 to 100 µM or in controls that included media or EtOH (0.025%) for 3 days in vitro (FIGS. 1A-1C). At lower concentrations, tacrolimus initially increased RGC cell viability. However, viability of RGCs decreased in higher concentrations of tacrolimus, with an IC50 of 24.17 µM (FIG. 1C). For example, RGC viability initially increased from 70% in EtOH vehicle to 87.4% in 0.5 µM tacrolimus, a 17.4% increase, before decreasing dose-dependently to 0% at 50 µM with IC50=25 µM (FIGS. 1B-1C). Thus, in vitro viability increased at levels outside typical levels used therapeutically, demonstrating that local delivery mechanisms can be needed to safely deliver tacrolimus to CNS tissues in vivo. Moreover, tacrolimus effects on RGC viability in vitro follow a bi-modal dose-response curve suggesting that tacrolimus differentially regulates a single signaling pathway causing a switch from pro-survival to pro-death or that tacrolimus regulates RGC viability by more than one mechanism.

Figure 2A:
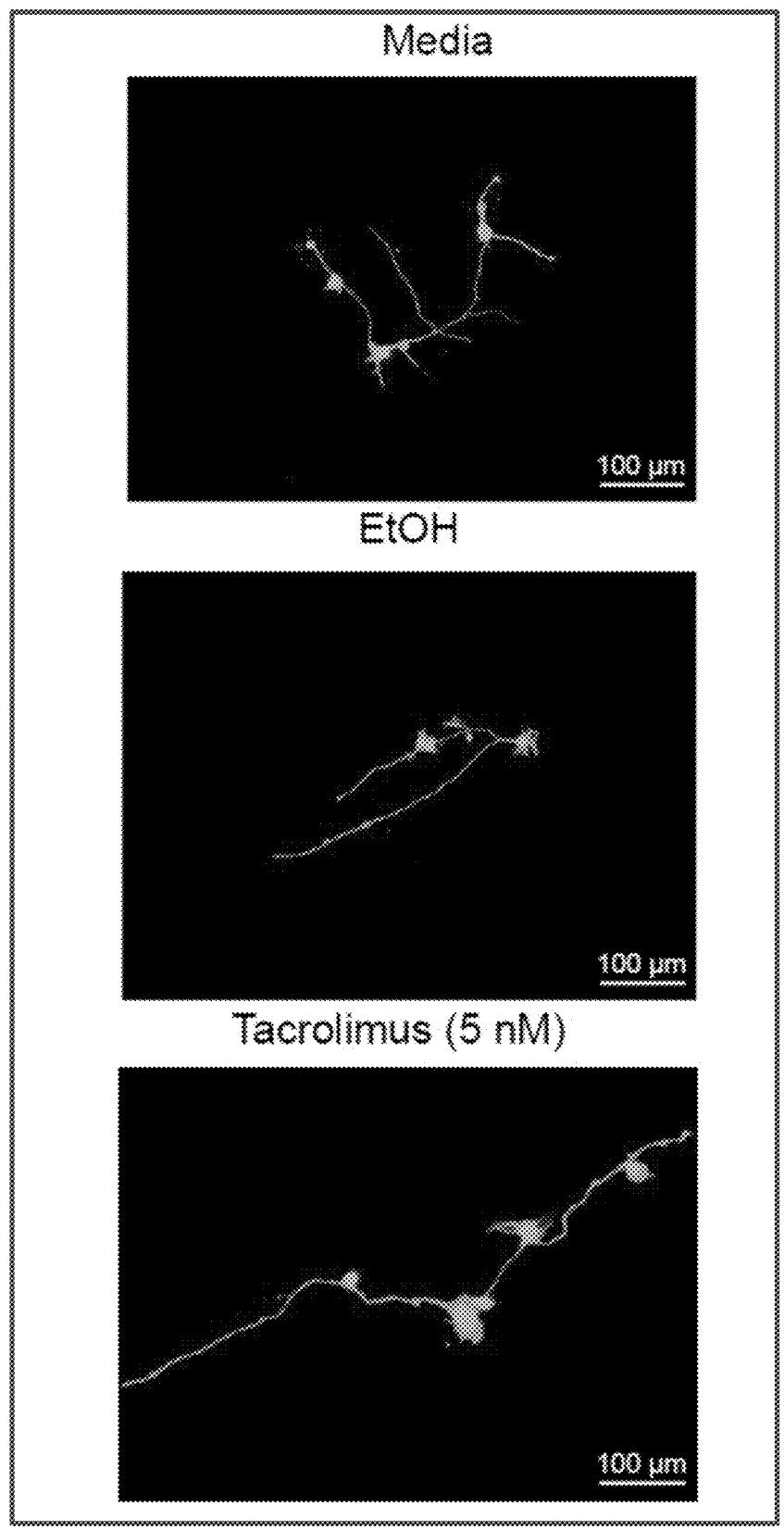
Figure 2B:
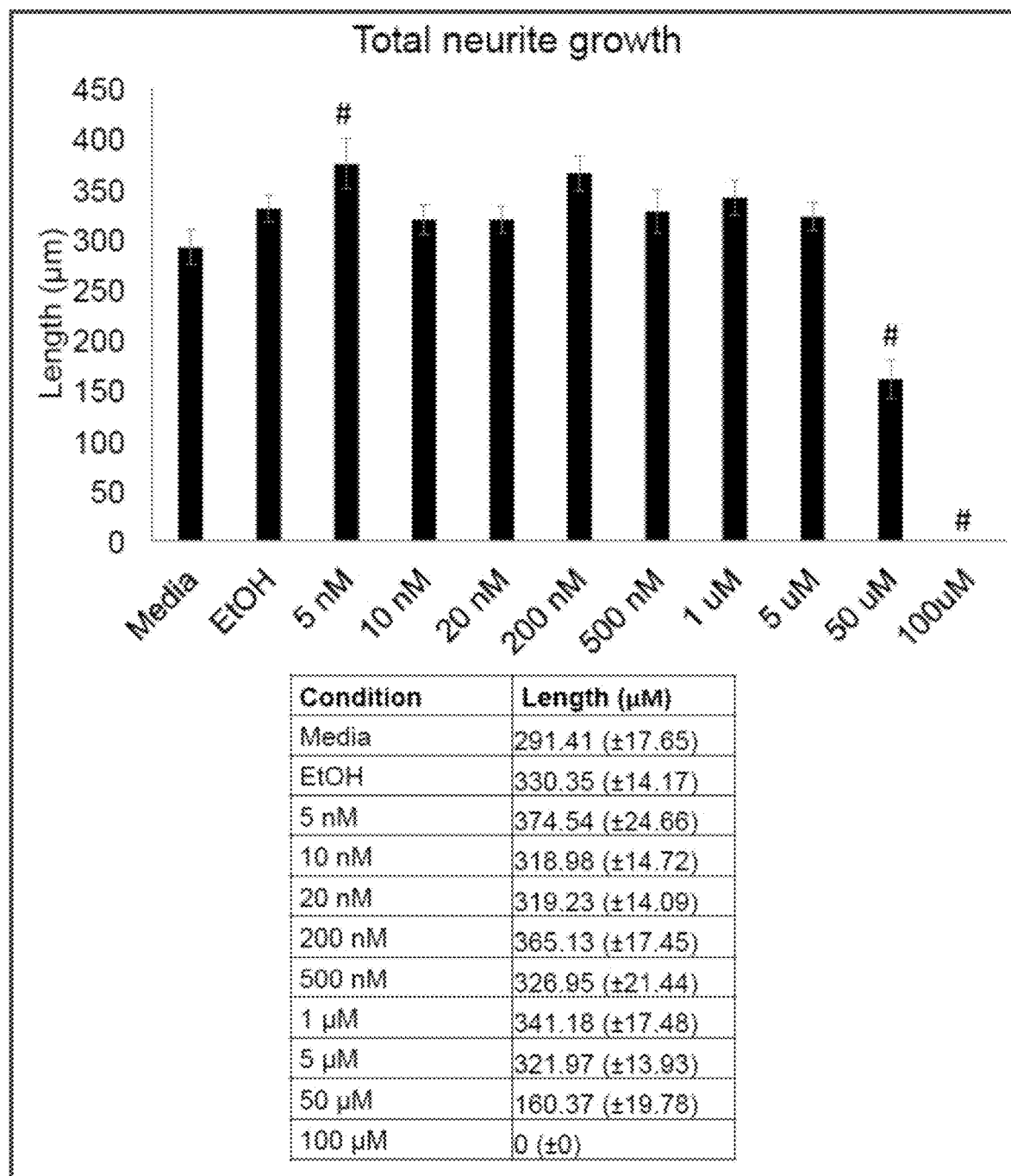

Tacrolimus and RGC neurite growth and branching. To determine the effects of tacrolimus on RGC neurite growth and architecture, RGCs were cultured as above and based on total and longest neurite, the presumptive axon growth and branching were analyzed after 3 DIV (FIGS. 2A-2B). Total neurite growth, which includes axons and dendrites, was optimal at 5 µM. Tacrolimus at 50 µM and 100 µM significantly decreased neurite growth as compared to all other conditions, including media control (FIG. 2B). Thus, total neurite growth response did not follow a typical dose-response relationship. Instead, an optimal therapeutic concentration "window" appears to increase total neurite growth. Analysis of the longest neurite or axon, showed that axon growth was increased without a change in branching. Thus, 90% of the increase in total neurite growth was manifested in axon growth. These data suggest a therapeutic window exists that optimally increases primary axon growth in RGCs.

Figure 3A:
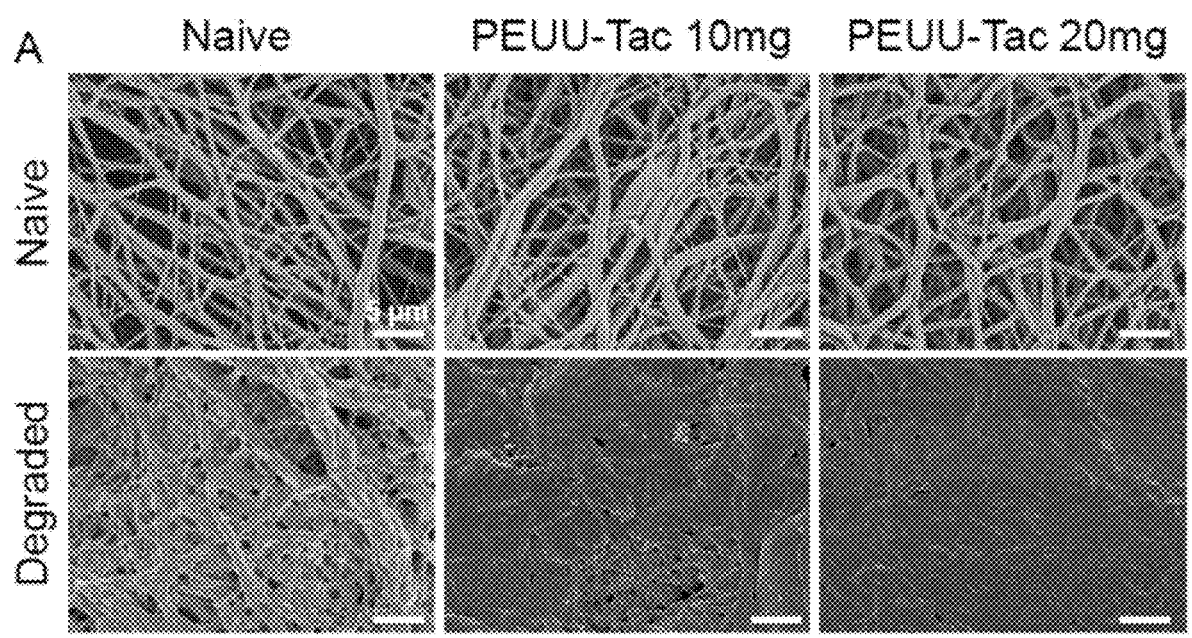

Electrospun PEUU and PEUU-Tac matrices. To construct a tacrolimus releasing matrix, an electrospinning protocol for PEUU (Stankus, Guan et al. 2004) was extended by blending either 10 or 20 mg of tacrolimus and 450 mg of PEUU prior to electrospinning. Macroscopically, PEUU and 10 or 20 mg loaded PEUU-Tac matrices are off-white, pliable sheets indistinguishable from one another as reported previously (Stankus, Guan et al. 2004). Microscopically, PEUU polymer fiber size and organization were also similar. In both PEUU and PEUU-Tac matrices, scanning electron microscopy (SEM) revealed polymer fibers that varied in diameter (FIG. 3A). However, the mean fiber diameter was similar in all three matrices: Unloaded PEUU fibers were 510±130 nm in diameter and 10 or 20 mg loaded PEUU-Tac fibers averaged 560±210 nm in diameter and 560±160 nm in diameter, respectively. Thus, tacrolimus loading does not alter the gross organization of PEUU matrices.

Figure 3B:
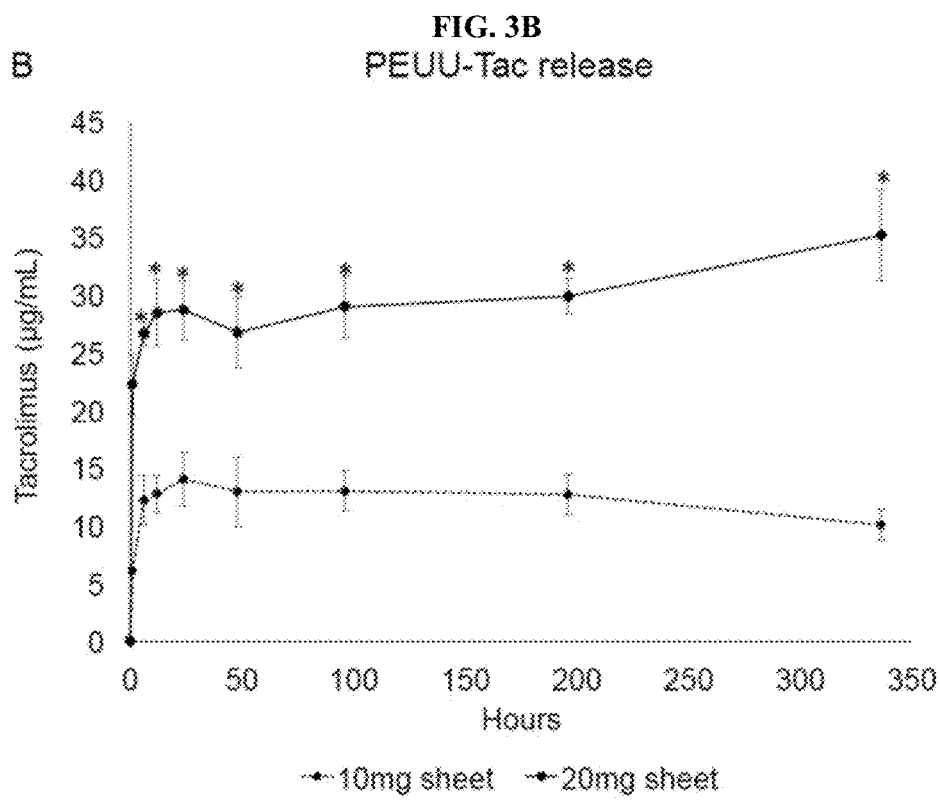

PEUU-Tac tacrolimus release kinetics. Analysis of the tacrolimus release kinetics, showed that both the 10 and the 20 mg PEUU-Tac matrices released tacrolimus at similar rates to a final concentration proportional to their loading concentration (FIG. 3B). Tacrolimus-PEUU sheets loaded with 20 mg released twice the amount of tacrolimus over 14 days as compared to PEUU sheets loaded with 10 mg tacrolimus. The 10 mg PEUU-Tac matrix yielded a concentration of 11.56 µg/mL of tacrolimus within the first 24 hours and this concentration was sustained in the media for 14 days, with a final concentration of 9.53 µg/mL at 14 days. The 20 mg matrix released tacrolimus similarly, yielding a concentration of 20.38 µg/mL tacrolimus in the media after 24 hours and a final concentration of 23.68 µg/mL at 14 days. Thus, both 10 and 20 mg loaded PEUU-Tac matrices release tacrolimus similarly in vitro with a maximum concentration reached by 24 hours.

Figure 3C:
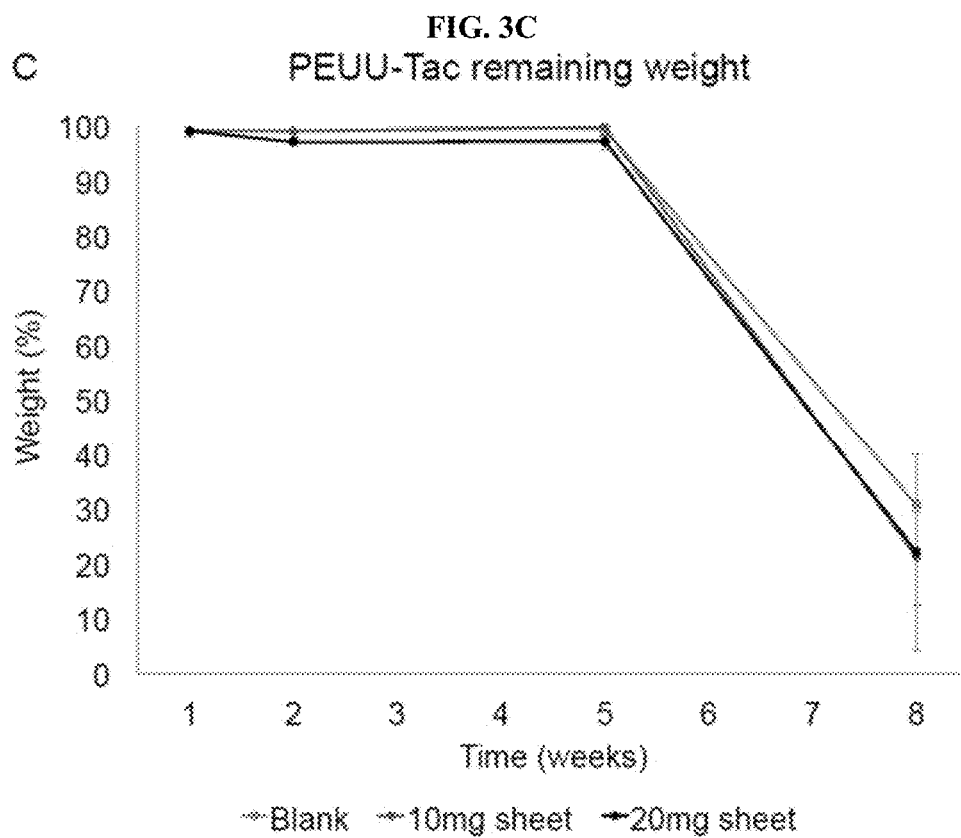

PEUU and PEUU-Tac degradation rates. To determine if tacrolimus loading alters the degradation rate of PEUU matrices, the percent change in mass of unloaded PEUU and 10 or 20 mg loaded PEUU-Tac matrices were analyzed over eight weeks (Hong, Guan et al. 2010). Changes in mass followed a similar profile for all three matrices (FIG. 3C). At 1, 2, and 5 weeks, the mass was largely unchanged. However, by eight weeks the mass decreased similarly and significantly in all three matrices. Unloaded PEUU matrix was reduced to 30.67±1.06% and PEUU-Tac 10 and 20 mg tacrolimus loaded matrices were reduced to 21.30±8.94% and 22.15±17.82%, respectively. In contrast to mass, time-dependent changes in fiber morphology differed with tacrolimus loading. At eight weeks, SEM showed obvious polymeric fibers in PEUU but not in PEUU-Tac matrices (FIG. 3A). Thus, although differences in mass were undetected, the qualitative data indicate that tacrolimus loading leads to a more rapid loss in polymeric fiber architecture during degradation.

Figure 4A:
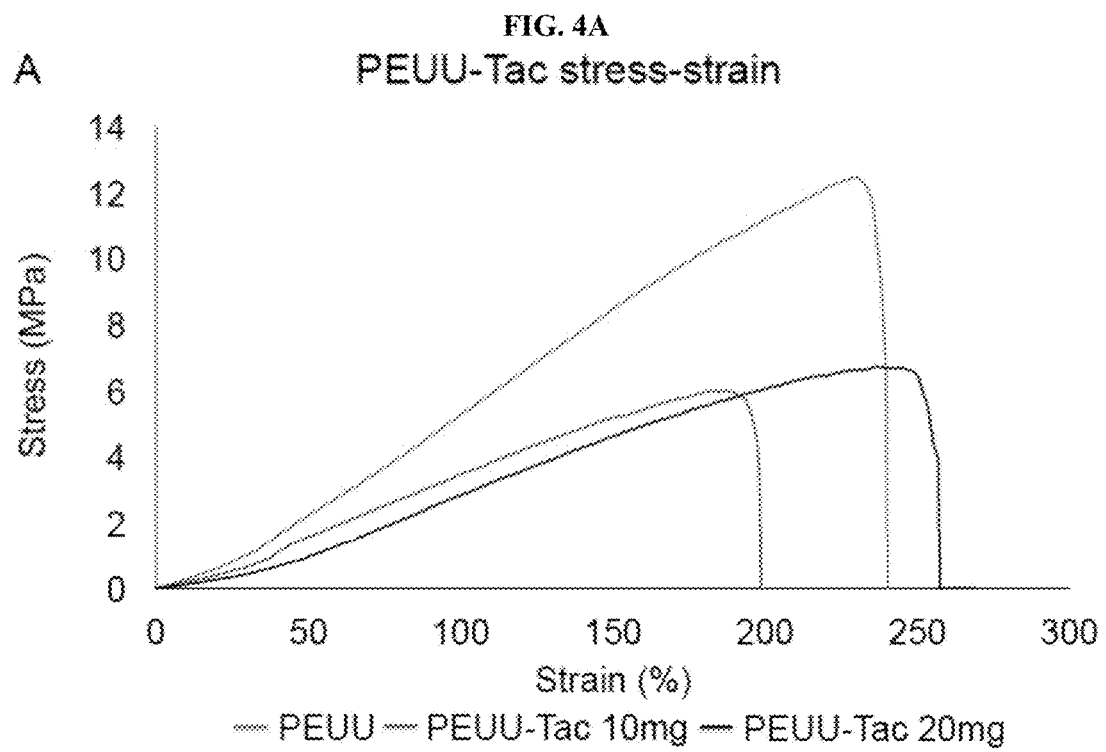
Figure 4B:
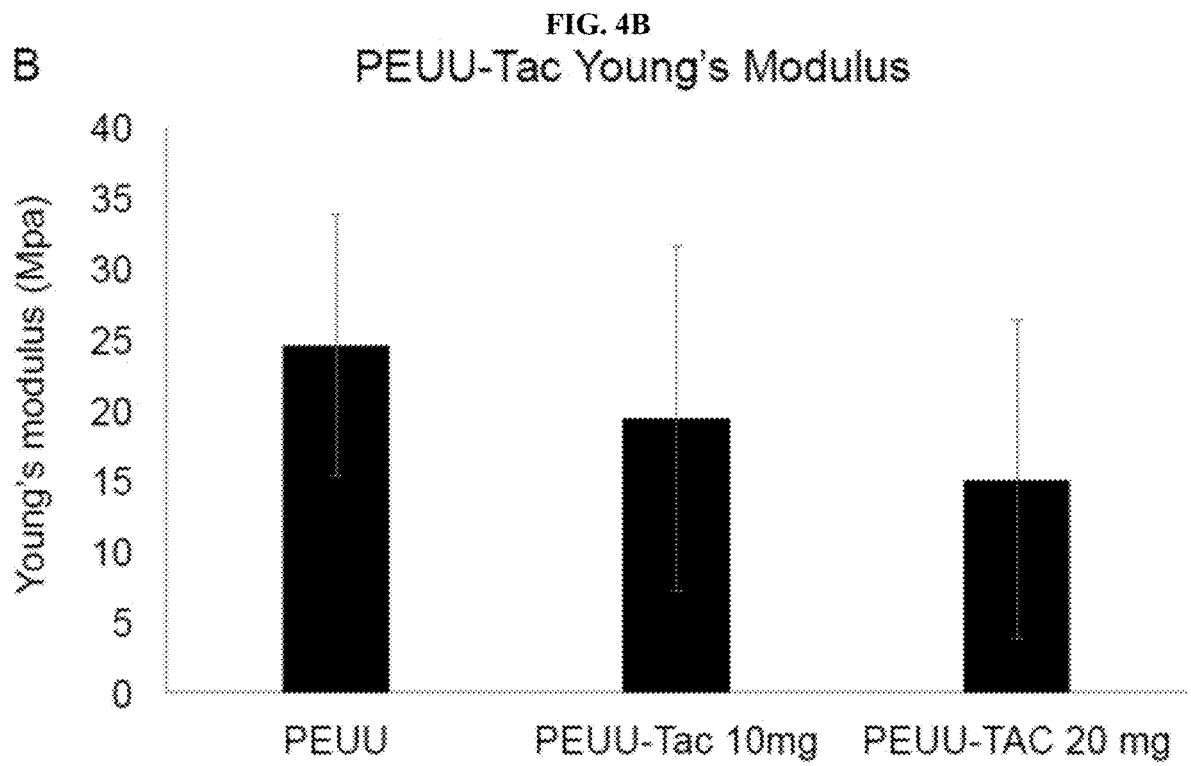
Figure 4C:
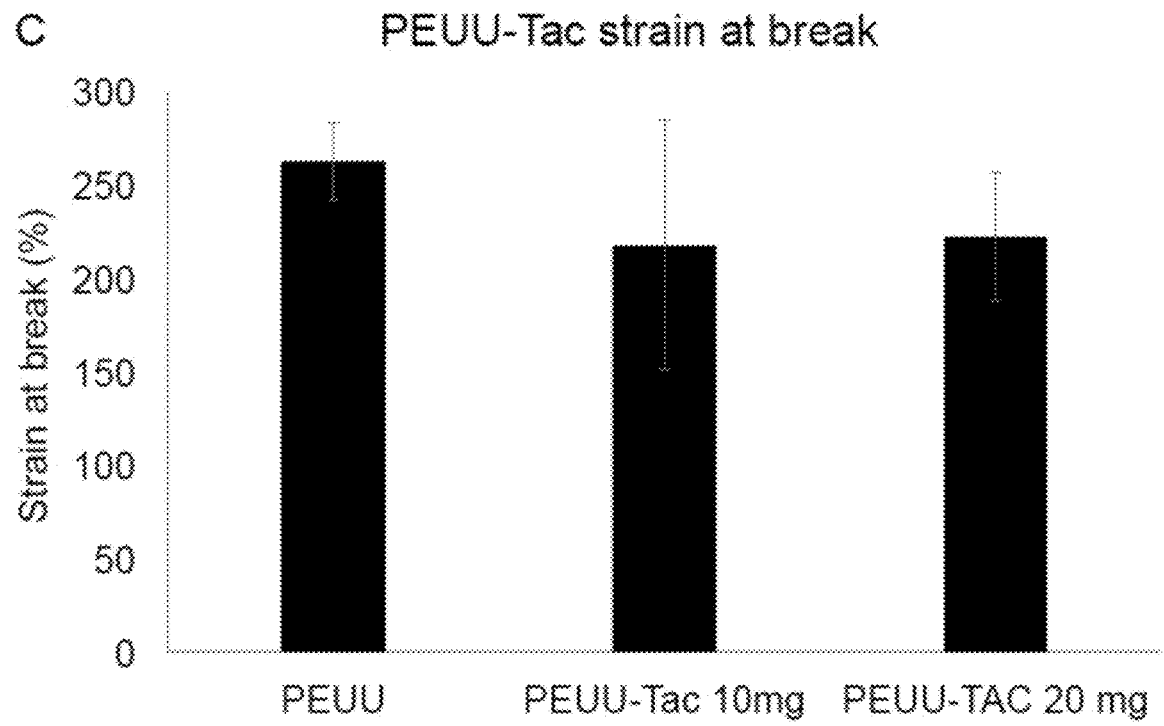
Figure 4D:
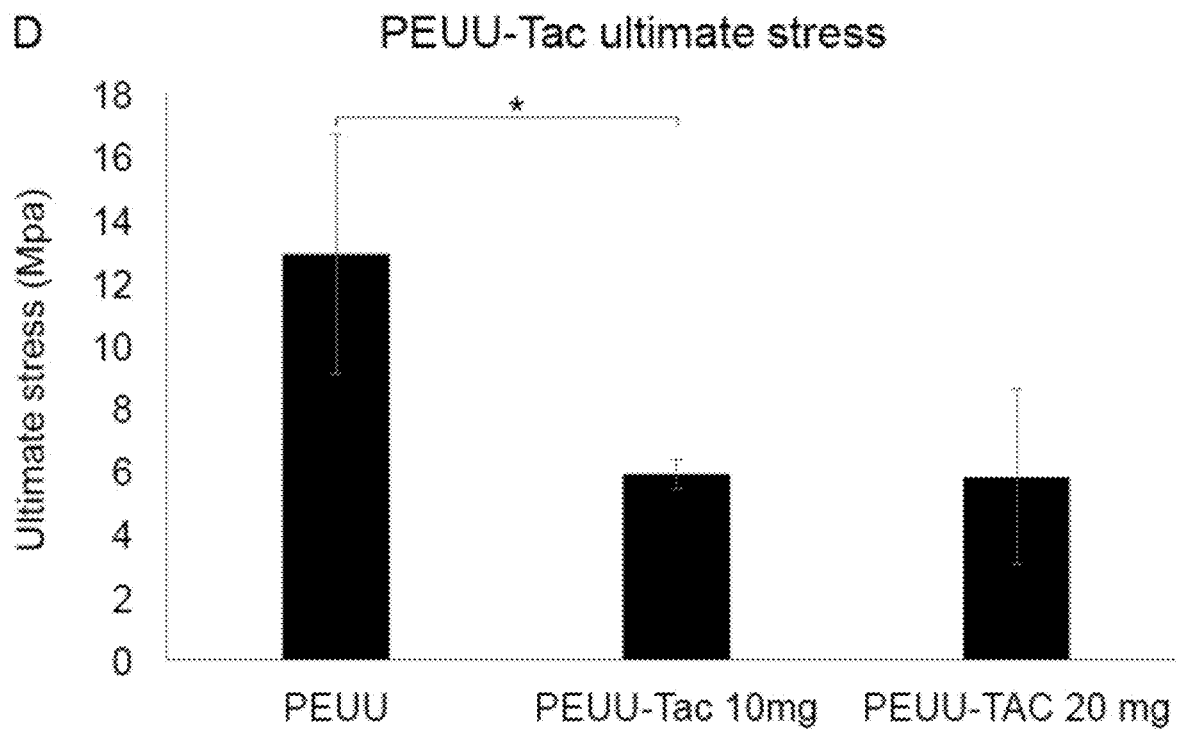

PEUU-Tac mechanical properties. The stress-strain relationship, Young's modulus, ultimate stress, and strain at break were calculated for the PEUU and 10 and 20 mg PEUU-Tac matrices (FIGS. 4A-4D). The stress-strain relationship is shown for each PEUU device (FIG. 4A). Analysis showed tacrolimus loading did not significantly change Young's modulus. Unloaded PEUU was 24.5±9.24 MPa, 10 mg PEUU-Tac was 19.35±12.21 MPa, and 20 mg PEUU-Tac was 15.02±11.29 MPa (FIG. 4B). Ultimate stress was reduced significantly in tacrolimus loaded PEUU matrices compared to the unloaded matrix; PEUU was measured at 12.90±3.81 MPa, PEUU-Tac 10 mg at 5.89±0.47 MPa, and PEUU-Tac 20 mg at 5.80±2.79 MPa (FIG. 3C). However, no significant difference in strain at break was observed between the PEUU (262.33±20.70%), 10 mg (217.33±66.83%), and 20 mg (221.93±34.47%) matrices (FIG. 3D). These results show that tacrolimus loading altered some but not all of the analyzed mechanical properties. However, these changes did not appear to alter the release kinetics nor the scaffold degradation rate.

Figure 5A:
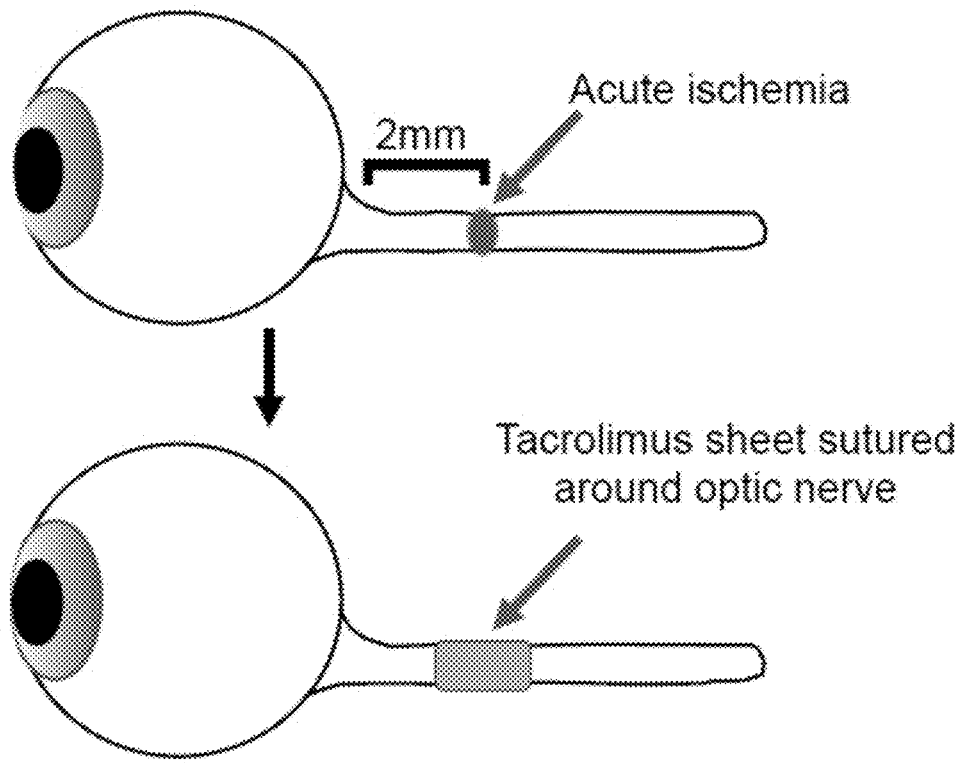
Figure 5B:
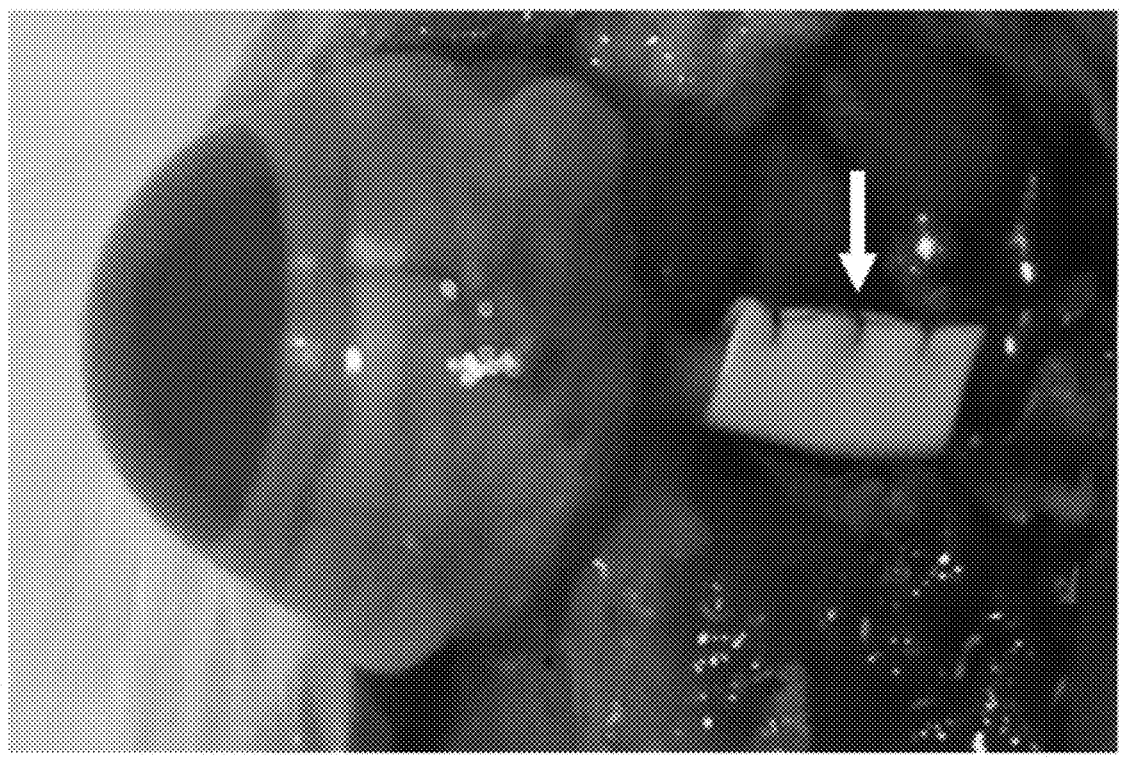
Figure 6A:
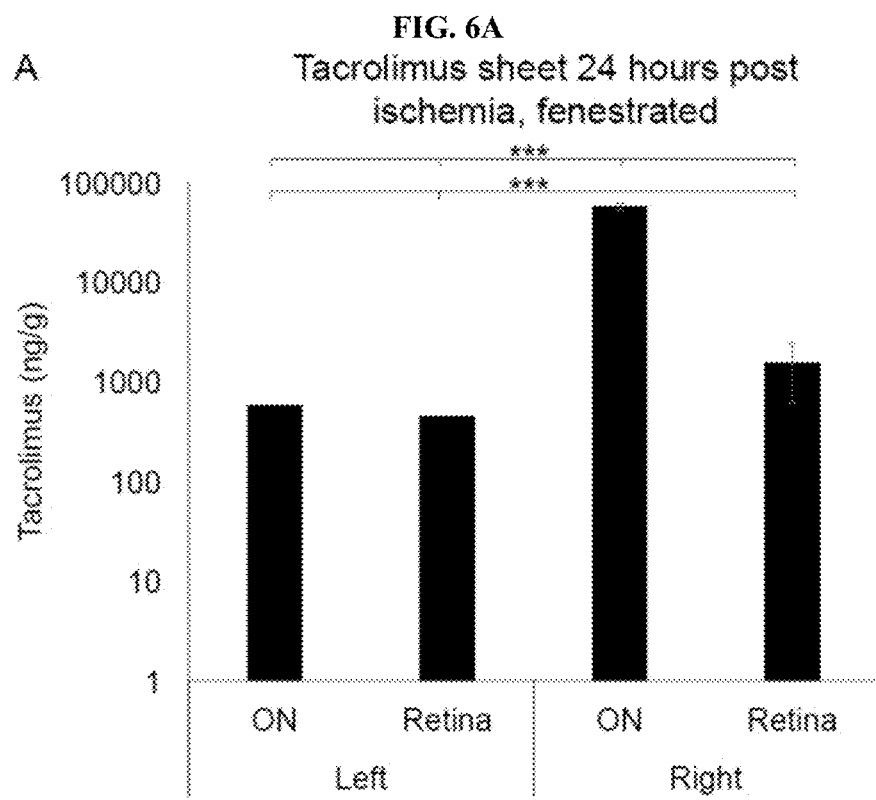
Figure 6B:
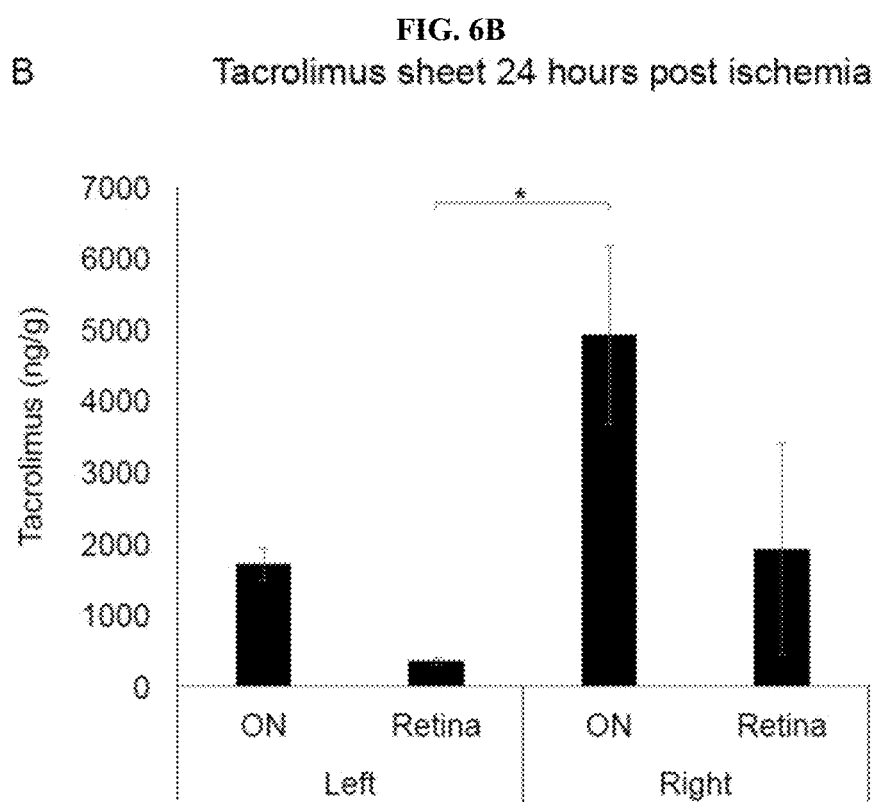

In vivo blood and tissue tacrolimus levels. Tacrolimus retina and optic nerve concentrations were analyzed at 24 hours after suturing PEUU-Tac matrices around injured or uninjured optic nerves with or without fenestration (FIGS. 5A-5B). For all animals, the right optic nerve was injured and/or treated with PEUU-Tac matrices. As shown in FIG. 5A, the clamping was done 2 mm behind the globe of the eye and held for 10 seconds. A 5 mm×1 mm tacrolimus-PEUU sheet was sutured around the optic nerve immediately after the clamping. In fenestrated optic nerves, tacrolimus was detected at therapeutic levels or greater in both retinas and both optic nerves. For example, in the fenestrated optic nerve, tacrolimus was detected at approximately 56 µg/g, resulting in a significantly higher tacrolimus concentration in the right optic nerve compared to the left optic nerve and left and right retinas (FIG. 6A). Additionally, the concentration was significantly higher in the ipsilateral retina (1.5 µg/g), which was significantly higher than the contralateral retina (438 ng/g) and optic nerve (569 ng/g) (FIG. 6A). In contrast, tacrolimus in the wrapped, unfenestrated nerve was approximately 5 ng/g, significantly less than in the fenestrated nerve (FIG. 6B). In the ipsilateral retina, tacrolimus was not significantly different than the optic nerve at 1.9 µg/g, whereas the contralateral retina and optic nerve were 341 ng/g and 1.7 µg/g respectively (FIG. 6B).

Figure 6C:
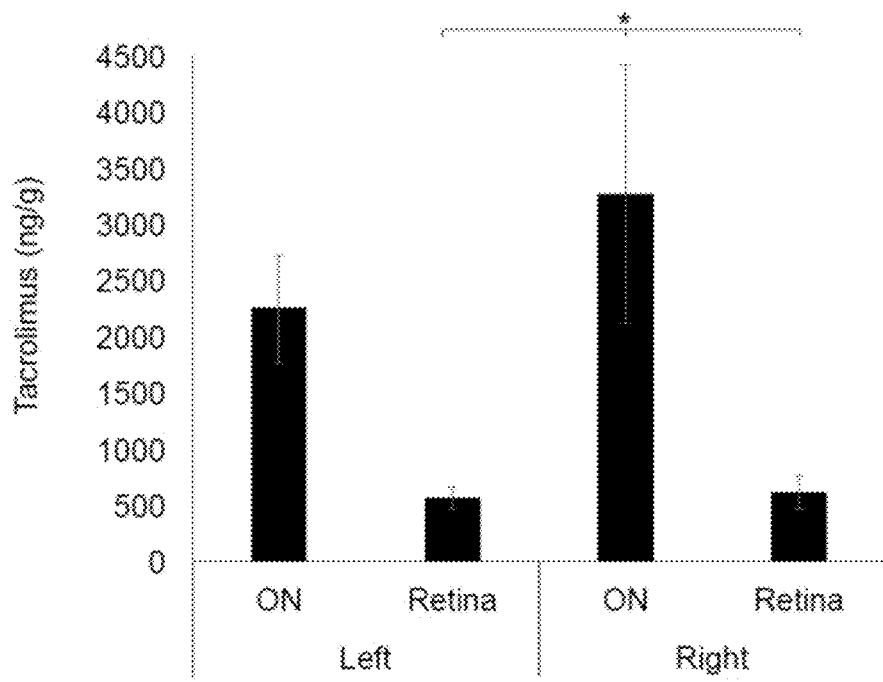
Figure 6D:
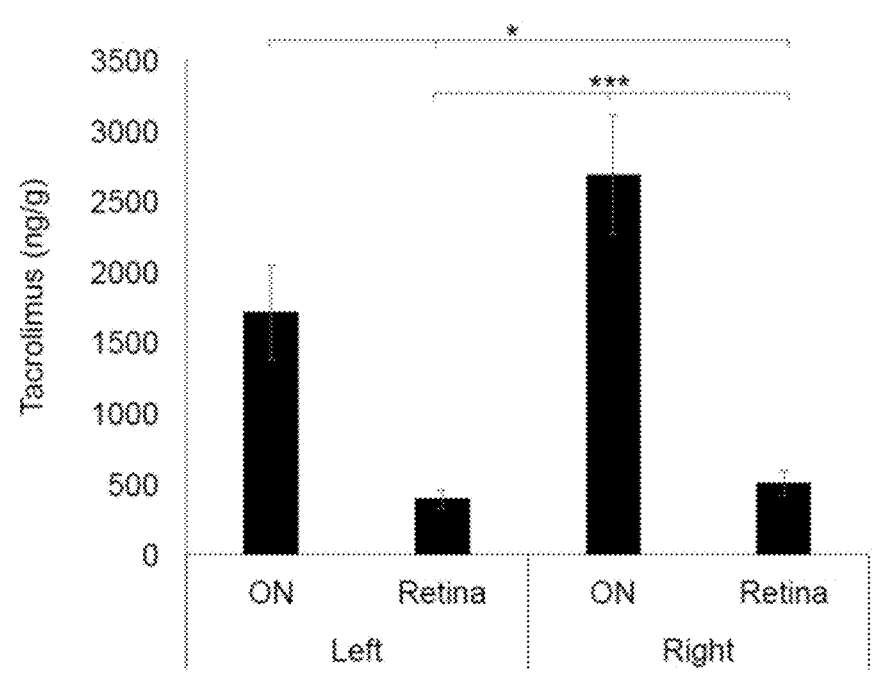
Figure 6E:
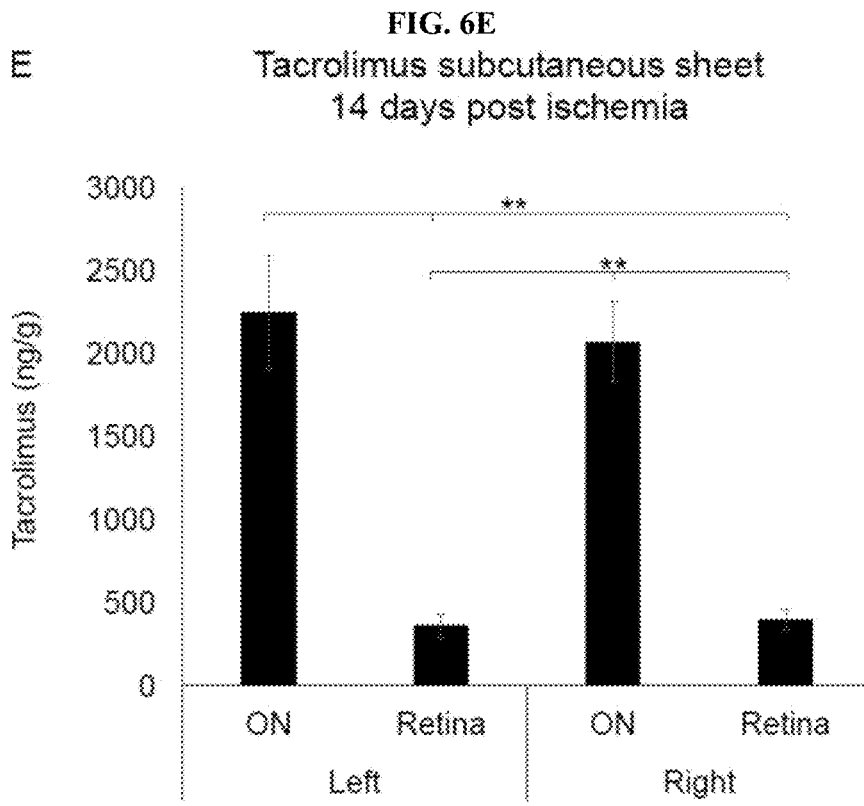
Figure 6F:
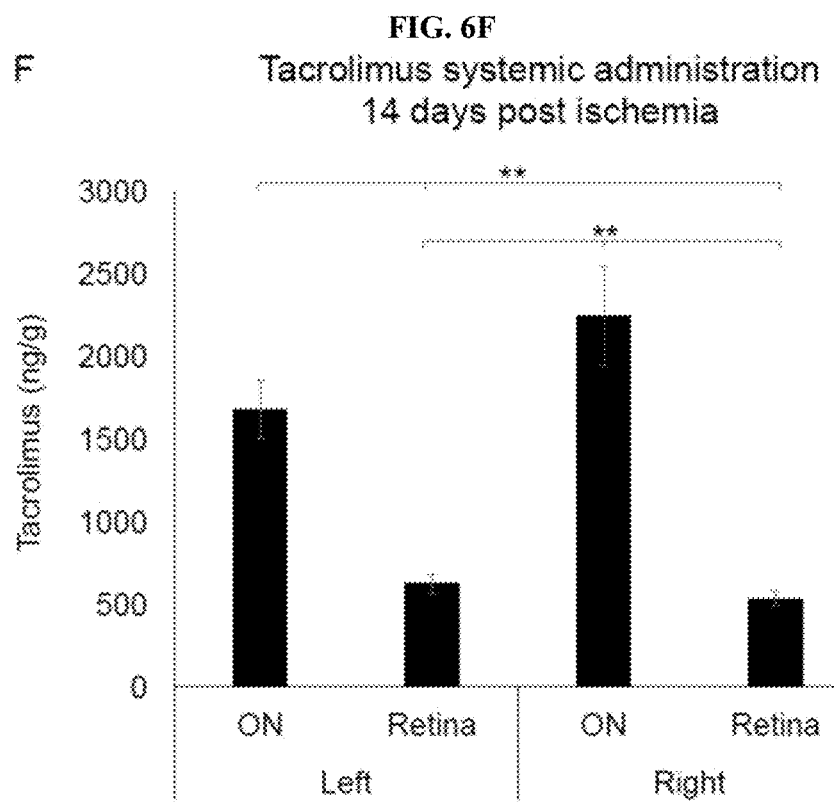

At 14 days post implantation, tacrolimus was measured at 3.3 µg/g in the right optic nerve and 609 ng/g in the right retina (FIG. 6C). In the left optic nerve, tacrolimus was measured at 559 ng/g in the retina and 2.2 µg/g in the optic nerve (FIG. 6C). Thus, in the unfenestrated optic nerve, tacrolimus levels were significantly higher in the right optic nerve as compared to both retinas. However, tacrolimus concentrations were not significantly different between retinas or optic nerves. Tacrolimus in the uninjured optic nerve had similar results after 14 days, with the optic nerves having significantly greater tacrolimus concentration as compared to the corresponding retinas (FIG. 6D). The wrapped optic nerve had a tacrolimus concentration of 2.7 µg/g, and the contralateral optic nerve showed a concentration of 1.7 µg/g. The tacrolimus concentration in the retinas was significantly lower, with the ipsilateral and contralateral retinas showing concentrations of 499 ng/g and 387 ng/g, respectively. After subcutaneous PEUU-Tac implantation, tacrolimus concentrations were similar in the both optic nerves and retinas at 2.1 µg/g in the right optic nerve and 2.2 µg/g in the left optic nerve and 389 ng/g in the right retina and 352 ng/g in the left retina (FIG. 6E). Thus, the right and left optic nerves had significantly higher tacrolimus concentrations as compared to the left and right retinas. After systemic tacrolimus injection of 2.2 mg/kg/day, tacrolimus concentrations were also similar to subcutaneous PEUU-Tac implantation at 2.2 µg/g in the right optic nerve and 1.7 µg/g in the left optic nerve, and 530 ng/g in the right retina and 618 ng/g in the left retina (FIG. 6F). The right and left optic nerves had significantly higher tacrolimus concentrations compared to the left and right retinas. Thus, tacrolimus tissue concentrations in the optic nerve and in the retina are in line with the desired therapeutic concentrations. However, tacrolimus concentration in the optic nerve and in the retina appear to be independent of the location or the method of administration.

Despite similar tissue levels regardless of the location or the method of administration, blood levels of tacrolimus were significantly reduced (FIGS. 7A-7C). At both 24 hours and at 14 days in ischemic optic nerves treated with PEUU-Tac matrices, tacrolimus blood concentrations were undetectable. In uninjured optic nerve nerves, tacrolimus was undetectable in the blood at 24 hours and detected at 0.30±0.10 ng/mL at 14 days. Similarly, in animals receiving subcutaneous PEUU-Tac matrices blood concentrations were undetectable at 24 hours and detected at 0.26±0.12 ng/mL at 14 days. Thus, the blood levels in both the optic nerve and the subcutaneous PEUU-Tac matrix treated animals are well below typical therapeutic trough levels, which range from 10-20 ng/g. In contrast, systemic blood levels were measured at 7.05±1.09 ng/mL at 24 hour and 27.66±3.53 ng/mL at 14 days (FIGS. 7B-7C). Thus, despite similar tacrolimus concentrations in the retina and in the optic nerve, the tacrolimus concentration in the blood was significantly higher following systemic administration as compared to the tacrolimus-PEUU sheet application around the optic nerve or subcutaneous implantation. These data suggest that tacrolimus accumulates in the retina and, to a greater degree, in the optic nerve.

Next, the effects of tacrolimus on astrocyte activation were analyzed in vivo after 14 days (FIGS. 8A-8B). After optic crush, quantification of GFAP expression showed a significant increase in GFAP expression (FIG. 8A). In contrast, and consistent with the suppression of glial activation reported in in vitro studies, GFAP expression in PEUU-Tac treated nerves was similar to uninjured and systemically treated nerves (FIG. 8A). Similarly, treatment with tacrolimus wrap and systemic tacrolimus treatment after optic nerve crush did not cause significant GFAP expression as compared to uncrushed controls (FIG. 8B).

Figure 9A:
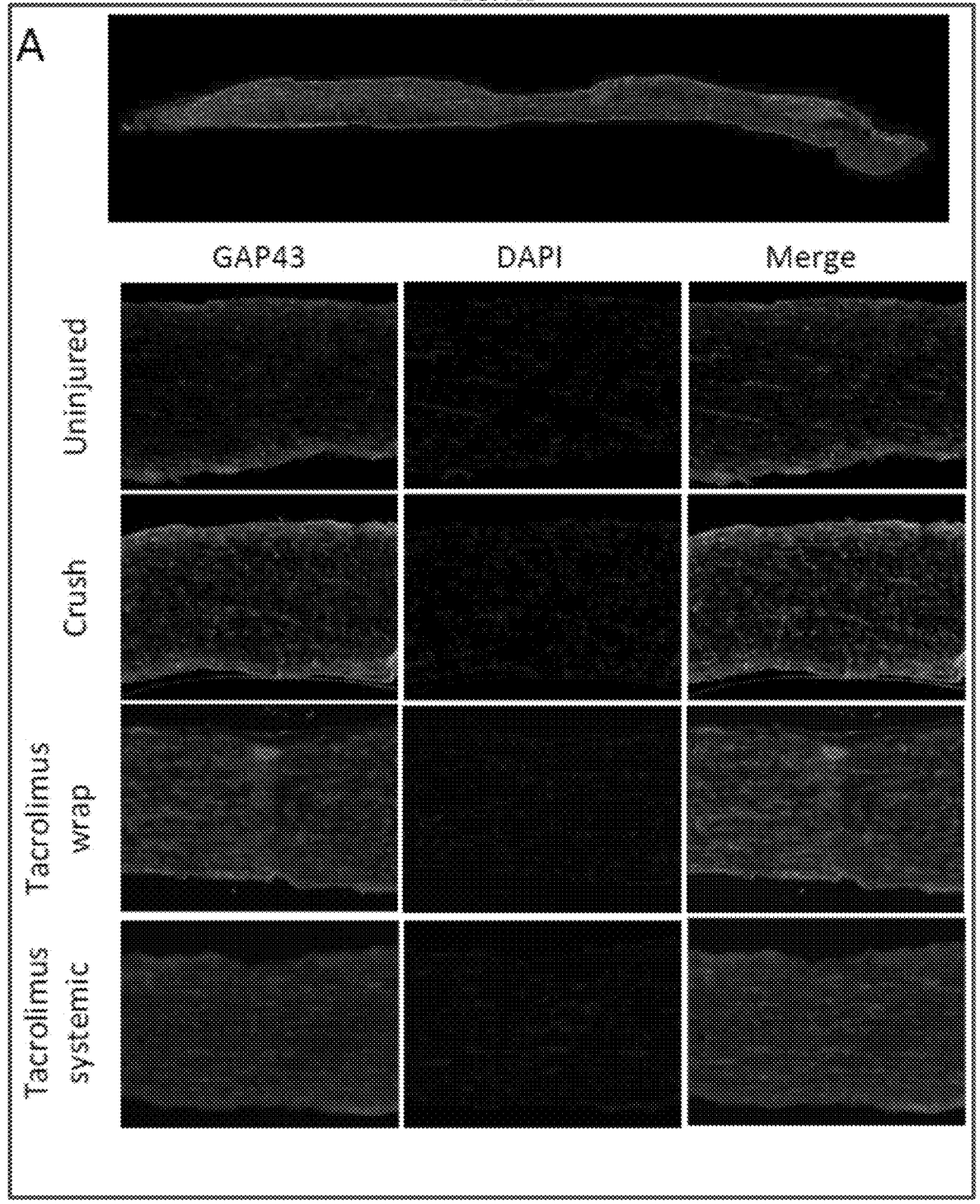
Figure 9B:
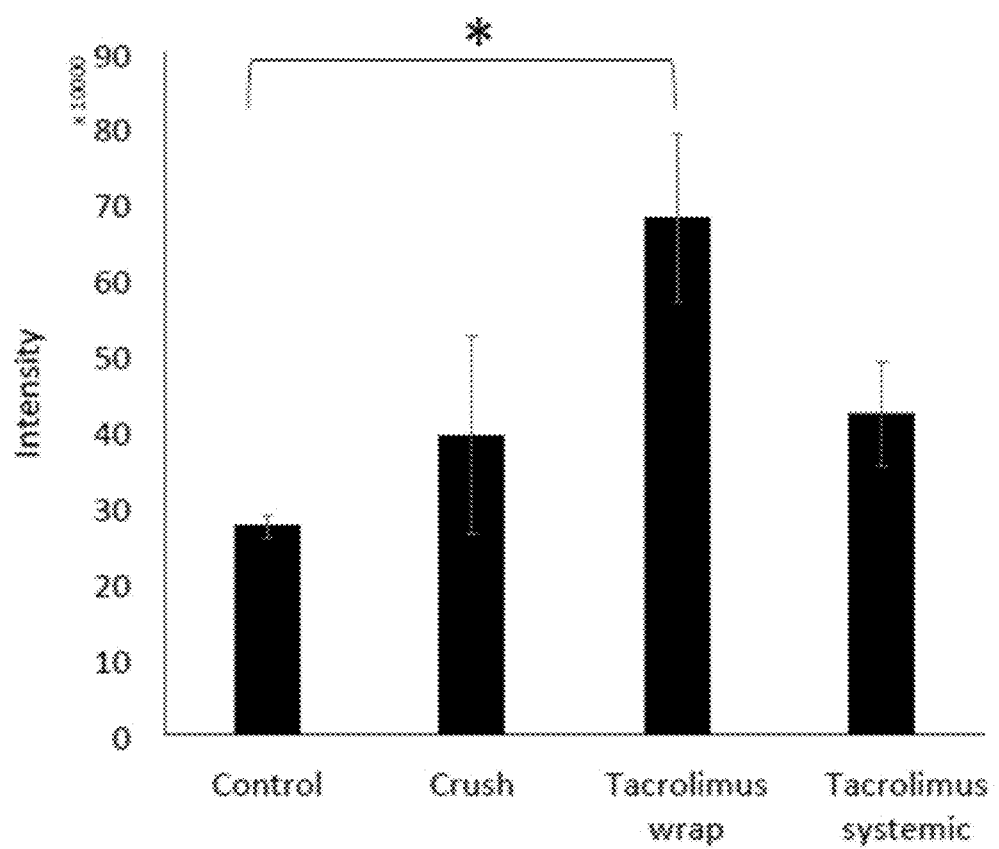

Finally, PEUU-Tac was studied to determine whether it altered the expression of the axon growth marker GAP-43 (FIGS. 9A-9B). Consistent with previous studies administering tacrolimus systemically, local tacrolimus administration increased GAP-43 expression in the optic nerve in a manner consistent with retinal axon growth (FIG. 9A). Interestingly, PEUU-Tac increased GAP-43 expression in the optic nerve to levels above systemically treated animals (FIG. 9B).

Discussion

This Example demonstrates that an electrospun tacrolimus-PEUU sheet is able to sustainably and locally release tacrolimus. Two tacrolimus-PEUU sheets were fabricated, one with 10 mg tacrolimus total, and another with 20 mg tacrolimus total, and both tacrolimus-PEUU sheets sustainably released tacrolimus for up to 14 days. In current clinical applications, systemic tacrolimus is administered frequently and the presently disclosed tacrolimus-PEUU sheet is able to achieve a sustained release of tacrolimus, which eliminates the need for repeated systemic doses of tacrolimus.

The addition of tacrolimus to the PEUU sheets did not alter the degradation properties of the material. The sheets maintained their mass for up to 5 weeks after the onset of the degradation study, suggesting that the sheets are able to maintain their form and support for an extended period of time in vivo. Importantly, it was found that PEUU did not induce cellular toxicity, necrosis, abnormal growth, or inflammation, and therefore can be a suitable drug delivery vehicle for treating both PNS and CNS nerve injuries.

In vitro studies were conducted to examine the effects of tacrolimus on RGCs. High dosages of tacrolimus can have fatal side-effects, including liver and kidney toxicity (Randhawa, Starzl et al. 1997), and therefore the survival of RGC survival in culture was studied. The live/dead study demonstrated that the dosage of tacrolimus had no significant effect on neuron survival. Neurite outgrowth was assessed by analyzing the total neurite length, longest neurite length, and branching of the isolated primary RGCs. In the assays with RGCs only, tacrolimus significantly increased total and longest neurite growth; however in the assays with RGCs and microglia, tacrolimus did not show an increase in axonal outgrowth, suggesting that tacrolimus acting on the neurons themselves was responsible for the observed increases. Tacrolimus has been shown in other systems to act directly on neuronal calcineurin inhibition (Klettner and Herdegen 2003).

In the in vivo studies, the tacrolimus sheet localized the release of tacrolimus into the optic nerve where it was applied, with negligible amounts of tacrolimus in the ipsilateral retina and contralateral optic nerve and retina. The negligible amounts of tacrolimus in the ipsilateral retina and contralateral tissues emphasizes the ability of the sheet to deliver tacrolimus locally and has a number of advantages for treating nerve injuries, including the use of lower amounts of tacrolimus than would be needed with systemic administration. The sustained release of the compound indicates that a single sheet application can be sufficient to treat nerve injury where systemic administration requires frequent injections to maintain the same level of tacrolimus, which would greatly reduce the chance of nephrotoxicity and neurotoxicity. In cases where high levels of tacrolimus were maintained in the blood for an extended period of time, elevated serum creatine, tremor, diarrhea, and hyperglycemia have been reported (Mayer, Dmitrewski et al. 1997).

Preliminary histology data suggests that the tacrolimus decreases inflammation and increases RGC axon growth 14 days after optic nerve crush, as indicated by a decrease in astrocyte activation and an increase in GAP-43 positive staining, which is a marker for axon regeneration.

Example 2: In Vitro and In Vivo Effects of Device for Local Delivery of Tacrolimus on Mystacial Tissue in Rats This Example illustrates the use of a biodegradable matrix for local delivery of tacrolimus. Two wraps were fabricated using poly(ester urethane) urea (PEUU) as a polymer base, and loaded with either 10 mg or 20 mg tacrolimus. The wraps were fabricated by electrospinning to incorporate the tacrolimus into the PEUU wrap.

Figure 10:
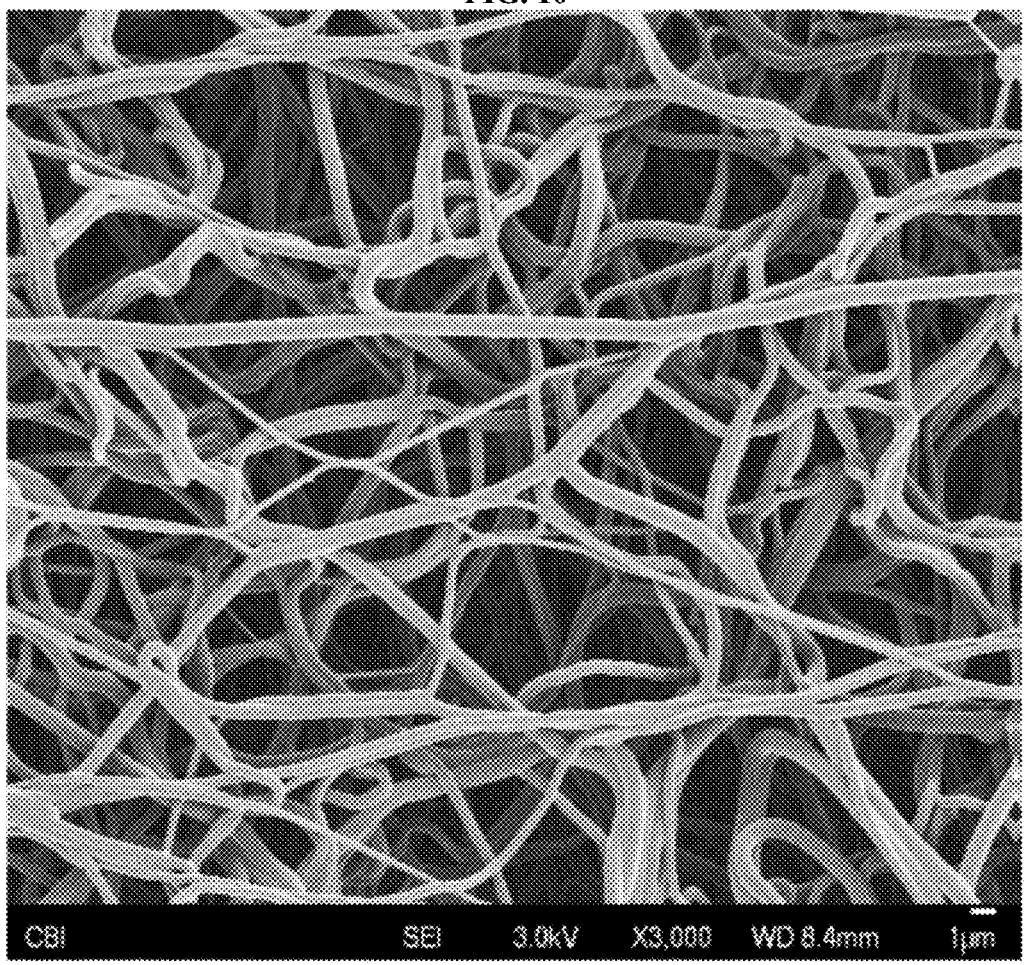

Poly(ester urethane) urea (PEUU) was synthesized from polycaprolactone diol (Mn=2000), 1,4-diisocyanatobutane, and putrescine, as described previously (Guan, Sacks, et al. 2002). Two separate scaffolds containing tacrolimus were fabricated by electrospinning. Briefly, 10 mg or 20 mg of tacrolimus was dissolved in 608 μL DMSO to yield a 20 mM or 40 mM solution, respectively. The tacrolimus solution was mixed with 0.45 g PEUU, which was dissolved in 1,1,1,3,3,3-hexafluoroisopropanol (HFIP) at a concentration of 12% (w/v), and electrospun onto a rotating and translating stainless steel mandrel (19 mm diameter) by feeding through a charged capillary at a rate of 1.5 mL/h. The mandrel was located 17 cm from the tip of the capillary. The voltage between the capillary and mandrel was 19 kV. The wraps were sterilized under UV light overnight and then with ethylene oxide (EtO) before use. FIG. 10 shows a representative scanning electron microscopy (SEM) image of the 10 mg wrap.

In Vitro Release Kinetics

Six 50 mL glass beakers were coated with Sigmacote (Sigma, St. Louis, Mo.) to minimize absorption of the FK506 binding protein onto the surface of the glass beaker during the assay. As tacrolimus is poorly soluble in PBS, a solution of 0.5% Cremephor EL (Sigma, St. Louis, Mo.) in 1×PBS was used as release media for the release study. Three sections of each of the PEUU-Tac scaffolds were placed in 25 mL of 0.5% Cremephor EL solution in coated beakers with gentle agitation (90 RPM). 300 μL of the release media was collected at different time points and replaced with fresh media. Time points for collection for the media were 1, 2, 4, 8, 12 hours, and 3, 7, 14, 21, 28 days after start of the experiment. The concentration of tacrolimus in the respective samples was measured using HPLC.

Figure 11:
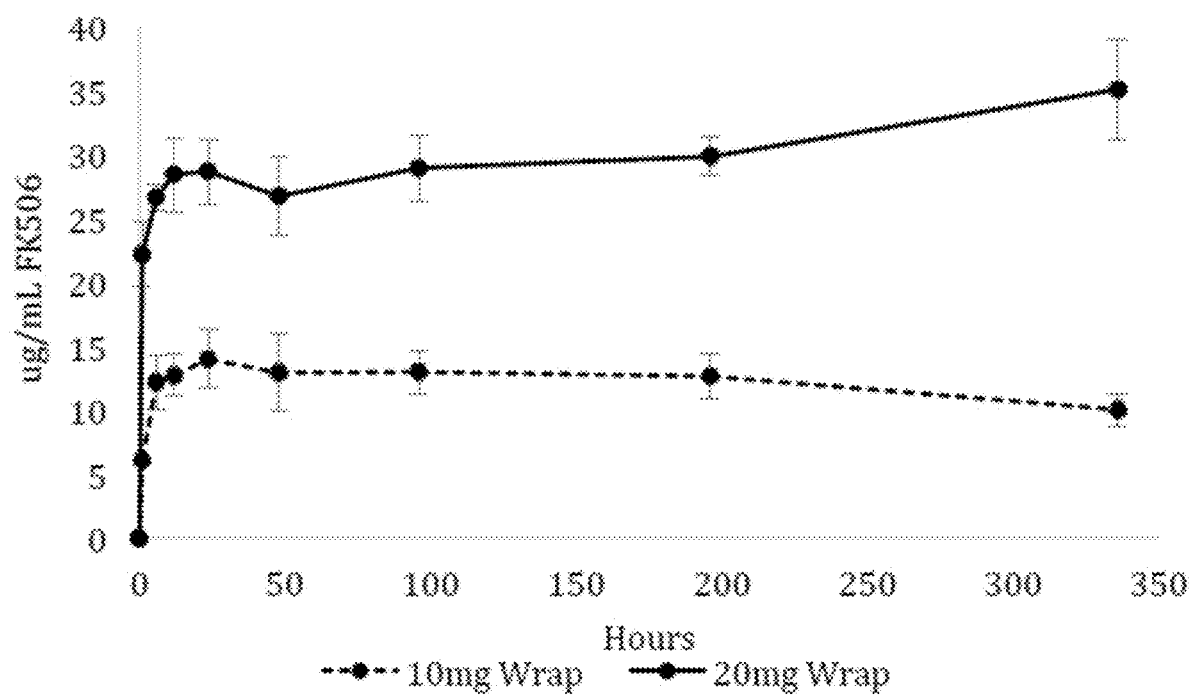
FIG. 11 shows the release profile for 10 mg and 20 mg tacrolimus wraps over two weeks, as described in Example 2.

In vitro data showed that both the 10 mg and 20 mg wraps have an initial burst release, proportional to their loading. The 10 mg wrap released tacrolimus to yield a concentration of 14 µg/mL tacrolimus within the first 24 hours and this concentration was sustained in the media for 2 weeks, with a concentration of 10.03 µg/mL at the final time point. The 20 mg wrap followed a similar profile, releasing tacrolimus to yield a concentration of 28.6 µg/mL in the media after 24 hours. The 20 mg wrap continued to release tacrolimus over time, with a concentration of 35.1 µg/mL at the final time point (FIG. 11).

In Vivo Methods

Animals. All animals received care in compliance with the University of Pittsburgh Institutional Animal Care and Use Committee and followed guidelines from the Guide for the Care and Use of Laboratory Animals published by the National Institutes of Health.

Adult Lewis rats, 8-10 weeks of age (Harlan Sprague-Dawley, Indianapolis, Ind.), were anesthetized with 50 mg/kg of pentobarbital sodium (i.p.) supplemented, as needed, with 10/mg/kg injections. Surgeries were performed using sterile techniques with animals kept on a heating pad to maintain core temperature at 37° C. A small incision was made just proximal to the mystacial (whisker) pad on the left side of the face. Subcutaneous tissue was dissected to expose the infraorbital branch of the trigeminal nerve. The nerve was transected using micro-scissors. The cut ends of the nerve trunk were approximated in their normal anatomical orientation and sutured through the epineurium with 10-0 nylon suture impregnated with 20 mg of tacrolimus. The wound was closed with 5-0 chromic dissolvable sutures. Following recovery from anesthesia the rats were returned to individual cages with a 12-hour light-dark cycle. Rat chow and water were available ad libitum. Nerve transected animals (n=41) were studied electrophysiologically from 3 to 8 weeks post-transection and repair. Ten un-operated animals served as controls.

Trigeminal ganglion cell recordings. Electrophysiological experiments were performed using procedures similar to those described previously (Lee and Simons 2004; Lichtenstein et al. 1990). Rats were anesthetized with isoflurane (1-2%) using a ~1:1 mixture of $O_2$ and $N_2$. A short length of polyethylene tubing was inserted into the trachea as a cannula, the dorsal surface of the skull was exposed, and a steel post for holding the animal's head was fixed to the bone using dental acrylic. During the recording sessions, the head post allowed unimpeded access to the facial whiskers. A stainless steel skull screw for electrical grounding was inserted into the frontal region of the skull. The head was positioned so that the dorsal surface of the skull was parallel to the recording table.

Using a dental drill, a craniotomy was produced on the left side overlying the left trigeminal ganglion at the base of the skull (~2.4 mm anterior to bregma and ~2.6 mm lateral to the midline). Core temperature was maintained at 37° C. using a servo-controlled heating blanket. At the conclusion of the recording session, which typically lasted 10 hours, the animal was euthanatized with an overdose of pentobarbital sodium (>100 mg/kg, i.v.) or isoflurane. In some animals, the nerve was harvested for later histological study.

Single neuron recordings and whisker stimulation. Extracellular recordings of single neurons in the trigeminal ganglion were obtained using varnished coated stainless steel or tungsten microelectrodes (2-4 Mohms at 1000 Hz, Frederick Haer, Brunswick, Me.) that were advanced from the surface of the cortex into the ganglion using a hydraulic stepping-motor driven microdrive. Standard amplification and band-pass filtering (300-10 k Hz) were used for recording action potentials. Spike waveforms, collected at 32 kHz, were parsed on-line according to amplitude criterion and subsequently examined on the basis of principal components using custom spike-sorting software written in LabView (National Instruments, Austin, Tex.). Single units were identified on the basis of spike waveform. Sequential spikes could be recorded at intervals of less than or about 0.53 ms.

The whisker activating the recorded unit, called the Principal Whisker (PW), was first identified using a hand-held probe and audio monitoring. A multi-angle piezoelectric stimulator (Simons 1983) was then attached to the PW 10 mm from the base of the hair. The stimulator was used to deflect the whisker in eight angular directions in 45° increments (0=caudal, 90=dorsal). Stimuli consisted of ramp-and-hold deflections of 125 mm/s onset and offset velocities and plateau durations of 200 ms. Data were collected for a 500 ms period bracketing the stimulus. Each deflection was repeated 80 times, in 10 blocks of 8 randomized directions. A laboratory computer controlled the stimulator and collected the neurophysiological data. Spike waveforms and spike times, along with stimulus information, e.g., deflection angle, were saved to disk.

Infraorbital nerve stimulation and trigeminal ganglion recording. Eleven animals (9 transected, 2 control) were examined to determine conduction speed of the infraorbital nerve. The nerve was exposed a few mm proximal to the mystacial pad and ~20 mm from the trigeminal ganglion. For transected animals the stimulation site was distal to the repair. A bipolar electrode consisting of a pair of Teflon-coated stainless steel wires (0.011 inch outer diameter) spaced ~3 mm apart were positioned to span the width of the nerve. A Grass stimulator and constant current isolator were used to deliver monophasic pulses of 0.05 ms duration at a rate of 0.6 Hz. Recordings of evoked potentials were made with the same microelectrodes used for single-unit recordings. Potentials were band-pass filtered at 300-3 k Hz to reduce the stimulus artifact. Stimulus intensity was adjusted to 2×threshold for eliciting a response; thresholds ranged from 0.65 to 5.5 mA. Using a digital oscilloscope, conduction time was measured from the onset of the stimulus to the initial positive peak of the response. Some of the animals were subsequently studied using whisker stimuli and unit recordings.

Data analyses. Data were analyzed using custom software written in Excel Visual Basic and the Excel add-on statistical package, Analyze-it (Analyse-it Software, LTD). Peristimulus time histograms (PSTHs) having 1 ms bins were constructed from spike times of individual single units. Spike counts for different time epochs were averaged over the 10 trials for each of the 8 deflection directions. Responses to stimulus onsets (ON responses) were calculated during a 20 ms period beginning 1 ms after deflection onset; this epoch captures the initial, transient phase of the whisker evoked response (see FIGS. 12A-12B). Data are presented as mean spikes per stimulus; a response of 1 spike per stimulus corresponds to an average firing rate of 50 Hz. Responses to the sustained phase of the stimulus were calculated over the final 100 ms of the 200 ms steady-state deflection (Plateau responses). Spontaneous activity, which is typically sparse or absent altogether in trigeminal ganglion cells, was measured during a 100 ms epoch preceding stimulus onset averaged over all 8 deflection angles. Responses were classified as "slowly adapting" if the plateau response exceeded spontaneous firing with a confidence limit of 95% (one-tail); all other responses were classified as "rapidly adapting". In whisker follicles slowly adapting responses are thought to be associated with Merkel cells and rapidly adapting responses with lanceolate endings (Gottschaldt and Vahle-Hinz 1981; Lichtenstein et al. 1990; Rice 1985). For interspike interval analyses, spike times were converted to 0.1 ms intervals.

ON response latency was calculated as the time in ms of the first statistically significant bin in the maximal angle PSTH constructed from stimulus onsets. The first bin within the ON response window having a spike count that was statistically larger than spontaneous activity was identified.

Results

Figure 12A:
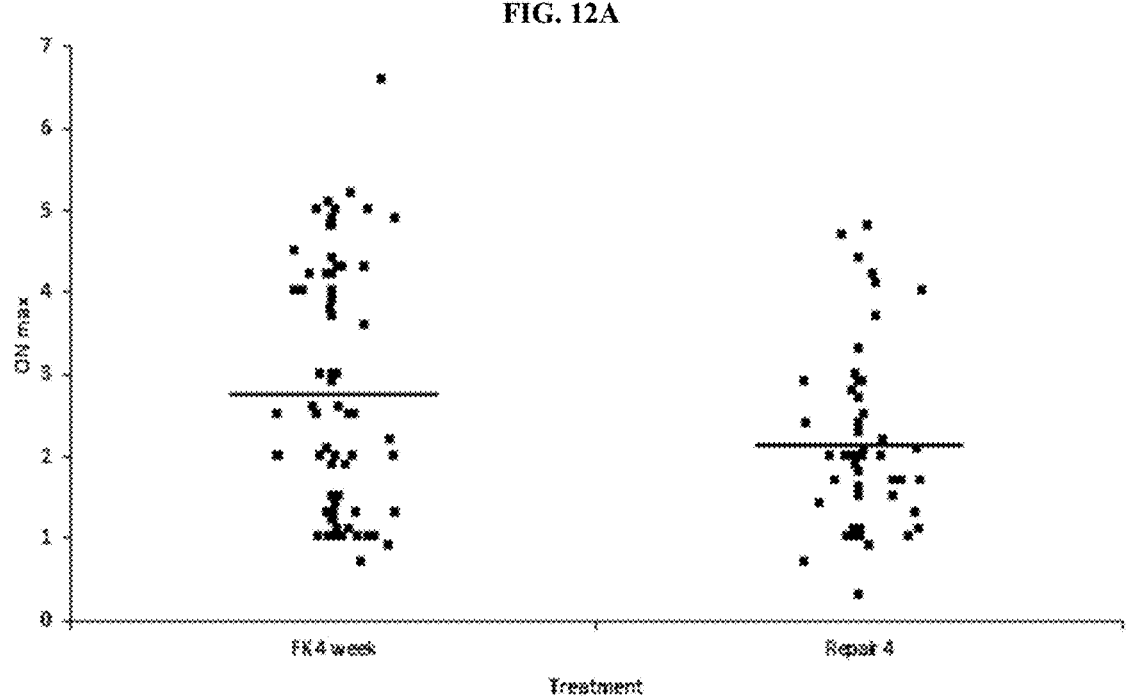
FIGS. 12A-12B show response magnitude at 4 weeks after infraorbital transection and repair.
Figure 12B:
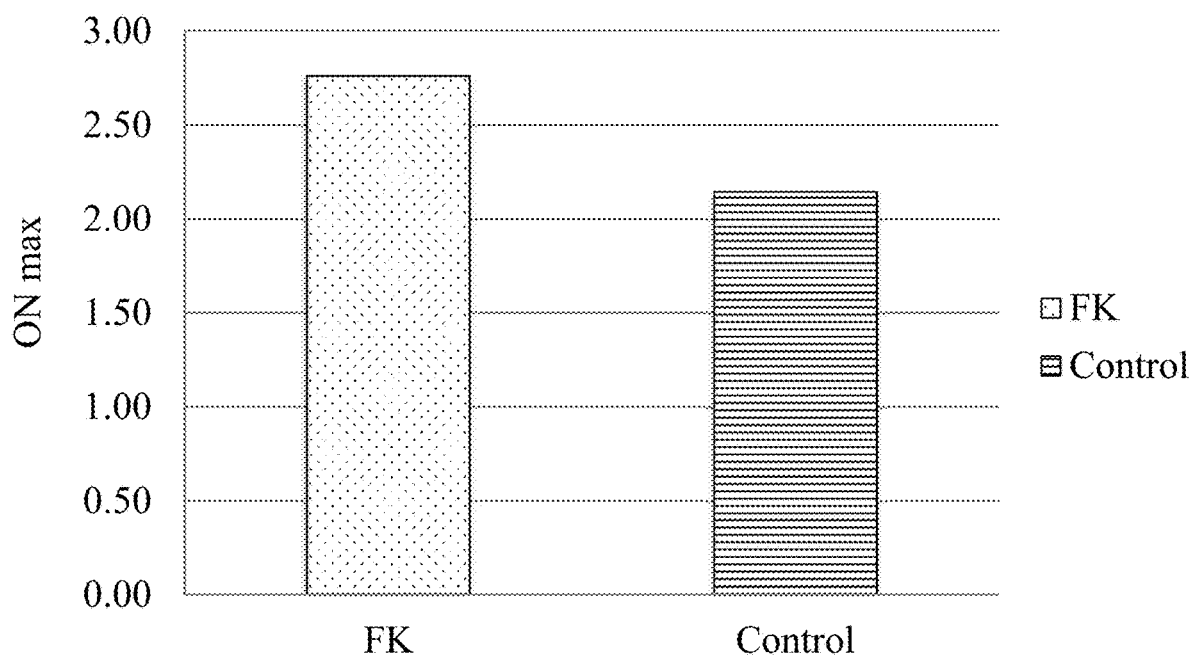

As shown in FIGS. 12A-12B, 20 mg loaded tacrolimus wraps were found to have increased response magnitude at 4 weeks after implantation in the infraorbital cut and repair model. For topical treatment, blood levels of tacrolimus were close to undetectable, particularly as compared to systemic administration through an intraperitoneal injection (FIG. 13).

Example 3: Tacrolimus Impregnated Nerve Wraps Accelerate Peripheral Nerve Generation This Example illustrates the use of a biodegradable matrix for local delivery of tacrolimus as a peripheral nerve treatment using a rodent whisker-trigeminal system model.

Materials and Method

Animals and Surgeries. All animals received care in compliance with the Institutional Animal Care and Use Committee and protocol approval from the University of Pittsburgh and followed guidelines from the Guide for the Care and Use of Laboratory Animals published by the U.S. National Institutes of Health. 10 Lewis rats (RT1) per group (treatment group, non-treatment group), aged 8-10 weeks, were anesthetized with 50 mg/kg intraperitoneal pentobarbital sodium and supplemented as necessary with 10 mg/kg injections. Sterile technique were utilized for all surgeries and a heating pad was used to maintain core animal temperature at 37° C.

The surgical procedure is described in depth in Xiao et al., 2016 and is briefly defined here. Proximal to the mystacial pad, an incision was made on the left hemiface distal to where the infraorbital nerve exits from the infraorbital foramen. Tissue was discretely dissected in order to expose the infraorbital branch of the trigeminal nerve and was transected using microscissors. Following transection, the nerve trunks were coapted using standard microsurgical nerve repair procedure with 10-0 nylon suture using approximately 10 sutures. Following captation of the nerve in the treatment group, FK506 wraps were sutured to itself around the transection and repair portion of the nerve. Following this, the skin incision was repaired with 5-0 chromic dissolvable sutures. The rats were observed until recovery from anesthesia and returned to individual cages. Rats were given a standard 12-h light-dark cycle and rat chow and water were available ad libitum.

FK506-PEUU sheet Fabrication. Poly(ester urethane) urea (PEUU) was synthesized from polycaprolactone diol (Mn=2000), 1,4-diisocyanatobutane and putrescine as described (Guan et al., 2002). Sheets containing FK506 were fabricated by electrospinning (Hong et al., 2011). Methods used to synthesize FK506-PEUU sheets are described in depth in Merwe et al., 2017. Briefly, 20 mg of FK506 was dissolved in DMSO in order to create a 20 mM solution. This FK506 solution was mixed with 0.45 g PEUU, which was dissolved in 1,1,1,3,3,3-hexafluoroisopropanol (HFIP) at a concentration of 12%·(w/v), and electrospun onto a rotating stainless steel mandrel (17 cm from capillary tip) by feeding through a charged capillary at a rate of 1.5 ml/h. Voltage between the capillary and mandrel was 19 kV. Sheets were cut into 50 mm by 50 mm segments with 20 mg FK506 per wrap (5 cm×5 cm=20 mg FK total). The sheet was sterilized under UV light overnight and then with ETO prior to surgical implantation.

Quantification of Tacrolimus concentration in infra orbital nerves, muscle, and PEUU wraps. Infra orbital nerves (IONs), muscle, and PEUU wraps were weighted and homogenized with methanol (100%) using Mini-Bead-Beater-1 for cell or scaffold disruption. The homogenate was left over night in the sonicator to allow for the complete extraction of the drug from the tissues. The homogenate was centrifuged at 2100±100 rpm for 10 min. Supernatant was evaporated by sample concentrator, and the drug residue was reconstituted with blood. Drug concentration was measured by L-CMS/MS and the results were expressed as ng/g of tissue or wrap weight.

Quantification of Tacrolimus by LC-Tandem Mass Spectrometry (LC-MS/MS). Fifty microliters of blood containing an unknown concentration of Tacrolimus was added to a conical centrifugation tube, followed by 200 μL of zinc sulfate heptahydrate ($ZnSO_4.7H_2O$) to precipitate plasma proteins. Five hundred microliters of an acetonitrile based solution containing a deuterated internal standard (ascomycin) at a concentration of 15 ng/ml was then added, and the mixture was vortexed at 3000 rpm for 2 minutes and centrifugated at 13,000 rpm for 3 minutes and the supernatants collected in LCMS vials for analysis.

Analysis was performed using a fully validated, reverse phased method for the detection of TAC in blood on a Waters micromass Quattro micro API mass spectrometer that is operated in positive electrospray ionization mode, utilizing multiple reaction monitoring, with an injection volume of 20 μL. The Waters 2795 Alliance Separations Module was equipped with a nova-pack® C18 column, 2.1×10 mm cartridge (Waters #186003523) heated to 55° C. Analytes were effectively separated using a gradient elution consisting of an aqueous mobile phase (95% $H_2O$/5% MeOH) and an organic mobile phase (100% MeOH), at a flow rate of 0.6 mL per minute. Mobile phases also contained 0.1% formic acid ($CH_2O_2$) and 2 mM ammonium acetate. Results were shown to be linear for concentrations ranging from 2-40 ng/mL with an r2 value of 0.9996. Both intra- and inter-day precision were shown to be acceptable (C.V.<10% n=3) at concentrations of 4.3, 15.7, and 24.6 ng/mL.

Trigeminal ganglion cell recordings. Studies were performed based on procedures as described previously in detail (Xiao, B. et al., 2016). Rats were anesthetized with 1-2% isoflurane in a 1:1 mixture of $N_2$ and $O_2$. A servo-controlled heating pad-maintained core temperature at 37° C. Polyethylene tubing was inserted into the trachea as a cannula, the dorsal surface of the skull was exposed, and a steel post fixed to it with dental acrylic; this allowed unimpeded access to the left facial whiskers. For electrical grounding, a stainless-steel screw was inserted into the frontal region of the animal's skull. A dental drill was used to create a left-sided craniotomy overlying the left trigeminal ganglion at the skull. Neural recordings lasted ~10 hours after which the animal was euthanatized with an overdose of isoflurane. In some cases, the nerve was harvested for later histological evaluation.

Varnish-coated stainless steel or tungsten microelectrodes (2-4 Mohms at 1,000 Hz, FHC, Bowdoin, Me.) were advanced from the brain's dorsal surface into the left trigeminal ganglion using a hydraulic microdrive. Extracellular neural signals, including action potentials or "spikes", were obtained from single trigeminal ganglion cells using standard neural signal recording methods. Spike times, measured at 32 kHz, and spike waveforms were saved to disk for further analysis, including spike waveform sorting techniques to ensure that data were analyzed only from single cells or "units". As the microelectrode was advanced, whiskers were deflected using hand-held probes to identify responsive cells. As reported previously (Xiao, B. et al., 2016), all such units responded to deflection of only single, individual whiskers on the mystacial pad, denoted as the cell's Principal Whisker (PW).

Quantitative neural data were obtained by recording to disk spikes evoked by deflecting the PW in controlled fashion using a multi-angle piezoelectric stimulator that moved the whisker in 8 directions in 45° increments. Each whisker was attached to the stimulator at 10 mm from the skin surface and moved 1 mm using a ramp-and-hold stimulus of 125 mm/s with a plateau duration of 200 ms. Deflections were randomized in 10 blocks of 8 directions in for a total of 80 stimulus presentations. A laboratory computer controlled the stimulator and collected the spike times and waveforms.

Data were analyzed with Microsoft Excel using custom software written in Visual Basic. Responses to whisker movement are transient and brief followed in some cells by lower levels of sustained discharge during the steady-state stimulus plateau. ON responses were quantified as average spike counts per deflection during the first 20 ms following stimulus onset and during the latter 100 ms of the plateau. These counts, expressed as spike per stimulus, were used to identify each cell's maximally effective or "best" deflection angle; deflections in the other directions evoke fewer or no spikes. ON response data were examined separately for maximal angle deflections (n=10) and for deflections averaged over all directions (n=80). Plateau firing rates were low and often null; therefore, only maximal angle spike counts were examined.

Experimental design and analyses. Neural data were analyzed from four groups of animals, all of which experienced nerve transection and surgical repair: 1. 4 week post-transection (hereafter denoted as "4-wk", n=5); 4 weeks post-transection with FK506 treatment ("4-wk-FK", n=6); 6 week post-transection ("6-wk", n=10); and 6 week post-transection with FK506 ("6-wk-FK", n=3). Data for the two Repair-only groups were taken from Xiao et al. (2016). Statistical analyses were performed using the Excel add-on Analyse-t (Analyse-it Software, Leeds, UK). Dunnett tests for multiple comparisons examined spike counts for all four groups using the 6-wk cohort as the control group.

Results

PEUU-Tac significantly increases tacrolimus in the infra-orbital nerves and muscles. Tacrolimus concentrations were analyzed in the intact infra-orbital nerves (IONs) and muscles at 3 days, 1 week, 2 weeks, and 6 weeks post PEUU-Tac implantation. PEUU-Tac significantly increased tacrolimus concentrations in the IONs and muscle but at much lower levels in the whole blood as shown in FIG. 14.

As shown in FIG. 14, at day 3, PEUU-Tac increased tacrolimus concentrations to approximately 673.7±55.7 ng/g in in IONs and 171.3±36.3 ng/g in muscles respectively, and to very lower extend in the blood with 2.6±1.2 ng/ml. Tacrolimus concentrations were sustained with approximately 663.4±115.7 ng/g in IONs and 201±112.7 ng/g in muscle at day 7, and to very lower extend in the blood with 3±1.74 ng/ml. The highest tacrolimus concentrations were achieved at day 14 with approximately 21384±24749.5 ng/g in IONs and 16354.5±24816.6 ng/g in muscles. Tacrolimus concentrations significantly declined to achieve approximately 41.8±43 ng/g in IONs and 51.5±38.3 ng/g in muscle at day 42 (week 6), and to very lower extend in the blood with 0.5±0.26 ng/ml. Similarly, tacrolimus concentrations within the PEUU-Tac wrap were 198305±132576 ng/g (246.6 µM) at day 14, and gradually declined over time to achieve 1434.5±230.6 ng/g (2 µM) at day 42.

Daily systemic (intraperitoneal) injections of tacrolimus in a dose of 1 mg/kg for 14 days increased tacrolimus similarly in both IONs and muscles, but at much lower levels than PEUU-Tac wrap. Tacrolimus concentrations were approximately 195.7±44 ng/g in IONs and 172±34 ng/g in muscle respectively as shown in FIG. 15. These data confirm that PEUU-Tac wraps deliver tacrolimus locally to IONs and the surrounding local tissues, compared to the systemic administration where the drug distributes into the whole system. Interestingly, tacrolimus concentrations in both IONs and muscles days following daily intraperitoneal injections of tacrolimus for 14 days, were similar to the concentrations obtained in IONs and muscles at day 42 post PEUU-Tac wraps implantation.

Tacrolimus concentrations were approximately 351.6±196 in the injured IONs, and 240±171 ng/g in muscle at day 30 and 351.6±196 in the injured IONs and 240±171 ng/g in muscle at day 42 post PEUU-Tac implantation as shown in FIG. 16 (A-B). n=3 animals per group.

PEUU-Tac significantly reduces tacrolimus levels in the blood. Trough Tacrolimus concentrations were analyzed in the whole blood at days 1 and 14 post PEUU-Tac implantation or post systemic injections as shown in FIG. 15. Compared to systemic administration, Tacrolimus blood levels in PEUU-Tac treated animals were significantly lower at all times. At 24 hours, tacrolimus blood levels were detected at 2.6±1.2 ng/ml which is below therapeutic trough levels (5-10 ng/ml), whereas tacrolimus levels in systemically treated animals were high at 18.8±14.8 ng/ml at 24 hours post injection.

At 14 days, tacrolimus levels increased to 3±1.74 ng/ml in PEUU-Tac treated animals. In contrast, tacrolimus levels increased to 14±10.6 ng/ml in systemically treated animals. n=4 animals per group. Error bars represent the SD.

Trigeminal ganglion cell recordings. Effects of the different treatments on trigeminal ganglion cells to whisker deflection are illustrated qualitatively by population peri-stimulus time histograms (PSTHs) in FIG. 16. Here, spike counts for all deflections are accumulated in successive 0.1 ms bins for a period of 30 ms following movement onset which occurs at time 0; the height of each bin is scaled to the total number stimuli (number of animals×8 angles×10 repetitions). ANOVA's for each experimental group indicated that there are no differences related to individual animal subjects, and therefore data are pooled for all recorded cells. In all groups, as in naïve animals (see Xiao et al., 2016), responses are highly transient to the initial movement, display similar time courses, and diminish to low level firing when the whisker is held in a fixed, deflected position. Overall response magnitude is noticeably smaller for 4-week recovery cases without FK treatment (FIG. 16D).

Data were quantified as average spikes per stimulus evoked during the first 20 ms of the response, i.e., ON responses (Table 1 and FIG. 17). For deflections at each cell's maximally effective direction ("Max Angle", FIG. 17A) FK-treated animals at six weeks post-transection responded with the same overall firing rates as control subjects at six weeks without FK (Dunnett's test, p=0.97). Thus, FK treatment did not lead to better functional outcome six weeks after nerve transection and repair. Interestingly, FK-treated animals at 4 weeks post-transection were as responsive to whisker deflections as un-treated animals at six weeks (p=0.49), whereas untreated animals at 4 weeks post-transection were less responsive (p=0.001). Similar results were obtained when ON responses were averaged over all 8 deflection angles and for Plateau responses (Table 1, FIGS. 17B-C). Taken together, the findings indicate that FK treatment accelerated the recovery process but did not lead to improved longer-term outcome.

TABLE 1

| Group | ON Max (20 ms) | ON ALL (20 ms) | Max Plateau (100 ms) |
|---|---|---|---|
| 6-wk (n = 113) | 3.05 ± 1.61 | 1.26 ± 0.65 | 2.10 ± 3.80 |
| 6-wk-FK (n = 57) | 2.95 ± 1.67, p = 0.97 | 1.30 ± 0.68; p = 0.96 | 1.99 ± 3.07; p = 0.99 |
| 4-wk-FK (n = 68) | 2.76 ± 1.51; p = 0.49 | 1.15 ± 0.64, p = 0.34 | 1.62 ± 02.56; p = 0.65 |
| 4-wk (n = 53) | 2.15 ± 1.08; p = 0.001 | 0.89 ± 0.55; p = 0.002 | 0.78 ± 1.50; p = 0.03 |

* p values relative to 6-wk control group (Dunnett test)

Discussion

Peripheral nerve injuries can be devastating, leading to permanent functional disabilities. Systemic FK506 administration has been shown to hasten recovery and improve outcomes after nerve injury repair. However, high systemic levels of FK506 can result in adverse side-effects leading to organ failure as well as other complications. The utility of a novel FK506-impregnated nerve wraps in treating peripheral nerve injuries in a rat infraorbital nerve transection and repair model was tested in this study.

Surgeries were performed on two groups of adult Lewis rats. In both groups, infraorbital branch of the trigeminal nerve was transected. The nerve was then repaired primarily with 10-0 nylon suture with (treatment group) or without (no treatment group) the addition of a Poly(ester urethane) urea (PEUU) wrap impregnated with 20 mg of FK506. To evaluate neuroregeneration, the trigeminal ganglion cell recordings, objective sensory testing, directional sensitivity, maximal response, and receptor compositions were analyzed from five rats in each group at four and six weeks postoperatively. Recordings from the trigeminal ganglion in naïve rats were taken for comparison. To assess local FK506 administration, blood and tissue samples (infraorbital nerve, muscle) were analyzed using liquid chromatography-mass spectrometry at four and six weeks postoperatively in the treatment group.

Data were analyzed using a custom software written in Excel Visual Basic and the Excel add-on statistical package, Analyze-it (Analyse-it Software, LTD). Peristimulus time histograms (PSTHs) having 1 ms bins were constructed from spike times of individual single units. Responses to stimulus onsets (ON responses) were calculated during a 20 ms period beginning 1 ms after deflection onset; this epoch captures the initial, transient phase of the whisker evoked response. Rats within the treatment group (FK506 wraps) were found to have increased response magnitude at 4 weeks after implantation in the infraorbital cut and repair model in comparison to no treatment group (p<0.013, FIG. 17). FK506 blood levels at 4 and 6 weeks were close to the limit of quantification (<2 ng/ml), whereas concentration within the tissues of interest, the infraorbital nerve and muscle, was much higher.

The use of an FK506-impregnated PEUU nerve wrap improved healing following peripheral nerve injury. Sensory testing provides objective data on the effects of these wraps in the treatment of peripheral nerve injuries and the FK wraps appear to accelerate nerve recovery, with minimal systemic drug exposure. The findings from this study can be translated into novel treatment systems and protocols for nerve injuries.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various references are cited in this document, which are hereby incorporated by reference in their entireties herein.

7. REFERENCES

1. Ahearn, I. M., F. D. Tsai, H. Court, M. Zhou, B. C. Jennings, M. Ahmed, N. Fehrenbacher, M. E. Linder and M. R. Philips (2011). "FKBP12 binds to acylated H-ras and promotes depalmitoylation." *Mol Cell* 41(2): 173-185.
2. Barres, B. A., B. E. Silverstein, D. P. Corey and L. L. Chun (1988). "Immunological, morphological, and electrophysiological variation among retinal ganglion cells purified by panning." *Neuron* 1(9): 791-803.
3. Bei, F., H. H. Lee, X. Liu, G. Gunner, H. Jin, L. Ma, C. Wang, L. Hou, T. K. Hensch, E. Frank, J. R. Sanes, C. Chen, M. Fagiolini and Z. He (2016). "Restoration of Visual Function by Enhancing Conduction in Regenerated Axons." *Cell* 164(1-2): 219-232.
4. Bottiger, Y., C. Brattstrom, G. Tyden, J. Sawe and C. G. Groth (1999). "Tacrolimus whole blood concentrations correlate closely to side-effects in renal transplant recipients." *Br J Clin Pharmacol* 48(3): 445-448.
5. Cai, J., K. S. Ziemba, G. M. Smith and Y. Jin (2007). "Evaluation of cellular organization and axonal regeneration through linear PLA foam implants in acute and chronic spinal cord injury." *J Biomed Mater Res A* 83(2): 512-520.
6. Cottrell, B L., Perez-Abadia, G., Onifer, S M., Magnuson, D S., Burke, D A., Grossi, F V., Francois, C G., Barker, J H., and Maldonado, C (2006) "Neuroregeneration in composite tissue allografts: effect of low-dose FK506 and mycophenolate mofetil immunotherapy." *Plast Reconstr Surg* 118(3): p. 615-23; discussion 624-5.
7. Davaus Gasparetto, T., Marchiori, E., Menezes, P., Zanetti, G. (2010) "Pulmonary toxicity associated with sirolimus following kidney transplantation: computed tomography findings." *Nefrologia*, 30(2): p. 259-60.
8. Dehghani, S. M., Haghighat, M., Imanieh, M H., Zahmatkeshan, M., Borzooei, M., Amoozegar, H., Zamirian, M., Gholami, S., Bahador, A., Nikeghbalian, S., Salahi, H., Malek-Hosseini, S A. (2010) "Tacroli- 9. de Lima, S., G. Habboub and L. I. Benowitz (2012). "Combinatorial therapy stimulates long-distance regeneration, target reinnervation, and partial recovery of vision after optic nerve injury in mice." *Int Rev Neurobiol* 106: 153-172.
10. Den Dunnen, W. F., M. F. Meek, P. H. Robinson and J. M. Schakernraad (1998). "Peripheral nerve regeneration through P(DLLA-epsilon-CL) nerve guides." *J Mater Sci Mater Med* 9(12): 811-814.
11. Deuse, T., F. Blankenberg, M. Haddad, H. Reichenspurner, N. Phillips, R. C. Robbins and S. Schrepfer (2010). "Mechanisms behind local immunosuppression using inhaled tacrolimus in preclinical models of lung transplantation." *Am J Respir Cell Mol Biol* 43(4): 403-412.
12. Fischer, D., Z. He and L. I. Benowitz (2004). "Counteracting the Nogo receptor enhances optic nerve regeneration if retinal ganglion cells are in an active growth state." *J Neurosci* 24(7): 1646-1651.
13. Freeman, E. E. and C. L. Grosskreutz (2000). "The effects of FK506 on retinal ganglion cells after optic nerve crush." *Invest Ophthalmol Vis Sci* 41(5): 1111-1115.
14. Fukuta, T., T. Ishii, T. Asai, A. Sato, T. Kikuchi, K. Shimizu, T. Minamino and N. Oku (2015). "Treatment of stroke with liposomal neuroprotective agents under cerebral ischemia conditions." *Eur J Pharm Biopharm* 97(Pt A): 1-7.
15. Fu S. Y. and Gordon T. (1995). "Contributing factors to poor functional recovery after delayed nerve repair: prolonged axotomy." *J Neurosci* 15(5 Pt2):3876-85.
16. Gabriel, D., T. Mugnier, H. Courthion, K. Kranidioti, N. Karagianni, M. C. Denis, M. Lapteva, Y. Kalia, M. Moller and R. Gurny (2016). "Improved topical delivery of tacrolimus: A novel composite hydrogel formulation for the treatment of psoriasis." *J Control Release* 242: 16-24.
17. Gnatta, D., Keitel, E., Heineck, I., Cardoso, B. D., Rodrigues, A. P., Michel, K., and Garcia, V. D. (2010) "Use of tacrolimus and the development of posttransplant diabetes mellitus: a Brazilian single-center, observational study." *Transplant Proc* 42(2): p. 475-8.
18. Gold, B. G., D. M. Armistead and M. S. Wang (2005). "Non-FK506-binding protein-12 neuroimmunophilin ligands increase neurite elongation and accelerate nerve regeneration." *J Neurosci Res* 80(1): 56-65.
19. Gold, B. G., V. Densmore, W. Shou, M. M. Matzuk and H. S. Gordon (1999). "Immunophilin FK506-binding protein 52 (not FK506-binding protein 12) mediates the neurotrophic action of FK506." *J Pharmacol Exp Ther* 289(3): 1202-1210.
20. Gold, B. G., H. S. Gordon and M. S. Wang (1999). "Efficacy of delayed or discontinuous FK506 administrations on nerve regeneration in the rat sciatic nerve crush model: lack of evidence for a conditioning lesion-like effect." *Neurosci Lett* 267(1): 33-36.
21. Goldberg, J. L., M. P. Klassen, Y. Hua and B. A. Barres (2002). "Amacrine-signaled loss of intrinsic axon growth ability by retinal ganglion cells." *Science* 296(5574): 1860-1864.
22. Gottschaldt K. M., Vahle-Hinz C. (1981). "Merkel cell receptors: structure and transducer function." *Science.* 214:183-186.
23. Guan, J., M. S. Sacks, E. J. Beckman and W. R. Wagner (2002). "Synthesis, characterization, and cytocompatibility of elastomeric, biodegradable poly(ester-urethane)ureas based on poly(caprolactone) and putrescine." *J Biomed Mater Res* 61(3): 493-503.
24. Hadlock, T., C. Sundback, R. Koka, D. Hunter, M. Cheney and J. Vacanti (1999). "A novel, biodegradable polymer conduit delivers neurotrophins and promotes nerve regeneration." *Laryngoscope* 109(9): 1412-1416.
25. Hong, Y., J. Guan, K. L. Fujimoto, R. Hashizume, A. L. Pelinescu and W. R. Wagner (2010). "Tailoring the degradation kinetics of poly(ester carbonate urethane) urea thermoplastic elastomers for tissue engineering scaffolds." *Biomaterials* 31(15): 4249-4258.
26. Hong, Y., A. Huber, K. Takanari, N. J. Amoroso, R. Hashizume, S. F. Badylak and W. R. Wagner (2011). "Mechanical properties and in vivo behavior of a biodegradable synthetic polymer microfiber-extracellular matrix hydrogel biohybrid scaffold." *Biomaterials* 32(13): 3387-3394.
27. Horn, K. P., S. A. Busch, A. L. Hawthorne, N. van Rooijen and J. Silver (2008). "Another barrier to regeneration in the CNS: activated macrophages induce extensive retraction of dystrophic axons through direct physical interactions." *J Neurosci* 28(38): 9330-9341.
28. Houdek, M. T. and A. Y. Shin (2015). "Management and complications of traumatic peripheral nerve injuries." *Hand Clin,* 2015. 31(2): p. 151-63.
29. Howrie, D. L., R. J. Ptachcinski, B. P. Griffith, R. J. Hardesty, J. T. Rosenthal, G. J. Burckart and R. Venkataramanan (1985). "Anaphylactoid reactions associated with parenteral cyclosporine use: possible role of Cremophor EL." *Drug Intell Clin Pharm* 19(6): 425-427.
30. Jean, W. C., S. R. Spellman, E. S. Nussbaum and W. C. Low (1998). "Reperfusion injury after focal cerebral ischemia: the role of inflammation and the therapeutic horizon." *Neurosurgery* 43(6): 1382-1396; discussion 1396-1387.
31. Kim, J. S., Baek G H., Chung M S., Park H Y., and Sun J H (2014) "Effects of FK-506 and CTLA4-Ig on nerve allografts in mice." *J Plast Reconstr Aesthet Surg,* 67(2): p. e49-53.
32. Klettner, A. and T. Herdegen (2003). "The immunophilin-ligands FK506 and V-10,367 mediate neuroprotection by the heat shock response." *Br J Pharmacol* 138(5): 1004-1012.
33. Konofaos, P. and J. K. Terzis (2013) "FK506 and nerve regeneration: past, present, and future." *J Reconstr Microsurg* 29(3): p. 141-8.
34. Labroo, P., S. Ho, H. Sant, J. Shea, B. K. Gale and J. Agarwal (2016). "Controlled Delivery of FK506 to Improve Nerve Regeneration." *Shock.*
35. Labroo, P., J. Shea, H. Sant, B. Gale and J. Agarwal (2016). "Effect of combining FK506 and neurotrophins on neurite branching and elongation." *Muscle Nerve.*
36. Lamprecht, A., Yamamoto, H., Takeuchi, H., and Kawashima, Y. (2004) "Design of pH-sensitive microspheres for the colonic delivery of the immunosuppressive drug tacrolimus." *Eur J Pharm Biopharm* 58(1): p. 37-43.
37. Lapteva, M., K. Mondon, M. Moller, R. Gurny and Y. N. Kalia (2014). "Polymeric micelle nanocarriers for the cutaneous delivery of tacrolimus: a targeted approach for the treatment of psoriasis." *Mol Pharm* 11(9): 2989-3001.

38. Lee, S. H., Simons, D. J. (2004). "Angular tuning and velocity sensitivity in different neuron classes within layer 4 of rat barrel cortex." *J Neurophysiol* 91(1):223-229.
39. Leroy, S., Isapof, A., Fargue, S., Fakhoury, M., Bensman, A., Deschênes, G., Jacqz-Aigrain, E., Ulinski, T. (2010) "Tacrolimus nephrotoxicity: beware of the association of diarrhea, drug interaction and pharmacogenetics." *Pediatr Nephrol* 25(5): p. 965-9.
40. Li, T., Zhang, X J., Li, J., and Kan, Q C. (2014) "Effect of FK506 nanospheres on regeneration of allogeneic nerve after transplant." *Asian Pac J Trop Med* 7(6): p. 478-82.
41. Lichtenstein, S. H., Carvell G. E., Simons D. J. (1990). "Responses of rat trigeminal ganglion neurons to movements of vibrissae in different directions." *Somatosens Mot Res.* 7(1):47-65.
42. Liu, J., J. D. Farmer, Jr., W. S. Lane, J. Friedman, I. Weissman and S. L. Schreiber (1991). "Calcineurin is a common target of cyclophilin-cyclosporin A and FKBP-FK506 complexes." *Cell* 66(4): 807-815.
43. Liu, W., Y. Tang and J. Feng (2011). "Cross talk between activation of microglia and astrocytes in pathological conditions in the central nervous system." *Life Sci* 89(5-6): 141-146.
44. Lyons, W. E., E. B. George, T. M. Dawson, J. P. Steiner and S. H. Snyder (1994). "Immunosuppressant FK506 promotes neurite outgrowth in cultures of PC12 cells and sensory ganglia." *Proc Natl Acad Sci USA* 91(8): 3191-3195.
45. Madduri, S. and B. Gander (2012). "Growth factor delivery systems and repair strategies for damaged peripheral nerves." *J Control Release* 161(2): 274-282.
46. Madsen, J. R., P. MacDonald, N. Irwin, D. E. Goldberg, G. L. Yao, K. F. Meiri, I. J. Rimm, P. E. Stieg and L. I. Benowitz (1998). "Tacrolimus (FK506) increases neuronal expression of GAP-43 and improves functional recovery after spinal cord injury in rats." *Exp Neurol* 154(2): 673-683.
47. Mayer, A. D., J. Dmitrewski, J. P. Squifflet, T. Besse, B. Grabensee, B. Klein, F. W. Eigler, U. Heemann, R. Pichlmayr, M. Behrend, Y. Vanrenterghem, J. Donck, J. van Hooff, M. Christiaans, J. M. Morales, A. Andres, R. W. Johnson, C. Short, B. Buchholz, N. Rehmert, W. Land, S. Schleibner, J. L. Forsythe, D. Talbot, E. Pohanka and et al. (1997). "Multicenter randomized trial comparing tacrolimus (FK506) and cyclosporine in the prevention of renal allograft rejection: a report of the European Tacrolimus Multicenter Renal Study Group." *Transplantation* 64(3): 436-443.
48. Noble, J., Munro, C. A., Prasad, V. S., Midha, R., (1998). "Analysis of upper and lower extremity peripheral nerve injuries in a population of patients with multiple injuries." *J. Trauma* 45, 116-122.
49. Oto T., Okazaki M., Takata K., Egi M., Yamane M., Toyooka S., Sano Y., Snell G I., Goto K., Miyoshi S. (2010) "Calcineurin inhibitor-related cholestasis complicating lung transplantation." *Ann Thorac Surg,* 89(5): p. 1664-5.
50. Pabari, A., H. Lloyd-Hughes, A. M. Seifalian and A. Mosahebi (2014). "Nerve conduits for peripheral nerve surgery." *Plast Reconstr Surg* 133(6): 1420-1430.
51. Pernet, V. and M. E. Schwab (2014). "Lost in the jungle: new hurdles for optic nerve axon regeneration." *Trends Neurosci* 37(7): 381-387.
52. Peruzzotti-Jametti, L., M. Donega, E. Giusto, G. Mallucci, B. Marchetti and S. Pluchino (2014). "The role of the immune system in central nervous system plasticity after acute injury." *Neuroscience* 283: 210-221.
53. Randhawa, P. S., T. E. Starzl and A. J. Demetris (1997). "Tacrolimus (FK506)-Associated Renal Pathology." *Adv Anat Pathol* 4(4): 265-276.
54. Resnikoff, S., D. Pascolini, D. Etya'ale, I. Kocur, R. Pararajasegaram, G. P. Pokharel and S. P. Mariotti (2004). "Global data on visual impairment in the year 2002." *Bull World Health Organ* 82(11): 844-851.
55. Rice F. L. (1986). "Gradual changes in the structure of the barrels during maturation of the primary somatosensory cortex in the rat." *J Comp Neurol.* 249:429-459.
56. Rosenstiel, P., P. Schramm, S. Isenmann, S. Brecht, C. Eickmeier, E. Burger, T. Herdegen, J. Sievers and R. Lucius (2003). "Differential effects of immunophilin-ligands (FK506 and V-10,367) on survival and regeneration of rat retinal ganglion cells in vitro and after optic nerve crush in vivo." *J Neurotrauma* 20(3): 297-307.
57. Russo, R., G. P. Varano, A. Adornetto, C. Nucci, M. T. Corasaniti, G. Bagetta and L. A. Morrone (2016). "Retinal ganglion cell death in glaucoma: exploring the role of neuroinflammation." *Eur J Pharmacol.*
58. Sarikcioglu, L., N. Demir and A. Demirtop (2007). "A standardized method to create optic nerve crush: Yasargil aneurysm clip." *Exp Eye Res* 84(2): 373-377.
59. Schmidt, C. E., and Leach, J. N (2003). "Neural tissue engineering: strategies for repair and regeneration." *Annu Rev Biomed Eng.* 2003. 5: p. 293-347.
60. Shahraki, M., R. Mohammadi, and A. Najafpour (2015). "Influence of Tacrolimus (FK506) on Nerve Regeneration Using Allografts: A Rat Sciatic Nerve Model." *J Oral Maxillofac Surg,* 2015. 73(7): p. 1438 e1-9.
61. Sharifi, Z. N., F. Abolhassani, M. R. Zarrindast, S. Movassaghi, N. Rahimian and G. Hassanzadeh (2012). "Effects of FK506 on Hippocampal CA1 Cells Following Transient Global Ischemia/Reperfusion in Wistar Rat." *Stroke Res Treat* 2012: 809417. Silver, J. and J. H. Miller (2004). "Regeneration beyond the glial scar." *Nat Rev Neurosci* 5(2): 146-156.
62. Simons, D. J. (1983). "Multi-whisker stimulation and its effects on vibrissa units in rat SmI barrel cortex." *Brain Res.* 276(1):178-182.
63. Stankus, J. J., J. Guan and W. R. Wagner (2004). "Fabrication of biodegradable elastomeric scaffolds with sub-micron morphologies." *J Biomed Mater Res A* 70(4): 603-614.
64. Starzl, T. E., S. Todo, J. Fung, A. J. Demetris, R. Venkataramman and A. Jain (1989). "FK 506 for liver, kidney, and pancreas transplantation." *Lancet* 2(8670): 1000-1004.
65. Steketee, M. B., C. Oboudiyat, R. Daneman, E. Trakhtenberg, P. Lamoureux, J. E. Weinstein, S. Heidemann, B. A. Barres and J. L. Goldberg (2014). "Regulation of intrinsic axon growth ability at retinal ganglion cell growth cones." *Invest Ophthalmol Vis Sci* 55(7): 4369-4377.
66. Szydlowska, K., M. Zawadzka and B. Kaminska (2006). "Neuroprotectant FK506 inhibits glutamate-induced apoptosis of astrocytes in vitro and in vivo." *J Neurochem* 99(3): 965-975.
67. Tajdaran, K., M. S. Shoichet, T. Gordon and G. H. Borschel (2015). "A novel polymeric drug delivery system for localized and sustained release of tacrolimus (FK506)." *Biotechnol Bioeng* 112(9): 1948-1953.
68. Tang, S., J. Qiu, E. Nikulina and M. T. Filbin (2001). "Soluble myelin-associated glycoprotein released from damaged white matter inhibits axonal regeneration." *Mol Cell Neurosci* 18(3): 259-269.
69. Tricot, L., Lebbé, C, Pillebout, E., Martinez, F., Legendre, C., Thervet, E. (2005) "Tacrolimus-induced alopecia in female kidney-pancreas transplant recipients." *Transplantation* 80(11): p. 1546-9.
70. Tocci, M. J., D. A. Matkovich, K. A. Collier, P. Kwok, F. Dumont, S. Lin, S. Degudicibus, J. J. Siekierka, J. Chin and N. I. Hutchinson (1989). "The immunosuppressant FK506 selectively inhibits expression of early T cell activation genes." *J Immunol* 143(2): 718-726.
71. Varghese, J., M. S. Reddy, K. Venugopal, R. Perumalla, G. Narasimhan, O. Arikichenin, V. Shanmugam, N. Shanmugam, V. Srinivasan, V. Jayanthi and M. Rela (2014). "Tacrolimus-related adverse effects in liver transplant recipients: its association with trough concentrations." *Indian J Gastroenterol* 33(3): 219-225.
72. Voda, J., T. Yamaji and B. G. Gold (2005). "Neuroimmunophilin ligands improve functional recovery and increase axonal growth after spinal cord hemisection in rats." *J Neurotrauma* 22(10): 1150-1161.
73. Wang, M. S. and B. G. Gold (1999). "FK506 increases the regeneration of spinal cord axons in a predegenerated peripheral nerve autograft." *J Spinal Cord Med* 22(4): 287-296.
74. Xu, X., B. Su, R. J. Barndt, H. Chen, H. Xin, G. Yan, L. Chen, D. Cheng, J. Heitman, Y. Zhuang, S. Fleischer and W. Shou (2002). "FKBP12 is the only FK506 binding protein mediating T-cell inhibition by the immunosuppressant FK506." *Transplantation* 73(11): 1835-1838.
75. Yamazoe, K., K. Yamazoe, T. Yamaguchi, M. Omoto and J. Shimazaki (2014). "Efficacy and safety of systemic tacrolimus in high-risk penetrating keratoplasty after graft failure with systemic cyclosporine." *Cornea* 33(11): 1157-1163.
76. Yang, L. M., et al. (2014). "Experimental research on end-to-side anastomosis of peripheral nerves and effect of FK506 on end-to-side anastomosis." *Bratisl Lek Listy,* 115(10): p. 625-31.
77. Young, M. J. (2005). "Stem cells in the mammalian eye: a tool for retinal repair." *APMIS* 113(11-12): 845-857.
78. Zhang, G., et al., (2007) "Application of FK506 slow-releasing film in peripheral nerve allotransplantation: an experimental study in mice." *Chin J Hand Surg* 23: p. 8-10.
79. Zawadzka, M., M. Dabrowski, A. Gozdz, B. Szadujkis, M. Sliwa, M. Lipko and B. Kaminska (2012). "Early steps of microglial activation are directly affected by neuroprotectant FK506 in both in vitro inflammation and in rat model of stroke." *J Mol Med* (Berl) 90(12): 1459-1471.
80. Zawadzka, M. and B. Kaminska (2005). "A novel mechanism of FK506-mediated neuroprotection: downregulation of cytokine expression in glial cells." *Glia* 49(1): 36-51.

What is claimed is:

1. A device for local delivery of tacrolimus, comprising a polymeric matrix, wherein the polymeric matrix comprises an effective amount of a biodegradable polymer and tacrolimus,
wherein the polymeric matrix is in a form of an electrospun nerve wrap having a Young's modulus between from about 5 MPa to about 50 MPa, suture retention strength of at least 100 gram-force, an ultimate stress of from about 3 MPa to about 9 MPa, and a strain at break between from about 50% to about 300%;
wherein the electrospun nerve wrap is impregnated with the tacrolimus in an amount of from about 1 mg to about 100 mg, wherein the tacrolimus and biodegradable polymer are impregnated in a weight ratio of from about 1:20 to about 1:50 in the electrospun nerve wrap.

2. The device of claim 1, wherein the biodegradable polymer comprises poly(ester urethane) urea.

3. The device of claim 1, wherein the biodegradable polymer has a number average molecular weight of from about 40,000 Da to about 200,000 Da.

4. The device of claim 1, wherein the device is configured as a sheet.

5. The device of claim 1, further comprising an attachment mechanism for securing the device to nervous system tissue.

6. A method for local delivery of tacrolimus to a nervous system tissue in a subject, comprising applying the device of claim 1, to an implantation site in the subject.

7. The method of claim 6, further comprising securing the polymeric matrix to the implantation site.

8. The method of claim 6, wherein tacrolimus is released from the polymeric matrix over a period of from about 10 days to about 15 days.

9. The method of claim 6, wherein the implantation site is local to the nervous system tissue.

10. The method of claim 6, wherein the nervous system tissue comprises a nerve.

11. The method of claim 6, wherein the nervous system tissue comprises an optic nerve.

12. The method of claim 6, wherein a concentration of tacrolimus in blood of the subject is maintained at less than about 20 ng/mL.

13. A method of treating an injury to nervous system tissue in a subject, comprising:
   a. applying the device of claim 1; and
   b. releasing an effective amount of tacrolimus to the vicinity of the nervous system tissue.

14. The method of claim 13, wherein the nervous system tissue comprises a nerve.

15. The method of claim 13, wherein the nervous system tissue comprises an optic nerve.

16. The method of claim 13, wherein a concentration of tacrolimus in blood of the subject is maintained at less than about 20 ng/mL.

17. A method of making the device of claim 1 for local delivery of tacrolimus, comprising:
   a. providing a first solution comprising tacrolimus and a first solvent;
   b. providing a second solution comprising the biodegradable polymer and a second solvent;
   c. combining the first solution and the second solution to form a mixture; and
   d. electrospinning the polymeric matrix comprising the biodegradable polymer and tacrolimus from the mixture.

18. The method of claim 17, further comprising forming the biodegradable polymer in the second solution.

19. The method of claim 17, wherein the biodegradable polymer comprises poly(ester urethane) urea.

20. The method of claim 19, further comprising forming poly(ester urethane) urea in the first solution by reacting polycaprolactone diol, 1,4-diisocyanatobutane, and putrescine.

21. The method of claim 17, wherein the first solvent comprises dimethyl sulfoxide.

22. The method of claim 17, wherein the second solvent comprises hexafluoroisopropanol.

23. The method of claim 17, further comprising sterilizing the device.

24. The method of claim 23, wherein the device is sterilized by exposing the device to radiation.

25. The method of claim 23, wherein the device is sterilized by contacting the device with ethylene oxide.

26. The method of claim 6, wherein the nervous system tissue comprises an infra orbital nerve.

27. The device of claim 4, wherein the sheet is modified based on a geometry of an implantation site.

28. The device of claim 1, wherein the biodegradable polymer has a number average molecular weight of from about 50,000 Da to about 100,000 Da.

29. The method of claim 6, wherein the biodegradable polymer comprises poly(ester urethane) urea.

30. The method of claim 13, wherein the biodegradable polymer comprises poly(ester urethane) urea.

\* \* \* \* \*